(12) United States Patent
Ju et al.

(10) Patent No.: US 10,260,094 B2
(45) Date of Patent: Apr. 16, 2019

(54) DNA SEQUENCING WITH NON-FLUORESCENT NUCLEOTIDE REVERSIBLE TERMINATORS AND CLEAVABLE LABEL MODIFIED NUCLEOTIDE TERMINATORS

(71) Applicants: Jingyue Ju, Englewood Cliffs, NJ (US);
Dae Hyun Kim, Northbrook, IL (US);
Jia Guo, New York, NY (US); Qinglin Meng, Foster City, CA (US); Zengmin Li, Flushing, NY (US); Huanyan Cao, Jiangyin (CN)

(72) Inventors: Jingyue Ju, Englewood Cliffs, NJ (US);
Dae Hyun Kim, Northbrook, IL (US);
Jia Guo, New York, NY (US); Qinglin Meng, Foster City, CA (US); Zengmin Li, Flushing, NY (US); Huanyan Cao, Jiangyin (CN)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 530 days.

(21) Appl. No.: 14/820,254

(22) Filed: Aug. 6, 2015

(65) Prior Publication Data
US 2016/0024574 A1 Jan. 28, 2016

Related U.S. Application Data

(63) Continuation of application No. 12/734,229, filed as application No. PCT/US2008/011913 on Oct. 17, 2008, now Pat. No. 9,115,163.

(Continued)

(51) Int. Cl.
C12Q 1/68 (2018.01)
C12Q 1/6874 (2018.01)
(Continued)

(52) U.S. Cl.
CPC .......... *C12Q 1/6874* (2013.01); *C07H 19/04* (2013.01); *C12Q 1/6869* (2013.01);
(Continued)

(58) Field of Classification Search
USPC ....................................................... 435/6.12
See application file for complete search history.

(56) References Cited

U.S. PATENT DOCUMENTS 4,711,955 A 12/1987 Ward
4,772,691 A 9/1988 Herman
(Continued)

FOREIGN PATENT DOCUMENTS

CA 2425112 9/2011
DE 4141178 6/1993
(Continued)

OTHER PUBLICATIONS

U.S. Appl. No. 09/684,670, filed Oct. 6, 2000, Ju et al.
(Continued)

*Primary Examiner* — Jezia Riley
(74) *Attorney, Agent, or Firm* — John P. White; Gary J. Gershik; Cooper & Dunham LLP

(57) ABSTRACT

This invention provides a process for sequencing nucleic acids using 3' modified deoxynucleotide analogs or 3' modified deoxyinosine triphosphate analogs, and 3' modified dideoxynucleotide analogs having a detectable marker attached to a base thereof.

8 Claims, 32 Drawing Sheets

Specification includes a Sequence Listing.

Related U.S. Application Data

(60) Provisional application No. 60/999,580, filed on Oct. 19, 2007, provisional application No. 60/999,575, filed on Oct. 19, 2007.

(51) Int. Cl.
*C07H 19/04* (2006.01)
*C12Q 1/6869* (2018.01)
*C12Q 1/6876* (2018.01)
*A61K 31/70* (2006.01)

(52) U.S. Cl.
CPC ............ *C12Q 1/6876* (2013.01); *A61K 31/70* (2013.01); *C12Q 2523/107* (2013.01); *C12Q 2523/319* (2013.01); *C12Q 2535/101* (2013.01); *C12Q 2535/113* (2013.01); *C12Q 2563/107* (2013.01)

(56) References Cited

U.S. PATENT DOCUMENTS

| | | |
|---|---|---|
| 4,804,748 A | 2/1989 | Seela |
| 4,824,775 A | 4/1989 | Dattagupta |
| 4,863,849 A | 9/1989 | Melamede |
| 5,043,272 A | 8/1991 | Hartley |
| 5,047,519 A | 9/1991 | Hobbs, Jr. et al. |
| 5,118,605 A | 6/1992 | Urdea |
| 5,151,507 A | 9/1992 | Hobbs, Jr. et al. |
| 5,174,962 A | 12/1992 | Brennan |
| 5,175,269 A | 12/1992 | Stavrianopoulos |
| 5,242,796 A | 9/1993 | Prober et al. |
| 5,302,509 A | 4/1994 | Cheeseman |
| 5,308,990 A | 5/1994 | Takahashi et al. |
| 5,328,824 A | 7/1994 | Ward et al. |
| 5,332,666 A | 7/1994 | Prober et al. |
| 5,383,858 A | 1/1995 | Reilly et al. |
| 5,436,143 A | 7/1995 | Hyman |
| 5,437,975 A | 8/1995 | McClelland et al. |
| 5,449,767 A | 9/1995 | Ward et al. |
| 5,476,928 A | 12/1995 | Ward |
| 5,516,664 A | 5/1996 | Hyman |
| 5,534,424 A | 7/1996 | Uhlen et al. |
| 5,547,839 A | 8/1996 | Dower et al. |
| 5,547,859 A | 8/1996 | Goodman et al. |
| 5,556,748 A | 9/1996 | Douglas |
| 5,599,675 A | 2/1997 | Brenner |
| 5,602,000 A | 2/1997 | Hyman |
| 5,637,469 A | 6/1997 | Wilding et al. |
| 5,654,419 A | 8/1997 | Mathies |
| 5,658,736 A | 8/1997 | Wong |
| 5,709,999 A | 1/1998 | Shattuck et al. |
| 5,728,528 A | 3/1998 | Mathies |
| 5,763,594 A | 6/1998 | Hiatt et al. |
| 5,770,365 A | 6/1998 | Lane et al. |
| 5,770,367 A | 6/1998 | Southern et al. |
| 5,789,167 A | 8/1998 | Konrad |
| 5,798,210 A | 8/1998 | Canard et al. |
| 5,804,386 A | 9/1998 | Ju |
| 5,808,045 A | 9/1998 | Hiatt et al. |
| 5,814,454 A | 9/1998 | Ju |
| 5,821,356 A | 10/1998 | Khan et al. |
| 5,834,203 A | 11/1998 | Katzir |
| 5,844,106 A | 12/1998 | Seela et al. |
| 5,849,542 A | 12/1998 | Reeve et al. |
| 5,853,992 A | 12/1998 | Glazer |
| 5,856,104 A | 1/1999 | Chee et al. |
| 5,869,255 A | 2/1999 | Mathies |
| 5,872,244 A | 2/1999 | Hiatt et al. |
| 5,876,936 A | 3/1999 | Ju |
| 5,885,775 A | 3/1999 | Haff et al. |
| 5,908,755 A | 6/1999 | Kumar et al. |
| 5,945,283 A | 8/1999 | Kwok |
| 5,948,648 A | 9/1999 | Khan et al. |
| 5,952,180 A | 9/1999 | Ju |
| 5,959,089 A | 9/1999 | Hannessian |
| 5,962,228 A | 10/1999 | Brenner |
| 6,001,566 A | 12/1999 | Canard et al. |
| 6,001,611 A | 12/1999 | Will |
| 6,008,379 A | 12/1999 | Benson et al. |
| 6,013,445 A | 1/2000 | Albrecht et al. |
| 6,028,190 A | 2/2000 | Mathies |
| 6,046,005 A | 4/2000 | Ju et al. |
| 6,074,823 A | 6/2000 | Koster |
| 6,087,095 A | 7/2000 | Rosenthal et al. |
| 6,136,543 A | 10/2000 | Anazawa et al. |
| 6,175,107 B1 | 1/2001 | Juvinall |
| 6,197,557 B1 | 3/2001 | Markarov et al. |
| 6,207,831 B1 | 3/2001 | Auer et al. |
| 6,210,891 B1 | 4/2001 | Nyren et al. |
| 6,214,987 B1 | 4/2001 | Hiatt et al. |
| 6,218,118 B1 | 4/2001 | Sampson |
| 6,218,530 B1 | 4/2001 | Rothschild et al. |
| 6,221,592 B1 | 4/2001 | Schwartz et al. |
| 6,232,465 B1 | 5/2001 | Hiatt et al. |
| 6,242,193 B1 | 6/2001 | Anazawa et al. |
| 6,245,507 B1 | 6/2001 | Bogdanov |
| 6,255,083 B1 | 7/2001 | Williams |
| 6,255,475 B1 | 7/2001 | Kwiatkowski |
| 6,274,320 B1 | 8/2001 | Rothberg et al. |
| 6,277,607 B1 | 8/2001 | Tyagi et al. |
| 6,287,821 B1 | 9/2001 | Shi et al. |
| 6,294,324 B1 | 9/2001 | Bensimon et al. |
| 6,309,829 B1 | 10/2001 | Livak et al. |
| 6,309,836 B1 | 10/2001 | Kwiatkowski |
| 6,312,893 B1 | 11/2001 | Van Ness et al. |
| 6,316,230 B1 | 11/2001 | Egholm |
| 6,361,940 B1 | 3/2002 | Van Ness et al. |
| 6,380,378 B1 | 4/2002 | Kitamura et al. |
| 6,524,829 B1 | 2/2003 | Seeger |
| 6,555,349 B1 | 4/2003 | O'Donnell |
| 6,613,508 B1 | 9/2003 | Ness et al. |
| 6,613,513 B1 | 9/2003 | Kopf-Sill et al. |
| 6,627,748 B1 | 9/2003 | Ju et al. |
| 6,632,655 B1 | 10/2003 | Mehta et al. |
| 6,639,088 B2 | 10/2003 | Kwiatkowski |
| 6,664,079 B2 | 12/2003 | Ju et al. |
| 6,664,399 B1 | 12/2003 | Sabesan |
| 6,713,255 B1 | 3/2004 | Makino et al. |
| 6,780,591 B2 | 8/2004 | Williams et al. |
| 6,787,308 B2 | 9/2004 | Balasubramanian et al. |
| 6,818,395 B1 | 11/2004 | Quake et al. |
| 6,833,246 B2 | 12/2004 | Balasubramanian |
| 6,864,052 B2 | 3/2005 | Drmanac et al. |
| 6,911,345 B2 | 6/2005 | Quake et al. |
| 6,934,636 B1 | 8/2005 | Skierczynski et al. |
| 6,982,146 B1 | 1/2006 | Schneider et al. |
| 7,037,687 B2 | 5/2006 | Williams et al. |
| 7,056,661 B2 | 6/2006 | Korlach et al. |
| 7,056,666 B2 | 6/2006 | Dower et al. |
| 7,057,026 B2 | 6/2006 | Barnes et al. |
| 7,057,031 B2 | 6/2006 | Olejnik et al. |
| 7,074,597 B2 | 7/2006 | Ju |
| 7,078,499 B2 | 7/2006 | Odedra et al. |
| 7,105,300 B2 | 9/2006 | Parce et al. |
| 7,270,951 B1 | 9/2007 | Stemple et al. |
| 7,279,563 B2 | 10/2007 | Kwiatkowski |
| 7,329,496 B2 | 2/2008 | Dower et al. |
| 7,345,159 B2 | 3/2008 | Ju |
| 7,393,533 B1 | 7/2008 | Crotty et al. |
| 7,414,116 B2 | 8/2008 | Milton et al. |
| 7,427,673 B2 | 9/2008 | Balasubramanian et al. |
| 7,459,275 B2 | 12/2008 | Dower et al. |
| 7,566,537 B2 | 7/2009 | Balasubramanian et al. |
| 7,622,279 B2 | 11/2009 | Ju |
| 7,635,578 B2 | 12/2009 | Ju et al. |
| 7,713,698 B2 | 5/2010 | Ju et al. |
| 7,785,790 B1 | 8/2010 | Church et al. |
| 7,790,869 B2 | 9/2010 | Ju et al. |
| 7,883,869 B2 | 2/2011 | Ju et al. |
| 7,982,029 B2 | 7/2011 | Ju et al. |
| 8,088,575 B2 | 1/2012 | Ju et al. |
| 8,158,346 B2 | 4/2012 | Balasubramanian et al. |
| 8,298,792 B2 | 10/2012 | Ju et al. |
| 8,399,188 B2 | 3/2013 | Zhao et al. |

(56) References Cited

U.S. PATENT DOCUMENTS

| | | | |
|---|---|---|---|
| 8,796,432 | B2 | 8/2014 | Ju et al. |
| 8,889,348 | B2 | 11/2014 | Ju |
| 9,115,163 | B2 | 8/2015 | Ju et al. |
| 9,133,511 | B2 | 9/2015 | Ju et al. |
| 2002/0012966 | A1 | 1/2002 | Shi et al. |
| 2002/0168642 | A1 | 11/2002 | Drukier |
| 2003/0008265 | A1 | 1/2003 | Fischer |
| 2003/0014096 | A1 | 1/2003 | Burkhart |
| 2003/0022225 | A1 | 1/2003 | Monforte et al. |
| 2003/0027140 | A1 | 2/2003 | Ju et al. |
| 2003/0044871 | A1 | 3/2003 | Cutsforth et al. |
| 2003/0054360 | A1 | 3/2003 | Gold et al. |
| 2003/0099972 | A1 | 5/2003 | Olejnik et al. |
| 2003/0166282 | A1 | 9/2003 | Brown et al. |
| 2003/0180769 | A1 | 9/2003 | Metzker |
| 2003/0186256 | A1 | 10/2003 | Fischer |
| 2003/0190680 | A1 | 10/2003 | Rothschild et al. |
| 2003/0198982 | A1 | 10/2003 | Seela et al. |
| 2004/0096825 | A1 | 5/2004 | Chenna et al. |
| 2005/0032081 | A1 | 2/2005 | Ju et al. |
| 2005/0170367 | A1 | 8/2005 | Quake et al. |
| 2005/0239134 | A1 | 10/2005 | Gorenstein et al. |
| 2006/0003352 | A1 | 1/2006 | Lipkin et al. |
| 2006/0057565 | A1 | 3/2006 | Ju et al. |
| 2006/0105461 | A1 | 5/2006 | Tom-Moy et al. |
| 2006/0160081 | A1 | 7/2006 | Milton et al. |
| 2006/0240439 | A1 | 10/2006 | Smith et al. |
| 2006/0252038 | A1 | 11/2006 | Ju et al. |
| 2007/0166705 | A1 | 7/2007 | Milton et al. |
| 2009/0088332 | A1 | 4/2009 | Ju et al. |
| 2009/0240030 | A1 | 9/2009 | Ju et al. |
| 2009/0298072 | A1 | 12/2009 | Ju |
| 2009/0325154 | A1 | 12/2009 | Ju et al. |
| 2010/0159531 | A1 | 6/2010 | Gordon et al. |
| 2010/0323350 | A1 | 12/2010 | Gordon et al. |
| 2011/0014611 | A1 | 1/2011 | Ju et al. |
| 2011/0124054 | A1 | 5/2011 | Olejnik et al. |
| 2012/0052489 | A1 | 3/2012 | Gordon et al. |
| 2012/0142006 | A1 | 6/2012 | Ju et al. |
| 2012/0156680 | A1 | 6/2012 | Ju et al. |
| 2013/0264207 | A1 | 10/2013 | Ju et al. |
| 2014/0093869 | A1 | 4/2014 | Ju et al. |
| 2014/0206553 | A1 | 7/2014 | Ju et al. |
| 2014/0315191 | A1 | 10/2014 | Ju et al. |
| 2014/0377743 | A1 | 12/2014 | Ju et al. |
| 2015/0037788 | A1 | 2/2015 | Ju |
| 2015/0080232 | A1 | 3/2015 | Ju et al. |

FOREIGN PATENT DOCUMENTS

| | | |
|---|---|---|
| DE | 20122767.3 U1 | 8/2008 |
| DE | 112007002932.3 | 8/2015 |
| EP | 0251786 B1 | 11/1994 |
| EP | 0995804 A2 | 4/2000 |
| EP | 1182267 A1 | 2/2002 |
| EP | 1291354 A2 | 3/2003 |
| EP | 0808320 B1 | 4/2003 |
| EP | 1337541 B1 | 3/2007 |
| EP | 1218391 B1 | 4/2007 |
| EP | 1790736 A2 | 5/2007 |
| EP | 0992511 B1 | 3/2009 |
| EP | 2209911 B1 | 10/2013 |
| GB | 2000 0013276 | 6/2000 |
| GB | 2001 0029012 | 12/2001 |
| GB | 2446083 | 3/2011 |
| GB | 2446084 | 3/2011 |
| GB | 2457402 | 9/2011 |
| WO | WO 89/09282 | 10/1989 |
| WO | WO 89/10977 | 11/1989 |
| WO | WO 89/11548 | 11/1989 |
| WO | WO 90/13666 | 11/1990 |
| WO | WO 91/06678 | 5/1991 |
| WO | WO 92/10587 | 6/1992 |
| WO | WO 93/05183 | 3/1993 |
| WO | WO 93/12340 | 10/1993 |
| WO | WO 93/21340 | 10/1993 |
| WO | WO 94/14972 | 7/1994 |
| WO | WO 96/07669 | 3/1996 |
| WO | WO 96/23807 | 8/1996 |
| WO | WO 96/27025 | 9/1996 |
| WO | WO 97/08183 | 3/1997 |
| WO | WO 97/27317 | 7/1997 |
| WO | WO 97/35033 | 9/1997 |
| WO | WO 98/30720 | 7/1998 |
| WO | WO 98/33939 | 8/1998 |
| WO | WO 98/44151 | 10/1998 |
| WO | WO 99/05315 | 2/1999 |
| WO | WO 99/49082 | 9/1999 |
| WO | WO 99/57321 | 11/1999 |
| WO | WO 00/02895 | 1/2000 |
| WO | WO 00/06770 | 2/2000 |
| WO | WO 00/09753 | 2/2000 |
| WO | WO 00/15844 | 3/2000 |
| WO | WO 00/18956 | 4/2000 |
| WO | WO 00/21974 | 4/2000 |
| WO | WO 00/50172 | 6/2000 |
| WO | WO 00/50642 | 8/2000 |
| WO | WO 00/53805 | 9/2000 |
| WO | WO 00/53812 | 9/2000 |
| WO | WO 00/70073 | 11/2000 |
| WO | WO 01/16375 | 3/2001 |
| WO | WO 01/23610 | 4/2001 |
| WO | WO 01/25247 | 4/2001 |
| WO | WO 01/27625 A | 4/2001 |
| WO | WO 01/32390 | 5/2001 |
| WO | WO 01/57248 | 8/2001 |
| WO | WO 01/57249 | 8/2001 |
| WO | WO 01/92284 | 12/2001 |
| WO | WO 02/02813 | 1/2002 |
| WO | WO 02/21098 | 3/2002 |
| WO | WO 02/22883 A1 | 3/2002 |
| WO | WO 02/29003 | 4/2002 |
| WO | WO 02/72892 | 9/2002 |
| WO | WO 02/79519 A1 | 10/2002 |
| WO | WO 02/88381 | 11/2002 |
| WO | WO 02/88382 | 11/2002 |
| WO | WO 03/02767 | 1/2003 |
| WO | WO 03/20968 | 3/2003 |
| WO | WO 03/46387 | 6/2003 |
| WO | WO 03/48178 | 6/2003 |
| WO | WO 03/85135 | 10/2003 |
| WO | WO 04/18493 | 3/2004 |
| WO | WO 04/18497 | 3/2004 |
| WO | WO 04/55160 | 7/2004 |
| WO | WO 06/73436 | 7/2006 |
| WO | WO 06/97320 A2 | 9/2006 |
| WO | WO 07/62105 | 5/2007 |
| WO | WO 2013/154999 | 10/2013 |
| WO | WO 2013/191793 | 12/2013 |
| WO | WO 2014/144883 | 9/2014 |
| WO | WO 2014/144898 | 9/2014 |
| WO | WO 2015/148802 | 10/2015 |

OTHER PUBLICATIONS

Aug. 19, 2013 Petition 1 of 2 for Inter Partes Review of U.S. Pat. No. 7,566,537, issued Jul. 28, 2009.

Aug. 30, 2013 Revised Petition 1 of 2 for Inter Partes Review of U.S. Pat. No. 7,566,537, issued Jul. 28, 2009.

Exhibit 1011, filed Aug. 19, 2013 in connection with IPR2013-00517: Aug. 16, 2013 Declaration of Dr. Bruce Branchaud.

Exhibit 1012, filed Aug. 19, 2013 in connection with IPR2013-00517: Excerpts from the Mar. 20, 2013 Deposition Transcript of Dr. Xiaohai Liu.

Feb. 13, 2014 Decision of Institution of Inter Partes Review IPR2013-00517.

May 5, 2014 Patent Owner Response in connection with IPR2013-00517.

Exhibit 2005, filed May 5, 2014 in connection with IPR2013-00517: IBS's Answer, Affirmative Defenses & Counterclaims to Illumina, Inc. and Illumina Cambridge Ltd.'s Second Amended Counterclaims to Amended Complaint, *Columbia v. Illumina*, No. 12-CV-00376 (D. Del).

(56) References Cited

OTHER PUBLICATIONS

Exhibit 2006, filed May 5, 2014 in connection with IPR2013-00517: Excerpts from file history of U.S. Appl. No. 13/305,415, filed Nov. 28, 2011, Gordon et al.
Exhibit 2010, filed May 5, 2014 in connection with IPR2013-00517: Excerpts from prosecution history of U.S. Pat. No. 7,566,537, issued Jul. 28, 2009, Barnes et al.
Exhibit 2011, filed May 5, 2014 in connection with IPR2013-00517: May 5, 2014 Declaration of Floyd Romesberg, Ph.D.
Exhibit 2013, filed May 5, 2014 in connection with IPR2013-00517: Ranganathan et al., "Facile Conversion of Adenosine into New 2'-Substituted-2'-Deoxy-Arabinofuranosyladenine Derivatives: Stereospecific Syntheses of 2'-Azido-2'-Deoxy-, 2'-Amino-2'-Deoxy-, and 2'-Mercapto-2'-Deoxy-β-D- Arabinofuranosyladenines" Tetrahedron Letters 45:4341-44 (1978).
Exhibit 2014, filed May 5, 2014 in connection with IPR2013-00517: Mungall et al., "Use of the Azido Group in the Synthesis of 5' Terminal Aminodeoxythymidine Oligonucleotides" J. Org. Chem., 40:1659-1662 (1975).
Exhibit 2016, filed May 5, 2014 in connection with IPR2013-00517: Pilard et al., "A Stereospecific Synthesis OF (±), α-Conhydrine and (+) β-Conhydrine)" Tet. Lett., 25:1555-1556. (1984).
Exhibit 2017, filed May 5, 2014 in connection with IPR2013-00517: "Synthesis of a Novel Stable $GM_3$-Lactone Analogue as Hapten for a Possible Immunization against Cancer" Tietze et al., Agnew. Chem. Int. Ed., 36:1615, 1616 (1997).
Exhibit 2018, filed May 5, 2014 in connection with IPR2013-00517: Kit, "Deoxyribonucleic Acids" Annual Rev. Biochem, 32:43 (1963).
Exhibit 2019, filed May 5, 2014 in connection with IPR2013-00517: Canard et al., "Catalytic editing properties of DNA polymerases" PNAS USA 92:10859 (1995).
Exhibit 2020, filed May 5, 2014 in connection with IPR2013-00517: The Merck Index, p. 9815 (entry for Triphenylphosphine) ($13^{th}$ Edition, 2001).
Exhibit 2021, filed May 5, 2014 in connection with IPR2013-00517: Lee et al., "Unwinding of double-stranded DNA helix by dehydration" PNAS 78:2838-42 (1981).
Exhibit 2022, filed May 5, 2014 in connection with IPR2013-00517: Christensen et al., "Specific Chemical Synthesis of Ribonucleoside O-Benzyl Ethers" J. Am. Chem. Soc., 37:3398 (1972).
Exhibit 2023, filed May 5, 2014 in connection with IPR2013-00517: Watkins et al., "Synthesis of Oligodeoxyribonucleotides Using N-Benzyloxycarbonyl-Blocked Nucleosides", J. Am. Chem. Soc. 104:5702-08 (1982).
Exhibit 2025, filed May 5, 2014 in connection with IPR2013-00517: Yoshimoto et al., "Tris(2,4,6-trimethoxyphenyl)phosphine (TTMPP): A Novel Catalyst for Selective Deacetylation" Chemistry Letters 30:934-35 (2001).
Exhibit 2026, filed May 5, 2014 in connection with IPR2013-00517: Chapter 3 of Protective Groups in Organic Synthesis (Theodora W. Greene & Peter G. M. Wuts eds., John Wiley & Sons, Inc. 3rd ed. 1999) (1991).
Exhibit 2027, filed May 5, 2014 in connection with IPR2013-00517: Bentley et al., "Accurate whole human genome sequencing using reversible terminator chemistry" Nature 456:53-59 (2008).
Exhibit 2029, filed May 5, 2014 in connection with IPR2013-00517: Shendure et al., "Advanced Sequencing Technologies: Methods and Goals" Nature Reviews Genetics, 5:335-44 (2004).
Exhibit 2039, filed May 5, 2014 in connection with IPR2013-00517: Transcript of Apr. 8, 2014 Deposition of Bruce Branchaud, Ph.D.
Exhibit 2044, filed May 5, 2014 in connection with IPR2013-00517: Excerpts of Transcript of Mar. 20, 2013 Deposition of Dr. Xiaohai Liu in *Columbia v. Illumina*, 12-cv-376 (D. Del).
Exhibit 2047, filed May 5, 2014 in connection with IPR2013-00517: Ruparel et al., "Design and synthesis of a 3-O-allyl photocleavable fluorescent nucleotide as a reversible terminator for DNA sequencing by synthesis" PNAS 102:5932-5937 (2005).
Exhibit 2050, filed May 5, 2014 in connection with IPR2013-00517: Mardis, "A decade's perspective on DNA sequencing technology" Nature 470:198-203 (2011).

Exhibit 2051, filed May 5, 2014 in connection with IPR2013-00517: Meng et al., "Design and Synthesis of a Photocleavable Fluorescent Nucleotide 3'-O-Allyl-dGTP-PC-Bodipy-FL-510 as a Reversible Terminator for DNA Sequencing by Synthesis" J. Org. Chem 71:3248-52 (2006).
Exhibit 2052, filed May 5, 2014 in connection with IPR2013-00517: Bi et al., "Design and Synthesis of a Chemically Cleavable Fluorescent Nucleotide, 3'-O-Allyl-dGTP-allyl-Bodipy-FL-510, as a Reversible Terminator for DNA Sequencing by Synthesis" J Am Chem Soc, 128:2542-43 (2006).
Exhibit 2053, filed May 5, 2014 in connection with IPR2013-00517: Meng, "Tandem Aldol-Allylation Reactions Promoted by Strained Silacycles and Design and Synthesis of Modified Fluorescent Nucleotides for DNA Sequencing by Synthesis", Student Thesis (2006).
Exhibit 2054, filed May 5, 2014 in connection with IPR2013-00517: Wu et al., "3'-O-modified nucleotides as reversible terminators for pyrosequencing" PNAS, 104:16462-67 (2007).
Exhibit 2055, filed May 5, 2014 in connection with IPR2013-00517: Kim, "Four-Color DNA Sequencing by Synthesis on a Chip Using Cleavable Fluorescent Nucleotide Reversible Terminators", Student Thesis (2008).
Exhibit 2056, filed May 5, 2014 in connection with IPR2013-00517: Wu, "Molecular Engineering of Novel Nucleotide Analogues for DNA Sequencing by Synthesis", Student Thesis (2008).
Exhibit 2057, filed May 5, 2014 in connection with IPR2013-00517: Zhang, "Development of New DNA Sequencing Approaches and Investigation of Vision-related Proteins Using Synthetic Chemistry", Student Thesis (2008).
Exhibit 2058, filed May 5, 2014 in connection with IPR2013-00517: Guo et al., "Four-color DNA sequencing with 3'-O-modified nucleotide reversible terminators and chemically cleavable fluorescent dideoxynucleotides", PNAS 105:9145.
Exhibit 2059, filed May 5, 2014 in connection with IPR2013-00517: Guo, "Molecular Engineering of Novel Nucleotide Analogues for DNA Sequencing and Analysis", Student Thesis (2009).
Exhibit 2060, filed May 5, 2014 in connection with IPR2013-00517: Yu, "Novel Strategies to Increase Read Length and Accuracy for DNA Sequencing by Synthesis", Student Thesis (2010).
Exhibit 2062, filed May 5, 2014 in connection with IPR2013-00517: Qui, "Novel Molecular Engineering Approaches for Genotyping and DNA Sequencing", Student Thesis (2010).
Exhibit 2073, filed May 5, 2014 in connection with IPR2013-00517: Kraevskii et al., "Substrate Inhibitors of DNA Biosynthesis", Molecular Biology 21:25-29 (1987).
Exhibit 2074, filed May 5, 2014 in connection with IPR2013-00517: Dantas et al., "Stannous chloride mediates single strand breaks in plasmid DNA through reactive oxygen species formation", Toxicology Ltrs. 110:129-36 (1999).
Exhibit 2077, filed May 5, 2014 in connection with IPR2013-00517: Burgess et al., "An Approach to Photolabile, Fluorescent Protecting Groups", J. Org. Chem 62:5165-68 (1997).
Petitioner Reply to Patent Owner Response, filed Jul. 28, 2014 in connection with IPR2013-00517.
Exhibit 1019, filed Jul. 28, 2014 in connection with IPR2013-00517: Ireland et al., Approach to the Total Synthesis of Chlorothricolide: Synthesis of (+)-19, 20-Dihydro-24-O-methylchlorothricolide, Methyl Ester, Ethyl Carbonate, 51 J. Org. Chem. 635 (1986).
Exhibit 1020, filed Jul. 28, 2014 in connection with IPR2013-00517: Gordon et al., Abstract, The Relationship of Structure to Effectiveness of Denaturing Agents for DNA, Biophysical Society 6th Annual Meeting (Washington, 1962).
Exhibit 1022, filed Jul. 28, 2014 in connection with IPR2013-00517: p. 295 from Mar. 20, 2003 deposition of Dr. Xiaohai Liu, *The Trustees of Columbia University and Intelligent Bio-Systems, Inc. v. Illumina*, 12-376 (GMS) (D. Del.).
Exhibit 1025, filed Jul. 28, 2014 in connection with IPR2013-00517: Transcript, Jul. 8, 2014 Deposition of Floyd Romesberg, Ph.D.
Exhibit 1026, filed Jul. 28, 2014 in connection with IPR2013-00517: Transcript, Jul. 15, 2014 Deposition of Kevin Burgess, Ph. D.

(56) References Cited

OTHER PUBLICATIONS

Exhibit 1030, filed Jul. 28, 2014 in connection with IPR2013-00517: Patent prosecution excerpt from file history of U.S. Pat. No. 7,566,537 (U.S. Appl. 11/301,578).
Exhibit 1031, filed Jul. 28, 2014 in connection with IPR2013-00517: Second Declaration of Dr. Bruce Branchaud in Support of Intelligent Bio-Systems, Inc.'s Reply to Illumina's Patent Owner Response.
Exhibit 1032, filed Jul. 28, 2014 in connection with IPR2013-00517: Gololobov and Kasukhin, Recent advances in the Staudinger reaction, Tetrahedron 48:1353-1406 (1992).
Exhibit 1034, filed Jul. 28, 2014 in connection with IPR2013-00517: Saxon and Bertozzi, Cell Surface Engineering by a Modified Staudinger Reaction, Science 287:2007-2010 (2000).
Exhibit 1036, filed Jul. 28, 2014 in connection with IPR2013-00517: Faucher and Grand-Maitre, tris(2-Carboxyethyl)phosphine (TCEP) for the Reduction of Sulfoxides, Sulfonylchlorides, N-Oxides, and Azides, Synthetic Communications 33:3503-3511 (2003).
Exhibits 1037 and 1038, filed Jul. 28, 2014 in connection with IPR2013-00517: Knouzi et al., Reductions of Azides by Triphenylphosphine in the presence of water: a General and chemoselective method of access to primary amines, Bull. Soc. Chim. Fr., 1-12 (1985), and translation.
Exhibit 1041, filed Jul. 28, 2014 in connection with IPR2013-00517: Mag and Engels, Synthesis and selective cleavage of oligodeoxyribonucleotides containing non-chiral internucleotide phosphoramidate linkages, Nucleic Acids Research 15:5973-5988 (1989).
Exhibit 1043, filed Jul. 28, 2014 in connection with IPR2013-00517: Chang and Bollum, Molecular biology of terminal transferase, CRC Critical Reviews in Biochemistry 21:27-52 (1986).
Exhibit 1044, filed Jul. 28, 2014 in connection with IPR2013-00517: Chen, DNA polymerases drive DNA sequencing-by-synthesis technologies: both past and present, Frontiers in Microbiology, vol. 5, Article 305, 1-11 (2014).
Exhibit 1046, filed Jul. 28, 2014 in connection with IPR2013-00517: Declaration of Dr. Michael Metzker in Suppoert of Intelligent Bio-Systems, Inc's Reply to Illumina's Patent Owner Response.
Exhibit 1047, filed Jul. 28, 2014 in connection with IPR2013-00517: Lebreton et al., Structure-Immunosuppressive Activity Relationships of New Analogues of 15-Deoxyspergualin. 2. Structural Modifications of the Spermidine Moiety, Journal of Medicinal Chemistry 42:4749-4763 (1999).
Exhibit 1048, filed Jul. 28, 2014 in connection with IPR2013-00517: Levine et al., The Relationship of Structure to the Effectiveness of Denaturing Agents for Deoxyribonucleic Acid, Biochemistry 2:168-175 (1963).
Exhibit 1049, filed Jul. 28, 2014 in connection with IPR2013-00517: Efimov et al., An azidomethyl protective group in the synthesis of oligoribonucleotides by the phosphotriester method, 35:250-253 (2009).
Exhibit 1050, filed Jul. 28, 2014 in connection with IPR2013-00517: Kirby, A new method for the isolation of deoxyribonucleic acids: Evidence of the nature of bonds between deoxyribonucleic acids and proteins, Biochemical Journal 66:495-504 (1957).
Exhibit 1051, filed Jul. 28, 2014 in connection with IPR2013-00517: Bentley et al., Accurate whole human genome sequencing using reversible terminator chemistry. Nature 456:53 (2008)—Supplementary Information.
Petitioner Motion to Exclude Evidence, filed Sep. 2, 2014 in connection with IPR2013-00517.
Patent Owner Motion to Exclude Evidence, filed Sep. 2, 2014 in connection with IPR2013-00517.
Patent Owner Motion for Observations on the Cross-Examination Testimony of Bruce Branchaud, Ph.D. and Michael Metzker, Ph.D., filed Sep. 2, 2014 in connection with IPR2013-00517.
Exhibit 2139, filed Sep. 2, 2014 in connection with IPR2013-00517: Metzker, "Sequencing Technologies—The Next Generation" Nature Reviews Genetics, 11:31-46 (2010).
Exhibit 2140, filed Sep. 2, 2014 in connection with IPR2013-00517: Tsai et al., "Versatile and Efficient Synthesis of a New Class of Aza-Based Phosphinic Amide Ligands via Unusual P-C Cleavage" Helvetica Chimica Acta, 89:3007-3017 (2006).
Exhibit 2141, filed Sep. 2, 2014 in connection with IPR2013-00517: Treinin, General and Theoretical Aspects, Chapter 1 (pp. 1-55) in The Chemistry of the Azido Group (Saul Patai, Ed.) (1971).
Exhibit 2142, filed Sep. 2, 2014 in connection with IPR2013-00517: Hanlon, "The Importance of London Dispersion Forces in the Maintenance of the Deoxyribonucleic Acid Helix" Biochemical and Biophysical Research Communications, 23:861-867 (1966).
Exhibit 2144, filed Sep. 2, 2014 in connection with IPR2013-00517: "Phenol," in The Merck Index, pp. 1299-1300 (13th Ed., 2001).
Exhibit 2146, filed Sep. 2, 2014 in connection with IPR2013-00517: Metzker, "Emerging technologies in DNA sequencing" Genome Research, 15:1767-1776, (2005).
Exhibit 2147, filed Sep. 2, 2014 in connection with IPR2013-00517: Gardner et al., "Rapid incorporation kinetics and improved fidelity of a novel class of 3'-OH unblocked reversible terminators" Nucleic Acids Research, 40:7404-7415 (2012).
Exhibit 2148, filed Sep. 2, 2014 in connection with IPR2013-00517: Lander et al., "Initial sequencing and analysis of the human genome" Nature, 409:860-921 (2001).
Exhibit 2150, filed Sep. 2, 2014 in connection with IPR2013-00517: Aldrich, Fine Chemicals catalogue, p. 1337 (1986).
Exhibit 2151, filed Sep. 2, 2014 in connection with IPR2013-00517: Sebastian et al., "Dendrimers with N,N-Disubstituted Hydrazines as End Groups, Useful Precursors for the Synthesis of Water-Soluble Dendrimers Capped with Carbohydrate, Carboxylic or Boronic Acid Derivatives" Tetrahedron, 56:6269-6277 (2000).
Exhibit 2152, filed Sep. 2, 2014 in connection with IPR2013-00517: Reardon et al., "Reduction of 3'-Azido-3'-deoxythymidine (AZT) and AZT Nucleotides by Thiols" The Journal of Biological Chemistry, 269:15999-16008 (1994).
Exhibit 2154, filed Sep. 2, 2014 in connection with IPR2013-00517: Transcript, Aug. 12, 2014 Deposition of Michael L. Metzker, Ph.D.
Exhibit 2155, filed Sep. 2, 2014 in connection with IPR2013-00517: Transcript, Aug. 26, 2014 Deposition of Bruce P. Branchaud, Ph.D.
Petitioner Opposition to Patentee Motion to Exclude Evidence, filed Sep. 15, 2014 in connection with IPR2013-00517.
Patentee Opposition to Petitioner Motion to Exclude Evidence, filed Sep. 15, 2014 in connection with IPR2013-00517.
Patentee's Reply to Petitioner's Opposition to Patentee Motion to Exclude Evidence, filed Sep. 22, 2014 in connection with IPR2013-00517.
Petitioner's Reply to Patentee's Opposition to Motion to Amend, filed Sep. 22, 2014 in connection with IPR2013-00517.
Patentee Demonstratives for Oral Hearing, filed Oct. 3, 2014 in connection with IPR2013-00517.
Petitioner Demonstratives for Oral Hearing, filed Oct. 3, 2014 in connection with IPR2013-00517.
Transcript of Oct. 10, 2014 Oral Hearing, entered Feb. 2, 2015 in connection with IPR2013-00517.
Feb. 11, 2015 Final Written Decision in connection with IPR2013-00517.
U.S. Appl. No. 10/227,131, filed Aug. 23, 2002, Barnes et al.
Jan. 29, 2013 Petition for Inter Partes Review of U.S. Pat. No. 7,057,026.
Feb. 7, 2013 Revised Petition for Inter Partes Review of U.S. Pat. No. 7,057,026.
May 1, 2013 Preliminary Response under 37 C.F.R. 42.107 in connection with IPR2013-00128.
Jul. 29, 2013 Decision on Petition for Inter Partes Review in connection with IPR2013-00128.
Oct. 24, 2013 Patent Owner Motion to Amend the Patent in connection with IPR2013-00128.
Exhibit 1006, filed Jan. 29, 2013 in connection with IPR2013-00128: Beckman Coulter CEQTM 2000 DNA Analysis System User's Guide, Jun. 2000.
Exhibit 1010, filed Jan. 29, 2013 in connection with IPR2013-00128: Kamal, Tetrahedron Letters 40(2):371-372, 1999.
Exhibit 1011, filed Jan. 29, 2013 in connection with IPR2013-00128: Jung, J.C.S. Chem. Comm. (7):315-316, 1978.

(56) References Cited

OTHER PUBLICATIONS

Exhibit 1015, filed Jan. 29, 2013 in connection with IPR2013-00128: Jan. 28, 2013 Declaration of Dr. Bruce Branchaud.
Exhibit 1016, filed Jan. 29, 2013 in connection with IPR2013-00128: Excerpts from the '026 Patent File History.
Exhibit 1020, filed Jan. 29, 2013 in connection with IPR2013-00128: Transcript of Initial Conference Call Held on Aug. 29, 2013.
Exhibit 2001, filed May 1, 2013 in connection with IPR2013-00128: *The Trustees of Columbia University in the City of New York v. Illumina, Inc.*, 1:12-cv-00376-GMS—Columbia's Amended Complaint.
Exhibit 2002, filed May 1, 2013 in connection with IPR2013-00128: *The Trustees of Columbia University in the City of New York v. Illumina, Inc.*, 1:12-cv-00376-GMS—Columbia's Amended Answer.
Exhibit 2003, filed May 1, 2013 in connection with IPR2013-00128: *The Trustees of Columbia University in the City of New York v. Illumina, Inc.*, 1:12-cv-00376-GMS—IBS's Responses to Illumina's Requests for Admission.
Exhibit 2004, filed May 1, 2013 in connection with IPR2013-00128: *The Trustees of Columbia University in the City of New York v. Illumina, Inc.*, 1:12-cv-00376-GMS—Columbia's Responses to Illumina's Requests for Admission.
Exhibit 2006, filed Oct. 24, 2013 in connection with IPR2013-00128: Green & Wuts, Protective Groups in Organic Synthesis, excerpts from "Protection From the Hydroxyl Group," (1999).
Exhibit 2007, filed Oct. 24, 2013 in connection with IPR2013-00128: Katagiri et al., "Selective Protection of the Primary Hydroxyl Groups of Oxetanocin A," Chem. Pharm. Bull. 43:884-886 (1995).
Exhibit 1029, filed Jan. 24, 2014 in connection with IPR2013-00128: Jan. 9, 2014 Substitute Declaration of Floyd Romesberg, Ph.D.
Exhibit 2012, filed Oct. 24, 2013 in connection with IPR2013-00128: Oct. 3, 2013 Deposition Transcript of Bruce Branchaud, Ph.D.
Exhibit 2016, filed Oct. 24, 2013 in connection with IPR2013-00128: Ruby, Methods in Enzymology (1990).
Exhibit 2025, filed Oct. 24, 2013 in connection with IPR2013-00128: U.S. Pat. No. 7,057,026 file history.
Exhibit 1025, filed Jan. 24, 2014 in connection with IPR2013-00128: Substitute Eric Vermaas Declaration, Dec. 20, 2013.
Exhibit 1021, filed Dec. 23, 2013 in connection with IPR2013-00128: Excerpts from Protective Groups in Organic Synthesis (Theodora W. Greene & Peter G. M. Wuts eds., John Wiley & Sons, Inc. 3rd ed. 1999) (1991).
Exhibit 1022, filed Dec. 23, 2013 in connection with IPR2013-00128: Signed Deposition Transcript of Dr. Bruce Branchaud on Oct. 3, 2013.
Jan. 24, 2014 Intelligent Bio-Systems Opposition to Illumina's Motion to Amend in connection with IPR2013-00128.
Exhibit 1030, filed Jan. 24, 2014 in connection with IPR2013-00128: Dawson et al., "Affinity Isolation of Transcriptionally Active Murine Erythroleukemia Cell DNA Using a Cleavable Biotinylated Nucleotide Analog" J. of Biol. Chem., 264, 12830-37 (1989).
Exhibit 1032, filed Jan. 24, 2014 in connection with IPR2013-00128: Mitra et al., "Fluorescent in situ sequencing on polymerase colonies" Analytical Biochem. 320, 55-65 (2003).
Exhibit 1033, filed Jan. 24, 2014 in connection with IPR2013-00128: Deposition of Floyd Romesberg, Ph.D., from Jan. 14, 2014.
Exhibit 1034, filed Jan. 24, 2014 in connection with IPR2013-00128: 1999/2000 Pierce Chemical Company catalog (1999).
Exhibit 1035, filed Jan. 24, 2014 in connection with IPR2013-00128: Second Declaration of Dr. Bruce Branchaud, dated Jan. 23, 2014.
Exhibit 1039, filed Jan. 24, 2014 in connection with IPR2013-00128: Excerpts from the file history of European Patent Application No. 02781434.2.
Exhibit 1041, filed Jan. 24, 2014 in connection with IPR2013-00128: Lukesh et al., "A Potent, Versatile Disulfide-Reducing Agent from Aspartic Acid" J. Am. Chem. Soc., 134, 4057-59 (2012).
Exhibit 1042, filed Jan. 24, 2014 in connection with IPR2013-00128: Klausner, "Dupont's DNA Sequencer Uses New Chemistry" Nat. Biotech., 5, 1111-12 (1987).
Exhibit 1043, filed Jan. 24, 2014 in connection with IPR2013-00128: Murakami et al., "Structure of a *Plasmodium yoelii* gene-encoded protein homologous to the Ca2+-ATPase of rabbit skeletal muscle sarcoplasmic reticulum" J. Cell Sci., 97, 487-95 (1990).
Exhibit 1044, filed Jan. 24, 2014 in connection with IPR2013-00128: Letsinger et al., "2,4-Dinitrobenzenesulfenyl as a Blocking Group for Hydroxyl Functions in Nucleosides" J. Org. Chem., 29, 2615-2618 (1964).
Exhibit 1045, filed Jan. 24, 2014 in connection with IPR2013-00128: Handlon & Oppenheimer, "Thiol Reduction of 3'-Azidothymidine to 3'-Aminothymidine: Kinetics and Biomedical Implications" Pharm. Res., 5, 297-99 (1988).
Exhibit 1047, filed Jan. 24, 2014 in connection with IPR2013-00128: Burns et al., "Selective Reduction of Disulfides by Tris(2-carboxyethyl)phosphine" J. Org. Chem., 56, 2648-50.
Feb. 19, 2014 Substitute Motion to Amend Under 37 C.F.R. §42.121.
Exhibit 2009, filed Feb. 19, 2014 in connection with IPR2013-00128: Substitute Declaration of Floyd Romesberg, Ph.D., in Support of Patent Owner's Motion to Amend.
Exhibit 2028, filed Feb. 19, 2014 in connection with IPR2013-00128: Substitute Declaration of Eric Vermaas Accompanying Patent Owner's Motion to Amend.
Feb. 24, 2014 Patent Owner Illumina's Reply to Petitioner's Opposition to Illumina's Motion to Amend.
Exhibit 2029, filed Feb. 24, 2014 in connection with IPR2013-00128: Supplementary information for Ex. 1032 (Mitra et al., Analytical Biochem. 320, 55-65, 2003).
Exhibit 2032, filed Feb. 24, 2014 in connection with IPR2013-00128: ScanArray Express Line of Microarray Scanners—Brochure.
Exhibit 2034, filed Feb. 24, 2014 in connection with IPR2013-00128: Feb. 11, 2014 Second Deposition Transcript of Bruce Branchaud, Ph.D.
Exhibit 2037, filed Feb. 24, 2014 in connection with IPR2013-00128: Mullis et al., "Specific Synthesis of DNA in Vitro via a Polymerase-Catalyzed Chain Reaction," pp. 335-350, in Methods in Enzymology, vol. 155, Recombinant DNA, Part F, ed. Wu, Academic Press, Inc., San Diego (1987).
Exhibit 2038, filed Feb. 24, 2014 in connection with IPR2013-00128: Brown et al., "Modern machine-aided methods of oligodeoxyribonucleotide synthesis," pp. 1-11; and Ruth, "Oligodeoxynucleotides with reporter groups attached to the base," p. 255, in Oligonucleotides and Analogues, A Practical Approach, ed. Eckstein, Oxford Univ. Press, New York (1991).
Exhibit 2039, filed Feb. 24, 2014 in connection with IPR2013-00128: Dawson and Herman et al., "Affinity isolation of active murine erythroleukemia cell chromatin: Uniform distribution of ubiquitinated histone H2A between active and inactive fractions", Journal of Cellular Biochemistry 46:166-173 (1991).
Exhibit 2040, filed Feb. 24, 2014 in connection with IPR2013-00128: Rigas et al., "Rapid plasmid library screening using RecA-coated biotinylated probes," PNAS USA 83:9591-9595 (1986).
Exhibit 2041, filed Feb. 24, 2014 in connection with IPR2013-00128: U.S. Pat. No. 4,888,274, issued Dec. 19, 1989 to Radding et al.
Exhibit 2042, filed Feb. 24, 2014 in connection with IPR2013-00128: Westheimer et al., "Why nature chose phosphates" Science 235:1173-1178 (1987).
Mar. 18, 2014 Petitioner's Motion to Exclude in connection with IPR2013-00128 (Exhibit 82).
Exhibit 1048, filed Mar. 18, 2014 in connection with IPR2013-00128: Petitioner's Objections to Patentee's Exhibits submitted with its Reply to Petitioner's Opposition to Patentee's Motion to Amend (Exhibit 83).
Mar. 18, 2014 Patentee's Motion to Exclude Petitioner's Evidence in connection with IPR2013-00128.
Demonstrative Exhibits of Intelligent Bio-Systems, Inc., for Apr. 23, 2014 hearing, filed Apr. 18, 2014 in connection with IPR2013-00128.

(56) References Cited

OTHER PUBLICATIONS

Demonstrative Exhibits of Illumina for Apr. 23, 2014 hearing, filed Apr. 21, 2014 in connection with IPR2013-00128.
May 22, 2014 Record of Apr. 23, 2014 Oral Hearing in connection with IPR2013-00128.
Jul. 25, 2014 Final Written Decision in connection with IPR2013-00128.
Amendment filed Apr. 28, 2015 in response to Office Action, dated Jan. 28, 2015 in connection with U.S. Appl. No. 13/951,269.
Jun. 15, 2015 Notice of Allowance in connection with U.S. Appl. No. 13/951,269.
Oct. 3, 2012 Petition for Inter Partes Review of U.S. Pat. No. 8,088,575.
Oct. 3, 2012 Motion to Waive Page Limit and Proposed Petition in connection with Petition for Inter Partes Review of U.S. Pat. No. 8,088,575.
Jan. 7, 2013 Preliminary Response under 37 C.F.R. 42.107 in connection with IPR2013-00011.
Mar. 12, 2013 Decision on Petition for Inter Partes Review in connection with IPR2013-00011.
Mar. 26, 2013 Request for Reconsideration in connection with IPR2013-00011.
Mar. 26, 2013 Request for Rehearing under 37 C.F.R. 42.71 of Decision to Institute Inter Partes Review in connection with IPR2013-00011.
Apr. 26, 2013 Opposition to Request for Reconsideration (Rehearing) Under 37 C.F.R. 42.71.(C) in connection with IPR2013-00011.
May 10, 2013 Decision on Request for Rehearing in connection with IPR2013-00011.
Jun. 25, 2013 Motion to Amend Under 37 C.F.R. 42.121 in connection with IPR2013-00011.
Aug. 30, 2013 Substitute Patent Owner Response Under 37 C.F.R. 42.120 in connection with IPR2013-00011.
Sep. 27, 2013 Petitioner Opposition to Motion to Amend in connection with IPR2013-00011.
Sep. 27, 2013 Petitioner Reply to Response to Petition in connection with IPR2013-00011.
Nov. 18, 2013 Substitute Patent Owner Reply on Motion to Amend in connection with IPR2013-00011.
Exhibit 1001, filed Oct. 3, 2012 in connection with IPR2013-00011: U.S. Pat. No. 8,088,575 issued Jan. 3, 2012 to Ju et al.
Exhibit 1021, filed Oct. 3, 2012 in connection with IPR2013-00011: Oct. 2, 2012 Declaration of George Weinstock Under Rule 37 C.F.R. §1.132.
Exhibit 1022, filed Oct. 3, 2012 in connection with IPR2013-00011: Excerpts of File History of U.S. Pat. No. 8,088,575.
Exhibit 1053, filed Sep. 27, 2013 in connection with IPR2013-00011: Sep. 27, 2013 Declaration of Kevin Burgess.
Exhibit 2033, filed Aug. 30, 2013 in connection with IPR2013-00011: Jun. 25, 2013 Substitute Declaration of Dr. George L. Trainor [redacted].
Nov. 12, 2013 Petitioner Motion to Exclude Evidence in connection with IPR2012-00007.
Nov. 12, 2013 Patent Owner Motion for Observations on the Cross-Examination Testimony of Kevin Burgess, Ph.D. in connection with IPR2012-00007.
Nov. 12, 2013 Patent Owner Motion to Exclude Evidence in connection with IPR2012-00007.
Nov. 26, 2013 Petitioner's Response to Motion for Observations in connection with IPR2013-00011.
Nov. 26, 2013 Patent Owner's Opposition to Petitioner's Motion to Exclude in connection with IPR2013-00011.
Nov. 26, 2013 Petitioner's Opposition to Motion to Exclude in connection with IPR2013-00011.
Dec. 3, 2013 Petitioner Reply to Patent Owner's Opposition to Motion to Exclude in connection with IPR2013-00011.
Dec. 3, 2013 Patent Owner Reply on Motion to Exclude in connection with IPR2013-00011.
Mar. 6, 2014 Final Written Decision in connection with IPR2013-00011.
Aug. 19, 2013 Petition 2 of 2 for Inter Partes Review of U.S. Pat. No. 7,566,537, issued Aug. 19, 2013.
Exhibit 1015, filed Aug. 19, 2013 in connection with IPR2013-00518: Aug. 16, 2013 Declaration of Dr. Bruce Branchaud.
Exhibit 1016, filed Aug. 19, 2013 in connection with IPR2013-00518: Excerpts from the '537 Patent File History.
Exhibit 1017, filed Aug. 19, 2013 in connection with IPR2013-00518: Excerpts from the file history of European Patent Application No. 02781434.2.
Feb. 13, 2014 Decision of Institution of Inter Partes Review IPR2013-00518.
May 5, 2014 Patentee Request for Adverse Judgment in IPR2013-00518.
May 6, 2014 Decision of Adverse Judgment in IPR2013-00518.
U.S. Appl. No. 09/266,187, filed Mar. 10, 1999, Stemple et al.
Sep. 16, 2012 Petition for Inter Partes Review of U.S. Pat. No. 7,713,698, issued May 11, 2010.
Sep. 16, 2012 Motion to Waive Page Limit and Proposed Petition in connection with Petition for Inter Partes Review of U.S. Pat. No. 7,713,698, issued May 11, 2010.
Dec. 20, 2012 Preliminary Response under 37 C.F.R. 42.107 in connection with IPR2012-00006.
Mar. 12, 2013 Decision on Petition for Inter Partes Review in connection with IPR2012-00006.
Mar. 26, 2013 Request for Reconsideration in connection with IPR2012-00006.
Apr. 26, 2013 Opposition to Request for Reconsideration (Rehearing) Under 37 C.F.R. 42.71.(C) in connection with IPR2012-00006.
May 10, 2013 Decision on Request for Rehearing in connection with IPR2012-00006.
Aug. 30, 2013 Substitute Patent Owner Response Under 37 C.F.R. 42.120 in connection with IPR2012-00006.
Aug. 30, 2013 Substitute Patent Owner Motion to Amend Under 37 C.F.R. 42.121 in connection with IPR2012-00006.
Sep. 27, 2013 Petitioner Opposition to Motion to Amend in connection with IPR2012-00006.
Sep. 27, 2013 Petitioner Reply to Response to Petition in connection with IPR2012-00006.
Nov. 18, 2013 Patent Owner Substitute Reply on Motion to Amend in connection with IPR2012-00006.
Exhibit 1003, filed Sep. 16, 2012 in connection with IPR2012-00006: Prober et al. (1987), "A System for Rapid DNA Sequencing with Fluorescent Chain-Terminating Dideoxynucleotides", Science vol. 238, Oct. 16, 1987, pp. 336-341.
Exhibit 1021, filed Sep. 16, 2012 in connection with IPR2012-00006: Sep. 15, 2012 Declaration of George Weinstock Under Rule 37 C.F.R. §1.132.
Exhibit 1022, filed Sep. 16, 2012 in connection with IPR2012-00006: Excerpts of File History of U.S. Pat. No. 7,713,698.
Exhibit 1025, filed Apr. 30, 2013 in connection with IPR2012-00006: Columbia's Amended Complaint from *The Trustees of Columbia University in the City of New York v. Illumina, Inc.*, D. Del C.A. No. 12-376 (GMS), filed Apr. 11, 2012.
Exhibit 1026, filed Apr. 30, 2013 in connection with IPR2012-00006: Illumina's Answer to Amended Complaint from *The Trustees of Columbia University in the City of New York v. Illumina, Inc.* D. Del C.A. No. 12-376 (GMS), filed Dec. 21, 2012.
Exhibit 1030, filed Jun. 18, 2013 in connection with IPR2012-00006: Rosenblum et al., "New Dye-Labeled Terminators for Improved DNA Sequencing Patterns," Nucleic Acid Research, 1997, vol. 25, No. 22, pp. 4500-4504.
Exhibit 1034, filed Jun. 18, 2013 in connection with IPR2012-00006: Jun. 8, 2013 Videotaped Deposition Transcript of George M. Weinstock, Ph.D.
Exhibit 1036, filed Sep. 27, 2013 in connection with IPR2012-00006: "Next Generation Genomics: World Map of High-throughput Sequencers," Sep. 1, 2013.
Exhibit 1039, filed Sep. 27, 2013 in connection with IPR2012-00006: Videotaped Deposition Transcript of Dr. Xiaohai Liu, Mar. 20, 2013.
Exhibit 1040, filed Sep. 27, 2013 in connection with IPR2012-00006: Excerpt from videotaped Deposition Transcript of George M. Weinstock, Ph.D., Jun. 8, 2013.

(56) References Cited

OTHER PUBLICATIONS

Exhibit 1041, filed Sep. 27, 2013 in connection with IPR2012-00006: Seela et al., "Oligonucleotide Duplex Stability Controlled by the 7-Substituents of 7-Deazaguanine Bases," Bioorganic & Medical Chemistry Letters, vol. 5, No. 24, pp. 3049-3052, 1995.
Exhibit 1042, filed Sep. 27, 2013 in connection with IPR2012-00006: Ramzaeva et al., "123. 7-Deazaguanine DNA: Oligonucleotides with Hydrophobic or Cationic Side Chains," Helvetica Chimica Acta, vol. 80, pp. 1809-1822, 1997.
Exhibit 1043, filed Sep. 27, 2013 in connection with IPR2012-00006: Ramzaeva et al., "88. 7-Substituted 7-Deaza-2'-deoxyguanosines: Regioselective Halogenation of Pyrrolo[2,3-d]pyrimidine Nucleosides," Helvetica Chimica Acta, vol. 78, pp. 1083-1090, 1995.
Exhibit 1044, filed Sep. 27, 2013 in connection with IPR2012-00006: Seela et al., "Duplex Stability of Oligonucleotides Containing 7-Substituted 7-Deaza- and 8-Aza-7-Deazapurine Nucleosides," Nucleosides & Nucleotides, 16(7-9), pp. 963-966, 1997.
Exhibit 1045, filed Sep. 27, 2013 in connection with IPR2012-00006: Burgess et al., "Syntheses of Nucleosides Designed for Combinatorial DNA Sequencing," Chemistry—A European Journal, vol. 5, No. 3, pp. 951-960, 1999.
Exhibit 1049, filed Sep. 27, 2013 in connection with IPR2012-00006: Jan. 28, 2013 Declaration of Dr. Bruce P. Branchaud in Support of Petition for Inter Partes Review of U.S. Pat. No. 7,057,026.
Exhibit 1050, filed Sep. 27, 2013 in connection with IPR2012-00006: Lee et al., "DNA sequencing with dye-labeled terminators and T7 DNA polymerase: effect of dyes and dNTPs on incorporation of dye-terminators and probability analysis of termination fragments," Nucleic Acids Research, vol. 20, No. 10, pp. 2471-2483, 1992.
Exhibit 1051, filed Sep. 27, 2013 in connection with IPR2012-00006: http://www.answers.com/topic/incubate, Accessed Sep. 27, 2013.
Exhibit 1052, filed Sep. 27, 2013 in connection with IPR2012-00006: http://en.wikipedia.org/wiki/Fluorenylmethyloxycarbonyl_chloride, Accessed Sep. 27, 2013.
Exhibit 1053, filed Sep. 27, 2013 in connection with IPR2012-00006: Sep. 27, 2013 Declaration of Kevin Burgess.
Exhibit 1054, filed Sep. 27, 2013 in connection with IPR2012-00006: Fuji, et al., "An Improved Method for Methoxymethylation of Alcohols under Mild Acidic Conditions," Synthesis—The Journal of Synthetic Organic Chemisty, pp. 276-277, Apr. 1975.
Exhibit 2006, filed Apr. 26, 2013 in connection with IPR2012-00006: Dower patent with highlights.
Exhibit 2013, filed Jun. 24, 2013 in connection with IPR2012-00006: Oct. 2, 2012 Declaration of George Weinstock Under 37 CFR 1.132 (Exhibit 1021 in IPR2013-00011).
Exhibit 2014, filed Jun. 24, 2013 in connection with IPR2012-00006: Petition for Inter Partes Review of U.S. Pat. No. 8,088,575 (Paper 4 in IPR2013-00011).
Exhibit 2015, filed Jun. 24, 2013 in connection with IPR2012-00006: Metzker et al. (1994) Termination of DNA synthesis by novel 3'-modified-deoxyribonucleoside 5'-triphosphates. Nucleic Acids Res. 22:4259-4267.
Exhibit 2016, filed Jun. 24, 2013 in connection with IPR2012-00006: Wu et al. (2007) Termination of DNA synthesis by N6-alkylated, not 3'-O-alkylated, photocleavable 2'-deoxyadenosine triphosphates. Nucleic Acids Res. 35:6339-6349.
Exhibit 2017, filed Jun. 24, 2013 in connection with IPR2012-00006: Sep. 15, 2012 Declaration of George Weinstock Under 37 CFR 1.132 (Exhibit 1021 in IPR2012-00007).
Exhibit 2019, filed Jun. 24, 2013 in connection with IPR2012-00006: Definition of "DNA microarray.". http://en/wikipedia.org/wiki/DNA_microarry.
Exhibit 2020, filed Jun. 24, 2013 in connection with IPR2012-00006: Brettin et al. (2005) Expression capable library for studies of Neisseria gonorrhoeae, version 1.0 BMC Microbiology. 5:50.
Exhibit 2021, filed Jun. 24, 2013 in connection with IPR2012-00006: George M. Weinstock, Handbook of Molecular Microbial Ecology, vol. 1—Chapter 18: The Impact of Next-Generation Sequencing Technologies on Metagenomics 141-147 Frans J. de Bruijn ed., John Wiley & Sons, Inc. (2011).
Exhibit 2023, filed Jun. 24, 2013 in connection with IPR2012-00006: Sep. 16, 2012 Petition for Inter Partes Review of U.S. Pat. No. 7,790,869 (Paper 5 in IPR2012-00007).
Exhibit 2024, filed Jun. 24, 2013 in connection with IPR2012-00006: Maxam and Gilbert (1977) A new method for sequencing DNA, Proc. Natl. Acad. Sci. USA. 74:560-564.
Exhibit 2025, filed Jun. 24, 2013 in connection with IPR2012-00006: Sanger et al. (1977) DNA sequencing with chain-terminating inhibitors, Proc. Natl. Acad. Sci. USA. 74:5463-5467.
Exhibit 2026, filed Jun. 24, 2013 in connection with IPR2012-00006: Pennisi (2000) DOE Team Sequences Three Chromosomes, Science. 288:417-419.
Exhibit 2027, filed Jun. 24, 2013 in connection with IPR2012-00006: Welch and Burgess (1999) Synthesis of Fluorescent, Photolabile 3'-O-Protected nucleoside Triphosphates for the Base Addition Sequencing Scheme, nucleosides & Nucleotides 18:197-201.
Exhibit 2028, filed Jun. 24, 2013 in connection with IPR2012-00006: Hyman (1998) A New Method of Sequencing DNA, Analytical Biochemistry 174:423-436.
Exhibit 2030, filed Jun. 24, 2013 in connection with IPR2012-00006: Canard and Sarfati (1994) DNA polymerase fluorescent substrates with reversible 3'-tags, Gene. 1481-6.
Exhibit 2032, filed Jun. 24, 2013 in connection with IPR2012-00006: Sarfati et al. (1987) Synthesis of Fluorescent or Biotinylated Nucleoside Compounds, Tetrahedron Letters. 43:3491-3497.
Exhibit 2033, filed Aug. 30, 2013 in connection with IPR2012-00006: Jun. 25, 2013 Substitute Declaration of Dr. George L. Trainor [redacted].
Exhibit 2034, filed Jun. 25, 2013 in connection with IPR2012-00006: Jingyue Ju et. al. (2006) Four-color DNA sequencing by synthesis using cleavable fluorescent nucleotide reversible terminators, Proceedings of the National Academy of Sciences. 103: 19635-19640.
Exhibit 2035, filed Jun. 25, 2013 in connection with IPR2012-00006: Batista et al. (2008) PRG-1 and 21U-RNAs Interact to Form the piRNA Complex Required for Fertility in C. elegans. Molecular Cell 31:1-12.
Exhibit 2036, filed Jun. 25, 2013 in connection with IPR2012-00006: Form 7 Review Context and Analysis, Biomedical Engineering and Research to Aid Persons with Disabilities Programs Dec. 19-20, 2000 Panel Review, Fluorescence Imaging Chip System for Massive Parallel DNA Sequencing. Proposal No. BES-0097793.
Exhibit 2037, filed Jun. 25, 2013 in connection with IPR2012-00006: Oct. 1, 2006 Request for opinion on manuscript by J. Ju et. al., Proceedings of National Academy of Sciences, U.S.A.
Exhibit 2038, filed Jun. 25, 2013 in connection with IPR2012-00006: Correspondence between George Rupp, Chancellor, Columbia University and Richard T. Schlossberg, President, The David and Lucile Packard Foundation (2001).
Exhibit 2039, filed Jun. 25, 2013 in connection with IPR2012-00006: The David and Lucile Packard Foundation, Packard Fellowships for Science and Engineering, http://www.packard.org/what-wefund/conservation-and-science/packard-fellowships-for-science-andengineering/ (last visited Jun. 25, 2013).
Exhibit 2040, filed Jun. 25, 2013 in connection with IPR2012-00006: "Chemistry for Next-Generation Sequencing." http://www.illumina.com/technology/sequencing_technology.ilmn.
Exhibit 2041, filed Jun. 25, 2013 in connection with IPR2012-00006: Chiang et al. (2010) Mammalian microRNAs: experimental evaluation of novel and previously annotated genes, Genes & Dev. 24:992, 993.
Exhibit 2042, filed Jun. 25, 2013 in connection with IPR2012-00006: Seo et al. (2004) Photocleavable fluorescent nucleotides for DNA sequencing on a chip constructed by site-specific coupling chemistry, Proc. Natl Acad. Sci. 101(15):5488-5493.
Exhibit 2043, filed Jun. 25, 2013 in connection with IPR2012-00006: Curriculum vitae of Mr. Raymond S. Sims.

(56) References Cited

OTHER PUBLICATIONS

Exhibit 2044, filed Jun. 25, 2013 in connection with IPR2012-00006: Prior Testimony of Mr. Raymond S. Sims.
Exhibit 2045, filed Jun. 25, 2013 in connection with IPR2012-00006: Documents reviewed by Mr. Raymond S. Sims in this Proceeding.
Exhibit 2052, filed Jun. 25, 2013 in connection with IPR2012-00006: Gary Schroth Proof of Chiang Paper.
Exhibit 2074, filed Jun. 25, 2013 in connection with IPR2012-00006: Information about Dr. Ju's intellectual property sent to Illumina.
Exhibit 2090, filed Jun. 26, 2013 in connection with IPR2012-00006: IPR Default Protective Order.
Exhibit 2091, filed Jun. 26, 2013 in connection with IPR2012-00006: Declaration of Raymond S. Sims.
Exhibit 2092, filed Oct. 10, 2013 in connection with IPR2012-00006: Rough Transcript of the Sep. 4, 2013 deposition of Dr. George L. Trainor.
Exhibit 2093, filed Oct. 1, 2013 in connection with IPR2012-00006: Excerpt from Protective Groups in Organic Synthesis, 3rd Ed. (Theodora W. Greene and Peter G.M. Wuts ed., John Wiley & Sons, Inc. 1999).
Exhibit 2094, filed Oct. 1, 2013 in connection with IPR2012-00006: Final transcript of the Sep. 4-6, 2013 deposition of Dr. George L. Trainor.
Exhibit 2095, filed Oct. 1, 2013 in connection with IPR2012-00006: Final transcript of the Sep. 3, 2013 deposition of Raymond S. Sims.
Nov. 12, 2013 Petitioner Motion to Exclude Evidence in connection with IPR2012-00006.
Exhibit 1056, filed Nov. 19, 2013 in connection with IPR2012-00006: Videotaped Deposition Transcript of Kevin Burgess, Ph.D., Oct. 28, 2013, signed with errata.
Nov. 12, 2013 Patent Owner Motion for Observations on the Cross-Examination Testimony of Kevin Burgess, Ph.D. in connection with IPR2012-00006.
Nov. 12, 2013 Patent Owner Motion to Exclude Evidence in connection with IPR2012-00006.
Exhibit 2099, filed Nov. 12, 2013 in connection with IPR2012-00006: Welch, M., et al (2005) Corrigenda to Syntheses of Nucleosides Designed for Combinatorial DNA Sequencing Chem. Eur.J., 1999, 951-960. Published in Chem. Eur. J, 2005, 11, 7136-7145.
Exhibit 2100, filed Nov. 12, 2013 in connection with IPR2012-00006: Welch, M (1999) "Base Additions Sequencing Scheme (BASS) and Studies Toward New Sequencing Methodologies." PhD. Dissertation, Texas A&M University.
Exhibit 2101, filed Nov. 12, 2013 in connection with IPR2012-00006: Lu and Burgess (2006) "A Diversity Oriented Synthesis of 3'-O-modified nucleoside triphosphates for DNA 'Sequencing by Synthesis'." Bioorganic & Medicinal Chemistry Letters, 16, 3902-3905.
Exhibit 2102, filed Nov. 12, 2013 in connection with IPR2012-00006: Advanced Sequencing Technology Awards 2004. http://www.genome.gov/12513162 (accessed Oct. 14, 2013).
Exhibit 2103, filed Nov. 12, 2013 in connection with IPR2012-00006: Welch and Burgess (2006) Erratum to Synthesis of Fluorescent, Photolabile 3'-O-Protected Nucleoside Triphosphates for the Base Addition Sequencing Scheme, Nucleosides & Nucleotides,18:197-201. Published in Nucleosides, Nucleotides and Nucleic Acids, 25:1, 119.
Nov. 26, 2013 Petitioner Response to Motion for Observations in connection with IPR2012-00006.
Nov. 26, 2013 Patent Owner Opposition to Petitioner's Motion to Exclude in connection with IPR2012-00006.
Nov. 26, 2013 Petitioner Opposition to Motion to Exclude in connection with IPR2012-00006.
Dec. 3, 2013 Petitioner Reply to Patent Owner's Opposition to Motion to Exclude in connection with IPR2012-00006.
Dec. 3, 2013 Patent Owner Reply on Motion to Exclude in connection with IPR2012-00006.
Exhibit 2105, filed Dec. 15, 2013 in connection with IPR2012-00006: Columbia's Demonstratives Under 42.70(b) for Dec. 17, 2013 Oral Hearing in connection with IPR2012-00006, IPR2012-00007, and IPR2013-00011.
Exhibit 1057, filed Dec. 16, 2013 in connection with IPR2012-00006: Illumina's Invalidity Demonstratives for Final Hearing Dec. 17, 2013 in connection with IPR2012-00006, IPR2012-00007, and IPR2013-00011.
Feb. 10, 2014 Record of Dec. 17, 2013 Oral Hearing in connection with IPR2012-00006, IPR2012-00007, and IPR2013-00011.
Mar. 6, 2014 Final Written Decision in connection with IPR2012-00006.
U.S. Appl. No. 12/804,025, filed Jul. 13, 2010, Balasubramanian et al.
May 4, 2013 Petition for Inter Partes Review of U.S. Pat. No. 8,158,346, issued Apr. 17, 2012.
Aug. 5, 2013 Patent Owner Preliminary Response to Petition for Inter Partes Review of U.S. Pat. No. 8,158,246, issued Apr. 17, 2012.
Exhibit 1011, filed May 4, 2013 in connection with IPR2013-00266: May 3, 2013 Declaration of Dr. Bruce Branchaud.
Exhibit 1012, filed May 4, 2013 in connection with IPR2013-00266: Excerpts from the '346 Patent File History.
Exhibit 1013, filed May 4, 2013 in connection with IPR2013-00266: Excerpts from the file history of European Patent Application No: 02781434.2.
Oct. 28, 2013 Decision Instituting Inter Partes Review in connection with IPR2013-00266.
Dec. 30, 2013 Illumina Motion to Amend Under 37 C.F.R. §42.121 in connection with IPR2013-00266.
Exhibits 2004, 2005, and 2028, filed Dec. 30, 2013 in connection with IPR2013-00266: Floyd Romesburg Declaration, CV, and List of Documents Considered by Romesburg.
Exhibit 2021, filed Dec. 30, 2013 in connection with IPR2013-00266: Bystrom, Branchaud et al., "ATP Analogs with Non-transferable Groups in the g Position As Inhibitors of Glycerol Kinase" Bioorganic & Medicinal Chemistry Letters, 7:2613-2616 (1997).
Exhibit 2022, filed Dec. 30, 2013 in connection with IPR2013-00266: Pages from Handbook of Reagents for Organic Synthesis: Reagents for Silicon-Mediated Organic Synthesis (Philip L. Fuchs, ed.) (2011).
Exhibit 2023, filed Dec. 30, 2013 in connection with IPR2013-00266: Eric Vermaas Declaration—Redacted version.
Exhibit 2024, filed Dec. 30, 2013 in connection with IPR2013-00266: Excerpts from Oct. 3, 2013 Bruce Branchaud Deposition Transcript in IPR 2013-00128.
Petitioner's Feb. 28, 2014 Opposition to Patentee Motion to Amend in connection with IPR2013-00266.
Exhibit 1021, filed Feb. 28, 2014 in connection with IPR2013-00266: Second Declaration of Dr. Bruce Branchaud in support of Intelligent Bio-Systems, Inc.'s Opposition to Illumina's Motion to Amend, from Feb. 28, 2014.
Exhibit 1022, filed Feb. 28, 2014 in connection with IPR2013-00266: Deposition of Floyd Romesberg, Ph.D., from Jan. 14, 2014.
Exhibit 1029, filed Feb. 28, 2014 in connection with IPR2013-00266: Deposition of Eric Vermaas from Jan. 13, 2014.
Exhibit 1035, filed Feb. 28, 2014 in connection with IPR2013-00266: Excerpts from Protective Groups in Organic Synthesis (Theodora W. Greene & Peter G. M. Wuts eds., John Wiley & Sons, Inc. 3rd ed. 1999) (1991).
Exhibit 1038, filed Feb. 28, 2014 in connection with IPR2013-00266: Zavgorodny et al., "1-Alkylthioalkylation of Nucleoside Hydroxyl Functions and Its Synthetic Applications: A New Versatile Method in Nucleoside Chemistry" 32 Tetrahedron Letters 7593 (1991).
Mar. 21, 2014 Patent Owner's Reply to Petitioner's Opposition to Patent Owner's Motion to Amend in connection with IPR2013-00266.
Exhibit 2030, filed Mar. 21, 2014 in connection with IPR2013-00266: Mar. 11, 2014 Bruce Branchaud Deposition Transcript.

(56) References Cited

OTHER PUBLICATIONS

Exhibit 2032, filed Mar. 21, 2014 in connection with IPR2013-00266: Excerpts from Feb. 11, 2014 Bruce Branchaud Deposition Transcript in related IPR2013-00128.
Exhibit 2043, filed Mar. 21, 2014 in connection with IPR2013-00266: English translation of Loubinoux et al., "Protection of Phenols by The Azidomethylene Group Application to The Synthesis of Unstable Phenols" Tetrahedron, 44:6055-6064 (1988).
Exhibit 2044, filed Mar. 21, 2014 in connection with IPR2013-00266: Excerpts from Oct. 3, 2013 Bruce Branchaud Deposition Transcript in related Inter Partes Review IPR2013-00128.
Exhibit 2045, filed Mar. 21, 2014 in connection with IPR2013-00266: Welch et al., "Syntheses of Nucleosides Designed for Combinatorial DNA Sequencing" Chem. Eur. J., 5:951-960 (1999).
Exhibit 2046, filed Mar. 21, 2014 in connection with IPR2013-00266: Welch et al., Corrigenda to "Syntheses of Nucleosides Designed for Combinatorial DNA Sequencing" Chem. Eur. J., 11:7145 (2005).
Exhibit 2047, filed Mar. 21, 2014 in connection with IPR2013-00266: Wu et al., "Termination of DNA synthesis by $N^6$-alkylated, not 3'-0-alkylated, photocleavable 2'-deoxyadenosine triphosphates", Nucleic Acids Research 35:6339-6349 (2007).
Exhibit 2048, filed Mar. 21, 2014 in connection with IPR2013-00266: Taylor et al., "Rise per base pair in helices of double-stranded rotavirus RNA determined by electron microscopy" Virus Research, 2:175-182 (1985).
Exhibit 2049, filed Mar. 21, 2014 in connection with IPR2013-00266: Watson et al., Molecular Biology of the Gene, Fifth Edition, Chapter 6 (2004).
Exhibit 2050, filed Mar. 21, 2014 in connection with IPR2013-00266: Shen et al., "RNA structure at high resolution" FASEB J., 9:1023-1033 (1995).
Exhibit 2051, filed Mar. 21, 2014 in connection with IPR2013-00266: Holtzman et al., "Electron microscopy of complexes of isolated acetylochine receptor, biotinyl-toxin, and avidin" Proc. Natl. Acad. Sci. USA, 79:310-314 (1982).
Exhibit 2052, filed Mar. 21, 2014 in connection with IPR2013-00266: Pugliese et al., "Three-dimensional Structure of the Tetragonal Crystal Form of Egg-white Avidin in its Functional Complex with Biotin at 2.7 Angstrom Resolution" Journal of Molecular Biology, 231:698-710 (1993).
Exhibit 2053, filed Mar. 21, 2014 in connection with IPR2013-00266: Fersht, "Fidelity of replication of phage φX174 DNA by DNA polymerase III holoenzyme: Spontaneous mutation by misincorporation" Proc. Natl. Acad. Sci. USA, 76:4946-4950 (1979).
Exhibit 2054, filed Mar. 21, 2014 in connection with IPR2013-00266: Fersht et al., "DNA polymerase accuracy and spontaneous mutation rates: Frequencies of purine-purine, purine-pyrimidine, and pyrimidine-pyrimidine mismatches during DNA replication" Proc. Natl. Acad. Sci. USA, 78:4251-4255 (1981).
Exhibit 2055, filed Mar. 21, 2014 in connection with IPR2013-00266: Bebenek et al., "Frameshift errors initiated by nucleotide misincorporation" Proc. Natl. Acad. Sci. USA, 87:4946-4950 (1990).
Exhibit 2056, filed Mar. 21, 2014 in connection with IPR2013-00266: Bebenek et al., "The Effects of dNTP Pool Imbalances on Frameshift Fidelity during DNA Replication" J. Biol. Chem., 267:3589-3596 (1992).
Exhibit 2057, filed Mar. 21, 2014 in connection with IPR2013-00266: Greene and Wuts, Protective Groups in Organic Synthesis, 3rd ed., Chapter 1 (1999).
Apr. 18, 2014 Petitioner Motion for Observations on the Cross-Examination Testimony of Dr. Romesberg, in connection with IPR2013-00266.
Apr. 18, 2014 Petitioner Motion to Exclude Evidence in connection with IPR2013-00266.
Exhibit 1042, filed Apr. 18, 2014 in connection with IPR2013-00266: Apr. 10, 2014 transcript of Deposition of Floyd Romesberg.
Apr. 18, 2014 Patentee Motion to Exclude Evidence in connection with IPR2013-00266.
May 2, 2014 Patentee Response to Petitioner Motion for Observations on Romesberg Testimony, in connection with IPR2013-00266.
Exhibit 1045, filed May 22, 2014 in connection with IPR2013-00266: Petitioner Demonstratives for May 28, 2014 Oral Hearing.
Exhibit 2060, filed May 22, 2014 in connection with IPR2013-00266: Patentee Demonstratives for May 28, 2014 Oral Hearing.
Transcript of May 28, 2014 Oral Hearing in IPR2013-00266, entered Jul. 8, 2014.
Oct. 28, 2014 Final Written Decision in connection with IPR2013-00266.
Office Action dated Sep. 21, 2007 in connection with U.S. Appl. No. 10/380,256.
Office Action dated Oct. 25, 2002 in connection with U.S. Appl. No. 09/972,364.
Office Action dated Mar. 14, 2003 in connection with U.S. Appl. No. 09/972,364.
Notice of Allowance dated Sep. 6, 2007 in connection with U.S. Appl. No. 10/702,203.
Office Action dated Jun. 24, 2008 in connection with U.S. Appl. No. 11/894,690.
Notice of Allowance dated Feb. 24, 2009 in connection with U.S. Appl. No. 11/894,690.
Office Action dated Jun. 5, 2009 in connection with U.S. Appl. No. 11/894,690.
Office Action dated Sep. 3, 2008 in connection with U.S. Appl. No. 11/894,808.
Notice of Allowance dated Mar. 23, 2009 in connection with U.S. Appl. No. 11/894,808.
Notice of Allowance and Fee(s) Due dated Apr. 2, 2010 in connection with U.S. Appl. No. 11/810,509.
Partial European Search Report dated Apr. 26, 2007 in connection with European Patent Application No. 07004522.4.
Extended European Search Report dated Jul. 18, 2007 in connection with European Patent Application No. 07004522.4.
Official Action dated Mar. 14, 2008 in connection with European Patent Application No. 07004522.4.
Communication Pursuant to Article 94(3) EPC issued Apr. 30, 2009, connection with counterpart European Patent Application No. 07004522.4.
International Search Report dated May 13, 2002 in connection with PCT/US01/31243.
Supplementary European Search Report dated Feb. 16, 2004 in connection with European Patent Application No. 01977533.
International Preliminary Examination Report dated Jun. 13, 2003 in connection with PCT/US01/31243.
Official Action dated Mar. 31, 2006 in connection with European Patent Application No. 01968905.8.
Official Action dated May 21, 2007 in connection with European Patent Application No. 01968905.8.
International Preliminary Examination Report dated Feb. 25, 2003 in connection with PCT/US01/28967.
Supplementary European Search Report dated Jun. 7, 2005 in connection with European Patent Application No. 01968905.
International Search Report dated Jan. 23, 2002 in connection with PCT/US01/28967.
Notification of Transmittal of International Search Report and the Written Opinion of the International Searching Authority, or the Declaration dated Sep. 9, 2008 in connection with International Application No. PCT/US06/24157.
Notification of Transmittal of International Search Report and Written Opinion, dated Feb. 6, 2008 in connection with International Application No. PCT/US06/42739.
Notification of Transmittal of International Search Report and Written Opinion, dated Nov. 23, 2007 in connection with International Application No. PCT/US06/42698.
Notification Concerning Transmittal of International Preliminary Report on Patentability (Including Written Opinion of the International Searching Authority) dated May 15, 2008 in connection with PCT/US2006/042698.
Notification of Transmittal of International Search Report and Written Opinion, dated Aug. 12, 2008 in connection with International Application No. PCT/US07/24646.

(56) References Cited

OTHER PUBLICATIONS

International Search Report issued by the International Searching Authority (ISA/US) dated Aug. 12, 2008 in connection with International Application No. PCT/US07/24646.
Notification Concerning Transmittal of International Preliminary Report on Patentability, dated Jun. 11, 2009 in connection with International Application No. PCT/US07/24646.
Office Action dated Oct. 3, 2012 in connection with U.S. Appl. No. 12/734,229.
Apr. 3, 2013 Response to Office Action dated Oct. 3, 2012 in connection with U.S. Appl. No. 12/734,229.
Office Action dated Oct. 1, 2013 in connection with U.S. Appl. No. 12/734,229.
Apr. 1, 2014 Response to Office Action dated Oct. 1, 2013 in connection with U.S. Appl. No. 12/734,229.
Office Action dated May 27, 2014 in connection with U.S. Appl. No. 12/734,229.
Oct. 27, 2014 Pre-Appeal Brief Request for Review in connection with U.S. Appl. No. 12/734,229.
Office Action dated Dec. 10, 2014 in connection with U.S. Appl. No. 12/734,229.
Mar. 10, 2015 Amendment in Response to Office Action dated Dec. 10, 2014 in connection with U.S. Appl. No. 12/734,229.
Apr. 6, 2015 Notice of Allowance in connection with U.S. Appl. No. 12/734,229.
International Search Report issued by the International Searching Authority (ISA/US) dated Jan. 30, 2009 in connection with International Application No. PCT/US2008/011913.
Written Opinion of the International Searching Authority issued by the International Searching Authority (ISA/US) dated Jan. 30, 2009 in connection with International Application No. PCT/US2008/011913.
Extendted European Search Report and Search Opinion dated Jul. 24, 2012 in connection with European Patent Application No. 08841439.6.
Feb. 20, 2013 Response to Communication under Rule 70 (2) and 70a (2) EPC dated Aug. 10, 2012 in connection with European Patent Application No. 08841439.6.
Apr. 1, 2014 Communication transmitting Extended European Search Report and European Search Opinion in connection with European Patent Application No. 13188731.7.
Oct. 28, 2014 Response to Apr. 1, 2014 Communication transmitting Extended European Search Report and European Search Opinion in connection with European Patent Application No. 13188731.7.
Office Action dated Sep. 18, 2012 in connection with U.S. Appl. No. 12/734,227.
Amendment filed Mar. 18, 2013 in response to Office Action dated Sep. 18, 2012 in connection with U.S. Appl. No. 12/734,227.
Notice of Allowance dated Apr. 26, 2013 in connection with U.S. Appl. No. 12/734,227.
Notice of Abandonment dated Sep. 30, 2013 in connection with U.S. Appl. No. 12/734,227.
Office Action dated Jan. 28, 2015 in connection with U.S. Appl. No. 13/951,269.
International Search Report issued by the International Searching Authority (ISA/US) dated Feb. 10, 2009 in connection with International Application No. PCT/US2008/011891.
Written Opinion of the International Searching Authority issued by the International Searching Authority (ISA/US) dated Feb. 10, 2009 in connection with International Application No. PCT/US2008/011891.
Supplementary European Search Report and European Search Opinion dated Dec. 17, 2013 in connection with European Patent Application No. 08839081.0.
Amendment filed Jul. 15, 2014 in response to Jan. 9, 2014 Communication Pursuant to Rules 70(2) and 70a(2) in connection with European Patent Application No. 08839081.0.
Communication under Rule 71(3) EPC issued Nov. 17, 2014 in connection with European Patent Application No. 08839081.0.
Supplementary European Search Report and European Search Opinion dated Jul. 21, 2015 in connection with European Patent Application No. 15165262.5.
International Search Report dated Sep. 26, 2003 in connection with PCT/US03/21818.
International Preliminary Examination Report dated Mar. 18, 2005 in connection with PCT/US03/21818.
Notification of Transmittal of International Search Report and Written Opinion, dated May 22, 2008 in connection with International Application No. PCT/US06/45180.
International Preliminary Report on Patentability dated Sep. 5, 2006 in connection with PCT/US05/06960.
International Search Report dated Oct. 29, 2007 in connection with PCT International Application No. PCT/US07/13559.
Supplementary European Search Report dated Feb. 9, 2007 in connection with European Patent Application No. 03764568.6.
Supplementary European Search Report dated Sep. 9, 2008 in connection with PCT International Application No. PCT/US05/06960.
International Search Report dated Sep. 18, 2002 in connection with PCT/US02/09752.
International Preliminary Examination Report dated Mar. 17, 2003 in connection with PCT/US02/09752.
Supplementary European Search Report dated May 25, 2005 in connection with European Patent Application No. 02728606.1.
Written Opinion of the International Searching Authority dated Oct. 27, 2005 in connection with PCT/US05/06960.
Written Opinion of the International Searching Authority dated Dec. 15, 2006 in connection with PCT/US05/13883.
International Search Report dated Jun. 8, 2004 in connection with PCT/US03/39354.
International Search Report dated Nov. 4, 2005 in connection with PCT/US05/06960.
International Search Report dated Dec. 15, 2006 in connection with PCT/US05/13883.
Bi, L., Kim D.H., and Ju, J. (2006) "Design and Synthesis of a Chemically Cleavable Fluorescent Nucleotide, 3'-O-Allyl-dGTP-allyl-Bodipy-FL-510, as a Reversible Terminator for DNA Sequencing by Synthesis" J. Am. Chem. Soc., 128:2542-2543.
Guo et al. (2008) "Four-Color DNA Sequencing With 3'-O-modified Nucletide Reversible Terminators and Chemically Cleavable Fluorescent Dideoxynucleotides", PNAS, 105:9145-9150.
Guo et al., (2010) "An Integrated System for DNA Sequencing by Synthesis Using Novel Nucleotide Analogues", Accounts of Chem. Res., 43:551-563.
Highlander, S.K. et al., Complete nucleotide sequence of a P2 family lysogenic bacteriophage, φMhal-PHL101, from Mannheimia haemolytica serotype A1, Virology, 350:79-89 (2006).
Ju, J. et al. (2006) "Four-color DNA Sequencing by Synthesis Using Cleavable Fluorescent Nucleotide Reversible Terminators," Proc. Natl. Acad. Sci. USA, 103(52):19635-40. Epub Dec. 14, 2006.
Metzker M.L. (2005) "Emerging Technologies in DNA Sequencing." Genome Res., 15:1767-1776.
Seo et al. (2005) "Four-Color DNA Sequencing by Synthesis on a Chip Using Photocleavable Fluorescent Nucleotides," PNAS 102(17):5926-5931.
Jun. 4, 2013 Petition for Inter Partes Review of U.S. Pat. No. 7,057,026.
Exhibit 1004, filed Jun. 4, 2013 in connection with IPR2013-00324: J. Meinwald, An Approach to the Synthesis of Pederin, 49 Pure and Appl. Chem. 1275 (1977).
Exhibit 1005, filed Jun. 4, 2013 in connection with IPR2013-00324: Takeshi Matsumoto et al., A Revised Structure of Pederin, 60 Tetrahedron Letters 6297 (1968).
Exhibit 1009, filed Jun. 4, 2013 in connection with IPR2013-00324: Jun. 4, 2013 Declaration of Dr. Bruce Branchaud.
Exhibit 1010, filed Jun. 4, 2013 in connection with IPR2013-00324: Excerpts from the '026 Patent File History.
Exhibit 1011, filed Jun. 4, 2013 in connection with IPR2013-00324: Excerpts from the file history of European Patent Application No. 02781434.2.
Nov. 21, 2013 Decision Denying Institution of Inter Partes Review of U.S. Pat. No. 7,057,026 in connection with IPR2013-00324.

(56) References Cited

OTHER PUBLICATIONS

Sep. 16, 2012 Petition for Inter Partes Review of U.S. Pat. No. 7,790,869.
Sep. 17, 2012 Motion to Waive Page Limit and Proposed Petition in connection with Petition for Inter Partes Review of U.S. Pat. No. 7,790,869.
Dec. 21, 2012 Preliminary Response under 37 C.F.R. 42.107 in connection with IPR2012-00007.
Mar. 12, 2013 Decision on Petition for Inter Partes Review in connection with IPR2012-00007.
Mar. 26, 2013 Request for Reconsideration in connection with IPR2012-00007.
Mar. 26, 2013 Request for Rehearing under 37 C.F.R. 42.71 of Decision to Institute Inter Partes Review in connection with IPR2012-00007.
Apr. 26, 2013 Opposition to Request for Reconsideration (Rehearing) Under 37 C.F.R. 42.71.(C) in connection with IPR2012-00007.
May 10, 2013 Decision on Request for Rehearing in connection with IPR2012-00007.
Aug. 30, 2013 Substitute Patent Owner Response Under 37 C.F.R. 42.120 in connection with IPR2012-00007.
Aug. 30, 2013 Substitute Patent Owner Motion to Amend Under 37 C.F.R. 42.121 in connection with IPR2012-00007.
Sep. 27, 2013 Petitioner Opposition to Motion to Amend in connection with IPR2012-00007.
Sep. 27, 2013 Petitioner Reply to Response to Petition in connection with IPR2012-00007.
Nov. 18, 2013 Substitute Patent Owner Reply on Motion to Amend in connection with IPR2012-00007.
Exhibit 1022, filed Sep. 16, 2012 in connection with IPR2012-00007: Excerpts of File History of U.S. Pat. No. 7,790,869.
Exhibit 1053, filed Sep. 27, 2013 in connection with IPR2012-00007: Sep. 27, 2013 Declaration of Kevin Burgess.
Exhibit 2001, filed Dec. 21, 2012 in connection with IPR2012-00007: Composition of a Nucleotide.
Exhibit 2033, filed Aug. 30, 2013 in connection with IPR2012-00007: Jun. 25, 2013 Substitute Declaration of Dr. George L. Trainor [redacted].
Nov. 26, 2013 Petitioner's Response to Motion for Observations in connection with IPR2012-00007.
Nov. 26, 2013 Patent Owner's Opposition to Petitioner's Motion to Exclude in connection with IPR2012-00007.
Nov. 26, 2013 Petitioner's Opposition to Motion to Exclude in connection with IPR2012-00007.
Dec. 3, 2013 Petitioner Reply to Patent Owner's Opposition to Motion to Exclude in connection with IPR2012-00007.
Dec. 3, 2013 Patent Owner Reply on Motion to Exclude in connection with IPR2012-00007.
Mar. 6, 2014 Final Written Decision in connection with IPR2012-00007.
Arbo et al. (1993) "Solid Phase Synthesis of Protected Peptides Using New Cobalt (III) Amine Linkers," Int. J. Peptide Protein Res. 42:138-154.
Axelrod, V.D. et al. (1978) "Specific termination of RNA polymerase synthesis as a method of RNA and DNA sequenceing," Nucleic Acids Res. 5(10):3549-3563.
Badman, E. R. et al. (2000) "Cylindrical Ion Trap Array with Mass Selection by Variation in Trap Dimensions," Anal. Chem. (2000) 72:3291-3297.
Badman, E. R. et al. (2000) "Cylindrical Ion Trap Array with Mass Selection by Variation in Trap Dimentions," Anal. Chem. 72:5079-5086.
Bai et al. (2003) "Photocleavage of a 2-nitrobenzyl Linker Bridging a Fluorophore to the 5' end of DNA," PNAS, vol. vol. 100, No. 2, pp. 409-413.
Bai, X., Kim, S., Li, Z., Turro, N.J. and Ju, J. (2004) "Design and Synthesis of Photocleavable Biotinylated Nucleotide for DNA Analysis by Mass Spectrometry," Nucleic Acids Research, 32(2):534-541.

Benson, S.C., Mathies, R.A., and Glazer, A.N. (1993) "Heterodimeric DNA-binding dyes designed for energy transfer: stability and applications of the DNA complexes," Nucleic Acids Res. 21:5720-5726.
Benson, S.C., Singh, P., and Glazer, A.N. (1993) "Heterodimeric DNA-binding designed for energy transfer: synthesis and spectroscopic properties," Nucleic Acids Res. 21:5727-5735.
Bergmann et al. (1995) "Allyl as Internucleotide Protecting Group in DNA Synthesis to be Cleaved Off by Ammonia," Tetrahedron, 51:6971-6976.
Bergseid M., Baytan A.R., Wiley J.P., Ankener W.M., Stolowitz, Hughs K.A., and Chestnut J.D. (2000) "Small-molecule base chemical affinity system for the purification of proteins," BioTechniques 29:1126-1133.
Braslavsky, I.; Herbert, B.; Kartalov, E.; et al. (2003) "Sequence information can be obtained from single DNA molecules." Proc. Natl. Acad. Sci. 100(7):3960-3964.
Brunckova, J. et al. (1994) "Intramolecular Hydrogen Atom Abstrction in Carbohydrates and Nucleosides: Inversion of an α- to β-Mannopyranoside and Generation of Thymidine C-4' Radicals." Tetrahdron Letters, vol. 35 pp. 6619-6622.
Buck, G.A. et al. (1999) "Design Strategies and Performance of Custom DNA Sequecing Primer," BioTechniques 27(3):528-536.
Burgess, K. et al. (1997) "Photolytic Mass Laddering for Fast Characterization of Oligomers on Single Resin Beads," J. Org. Chem. 62:5662-5663.
Buschmann et al. (1999) "The Complex Formation of alpha, omega—Dicarboxylic Acids and aplha,omega—Diols with Cucurbituril and alpha-Cyclodextrin," Acta Chim. Slov. 46(3):405-411.
Buschmann et al. (2003) "Spectroscopic Study and Evaluation of Red-Absorbing Fluorescent Dyes," Bioconjugate Chem., 14:195-204.
Canard, B. et al, (1994) "DNA polymerase fluorescent substrates with reversible 3'- tags," Gene, 148:1-6.
Canard, B. et al. (1995) "Catalytic editing properties of DNA polymerases," Proc. Natl. Acad. Sci. USA 92:10859-10863.
Caetano-Anolies (1994) "DNA Amplification Fingerprinting Using Arbitrary Mini-hairpin Oligonucleotide Primers." Nature Biotechnology, 12:619-623.
Caruthers, M.H. (1985) "Gene synthesis machines: DNA chemistry and its uses," Science 230:281-285.
Chee, M. et al. (1996) "Accessing genetic information with high density DNA arrays," Science 274:610-614.
Chen, X. and Kwok, P. Y. (1997) "Template-directed dye-terminator incorporation (TDI) assay: a homogeneous DNA diagnostic method based on fluorescence resonance energy transfer, " Nucleic Acids Res. 25:347-353.
Chiu, N.H., Tang, K., Yip, P., Braun, A., Koster, H., and Cantor, C.R. (2000) "Mass spectrometry of single-stranded restriction fragments captured by an undigested complementary sequence," Nucleic Acids Res. 28:E31.
Collins, F. S.; Morgan, M.; Patrinos, A. (2003) "The Human Genome Project: Lessons from Large-Scale Biology." Science, 300, pp. 286-290.
Crespo-Hernandez et al., (2000) "Part 1. Photochemical and Photophysical Studies of Guanine Derivatives; Intermediates Contributing to its Photodestruction Mechanism in Aqueous Solution and the Participation of the Electron Adduct," Photochemistry and Photobiology, 71(5):534-543.
Drmanac, S.; Kita, D.; Labat, I.; et al. (1998) "Accurate sequencing by hybridization for DNA diagnostics and individual genomics." Nat. Biotech., 16:54-58.
Edwards, J. et al. (2001) "DNA sequencing using biotinylated dideoxynucleotides and mass sprectrometry," Nucleic Acids Res. 29(21):1041-1046.
Elango, N. et al. (1983) "Amino Acid Sequence of Human Respiratory Syncytial Virus Nucleocapsid Protein," Nucleic Acids Research 11(17):5941-5951.
Fallahpour, R.A. (2000) "Photochemical and Thermal reactions of Azido~Oligopyridines: Diazepinones, a New Class of Metal-Complex Ligands," Helvetica Chimica Acta. 83:384-393.
Fei, Z. et al. (1998) "MALDI-TOF mass spectrometric typing of single nucleotide polymorphisms with mass-tagged ddNTPs," Nucleic Acids Research 26(11):2827-2828.

(56) References Cited

OTHER PUBLICATIONS

Finzi, L. et al. (1995) "Measurement of Lactose Repressor-Mediated Loop Formation and Breakdown in Single DNA Molecules," Science, 267:378-380.
Fu, D.J., Tang, K., Braun, A., Reuter, D., Darnhofer-Demar, B., Little, D.P., O'Donnell, M.J., Cantor, C.R., and Koster, H. (1998) "Sequencing exons 5 to 8 of the p53 gene MALDI-TOF mass spectrometry," Nat. Biotechnol. 16:381-384.
Gibson, K.J. et al. (1987) "Synthesis and Application of Derivatizable Olingonucleotides," Nucleic Acids Research, 15(16):6455-6467.
Godovikova, T.S. et al. (1999) "5-[3-(E)-(4-Azido-2,3,5,6,-tetrafluorobenzamido)propenyl-1]-2'deoxyuridine-5'-triphosphate Substitutes for Thymidine-5'triphosphate in the Polymerase Chain Reaction," Bioconjugate Chem., 10:529-537.
Green, T.W. et al. and Wuts, P.G.M. "Protective Groups in Organic Sythesis" 3rd ed. New York: John Wiley & Sons, Inc., 1999. 96-99, 190-191, 260-261, 542-543, and 750-751.
Griffin, T.J. et al. (1999) "Direct Genetic Analysis by Matrix-Assisted Laser Desorption/Ionization Mass Spectrometry," Proc. Nat. Acad. Sci. USA 96:6301-6306.
Guibé (1997) "Allylic Protecting Groups and Their Use in a Complex Environment Part I: Allylic Protection of Alcohols," Tetrahedron, 53:13509-13556.
Guibé (1996) "Allylic Protecting Groups and Their Use in a Complex Environment Part II: Allylic Protecting Groups and their Removal through Catalytic Palladium n-Allyl Methodology," Tetrahedron, 54:2967-3042.
Hacia J.G., Edgemon K., Sun B., Stern D., Fodor S.A., and Collins F.S. (1998) "Two Color Hybridization Analysis Using High Density Oligonucleotide Arrays and Energy Transfer Dyes," Nucleic Acids Res. 25:3865-6.
Haff L.A., et al. (1997) "Multiplex Genotyping of PCR Products with Mass Tag-Labeled Primers," Nucleic Acids Res. 25(18):3749-3750.
Hafliger, D. et al. (1997) "Seminested RT-PCR Systems for Small Round Structured Viruses and Detection of Enteric Viruses in Seafood," International Journal of Food Microbiology 37:27-36.
Hanshaw et al. (2004) "An Indicator Displacement System for Fluorescent Detection of Phosphate Oxyanions Under Physiological Conditions," Tetrahedron Letters, vol. 45, pp. 8721-8724.
Hayakawa et al. (1993) "O-Allyl Protection of Guanine and Thymine Residues in Oligodeoxyribonucletides," J. Org. Chem., 58:5551-5555.
Henner, W.D. et al. (1983) "Enzyme Action at 3' Termini of Ionizing Radiation-Induced DNA Strand Breaks," J. Biol. Chem. 258(24):15198-15205.
Hovinen et al. (1994) "Synthesis of 3'-O-(ω-Aminoalkoxymethyl) thymidine 5'-Triphosphates, Terminators of DNA Synthesis that Enable 3'-Labelling," J. Chem. Soc. Perkin Trans., 1:211-217.
Hu et al. (1999) "Optical Mapping of DNA Polymerase I Action and Products," BBRC, 254:466-473.
Huang, B.G. et al. "Synthesis and in vitro Antitumor Activity of Some Amino-deoxy 3-hexofuranosylpyrrolo [2, 3-d]pyrimidines." Carbohydrate Research, 1998, 308(3-4):319-328.
Huber et al. (1999) "Monitoring Solid Phase Synthesis By Infrared Spectroscopic Techniques." Analytica Chimica Acta, 393:213.
Hultman et al. (1989) "Direct Solid Phase Sequencing of Genomic and Plasmid DNA Using Magnetic Beads as Solid Support," Nucleic Acids Research 17(3):4937-4946.
Hyman, E.D., (1988) "A new method of sequencing DNA," Analytical Biochemistry 174:423-436.
Ikeda, K. et al. (1995) "A Non-Radioactive DNA Sequencing Method Using Biotinylated Dideoxynucleoside Triphosphates and Delta TTH DNA Polymerase," DNA Research 2(31):225-227.
Ireland, R.E. and Varney, M.D. (1986) "Approach to the total synthesis of chlorothricolide: synthesis of (±)-19.20-dihydro-24-O-methylchlorothricolide, methyl ester, ethyl carbonate," J. Org. CJiang-Baucom, F. et al. (1997) "DNA Typing of Human Leukocyte Antigen Sequence Polymorphisms by Peptide Nucleic Acid Probes and MALDI-TOF Mas Spectrometry," Anal. Che. 69:4894-4896.

Jiang-Baucom, P. et al. (1997) "DNA Typing of Human Leukocyte Antigen Sequence Polymorphisms by Peptide Nucleic Acid Probes and MALDI-TOF Mass Spectrometry," Anal. Chem. 69:4894-489.
Ju, J., Ruan C., Fuller, C.W., Glazer, A.N., and Mathies, R.A. (1995) "Fluorescence energy transfer dye-labeled primers for DNA sequencing and analysis," Proc. Natl. Acad. Sci. USA 92: 4347-4351.
Ju, J. et al. (1996) "Cassette Labeling for Facile Construction of Energy Transfer Fluorescent Primers," Nuc. Acids Res. 24(6):1144-1148.
Ju, J., Glazer, A.N., and Mathies, R.A. (1996) "Energy Transfer Primers: A new Fluorescence Labeling Paradigm for DNA Sequencing and Analysis," Nature Medicine 2:246-249.
Jurinke, C., van de Boom, D., Collazo, V., Luchow, A., Jacob, A., and Koster H. (1997) "Recovery of nucleic acids from immobilized biotin-streptavidin complexes using ammonium hydroxide and application in MALDI-TOF mass spectometry," Anal. Chem. 69:904-910.
Kamal, A., Laxman, E., and Rao, N.V. (1999) "A mild and rapid regeneration of alcohols from their allylic ethers by chlorotrimethylsilane/sodium iodide," Tetrahedron Lett 40:371-372.
Kan, C.W.; Doherty, E. A. S.; Barron, A. E. (2003) "A novel thermogelling matrix for microchannel DNA sequencing based on poly-N-alkoxyalkylacrylamide copolymers," Electrophoresis, 24, pp. 4161-4169.
Kasianowicz, J.J., Brandin, E., Branton, D. and Deamer, D.W. (1996) "Characterization of Individual Polynucleotide Molecules Using a Membrane Channel," Proc. Natl. Acad. Sci. USA 93:13770-13773.
Kim S. et al. (2002) "Solid Phase Capturable Dideoxynucleotides for Multiplex Genotyping Using Mass Spectrometry," Nucleic Acids Research 30(16):e85.1-e85.6.
Kim, S. et al. (2003) "Multiplex Genotyping of the Human Beta2-adrenergic Receptor Gene Using Solid-phase Capturable Dideoxynucleotides and Mass Spectrometry," Analytical Biochemistry 316:251-258.
Kimzey A.L. et al. (1998) "Specific Regions of Contact Between Human T-cell Leukemia Virus Type I Tax Protein and DNA Identified By Photocross-linking," Journal of Biological Chemistry, 273(22): 13768-13775.
Kitamura et al. (2002) "(P(C6H5)3) CpRu+Catalyzed Deprotection of Allyl Carboxylic Esters," J. Org. Chem., 67:4975-4977.
Kloosterman et al. (1985) "The relative stability of allyl ether, allyloxycarbonyl ester and prop-2 enylidene acetal, protective groups toward Iridium, Rhodium and Palladium catalysts," Tetrahedron Letters, 26:5045-5048.
Kokoris, M. et al. (2000) "High-throughput SNP Genotyping With the Masscode System," Molecular Diagnosis 5(4) :329-340.
Kolb et al. (2001) "Click Chemistry: Diverse Chemical Function From a Few Good Reactions," Angew. Chem. Int. Ed. 40:2004-2021.
Kraevskii, A.A. et al. (1987) "Substrate Inhibitors of DNA Biosynthesis," Molecular Biology 21:25-29.
Krečmerová (1990) "Synthesis of 5'-O-Phosphonomethyl Derivatives of Pyrimidine 2'- Deoxynucleosides." Coll. Czech. Chem. Commun., 55:2521-2536.
Kurata et al. (2001) "Fluorescent quenching-based quantitative detection of specific DNA/RNA using BODIPY® FL-labeled probe of primer," Nucleic Acids Research, vol. 29, No. 6, p. e34.
Kvam et al., (1994) "Characterization of singlet oxygen-induced quanine residue damage after photochemical treatment of free nucleosides and DNA," Biochemica et Biophysica Acta., 1217:9-15.
Lee, L.G., et al. (1992) "DNA sequencing with dye labeled terminators and T7 DNA polymerase effect of dyes and dNTPs on incorporation of dye terminators and probablility analysis of termination fragments," Nucleic Acids Res. 20:2471-2483.
Lee, L.G. et al, (1997) "New energy transfer dyes for DNA sequencing," Nucleic Acids Res. 25:2816-2822.
Leroy, E.M. et al. (2000) "Diagnosis of Ebola Haemorrhagic Fever by RT-PCR in an Epidemic Setting," Journal of Medical Virology 60:463-467.

(56) References Cited

OTHER PUBLICATIONS

Lewis et al. (2002) "Click Chemistry in Situ: Acetylcholinesterase as a Reaction Vessel for the Selective Assembly of a Femtomolar Inhibitor from an Array of Building Blocks," Angew. Chem. Int. Ed. 41(6):1053-1057.

Li, J. (1999) "Single Oligonucleotide Polymorphism Determination Using Primer Extension and Time-of-Flight Mass Spectrometry," Electrophoresis 20:1258-126.

Li et al. (2003) "A photcleavable Fluorescent Nucleotide for DNA Sequencing and Analysis," PNAS 100(2):414-419.

Liu, H et al. (2000) "Development of Multichannel Devices with an Array of Electrospray Tips for High-Throughput Mass Spectrometry," Anal. Chem. 72:3303-3310.

Loubinoux, B. et al. "Protection Des Phenols Par Le Groupement Azidomethylene Application A La Synthese De Phenols Instables," Tetrahedron, 1998, 44(19): 6055 (English Abstract Only).

Lu, G. and Burgess, K. (2006) "A Diversity Oriented Synthesis of 3'-O-Modified Nucleoside Triphosphates for DNA 'Sequencing by Synthesis'" Bioorg. Med. Chem. Lett., 16:3902-3905.

Lyamichev, V. et al. (1999) "Polymorphism Identification and Quantitative Detection of Genomic DNA by Invasive Cleavage of Oligonucleotide Probes," Nat. Biotech 17:292-296.

Maier et al. (1995) "Synthesis and Properties of New Fluorescein-Labeled Oligonucleotides," Nucleosides and Nucleotides, 14:961-965.

Margulies, M.; Egholm, M.; Altman, W. E. (2005) "Genome Sequencing in Microfabricated High-Density Picolitre Reactors." Nature, 437:376-380.

Markiewicz et al. (1997) "A new method of synthesis of fluorescently labeled oligonucleotides and the application in DNA sequencing," Nucleic Acids Research, 25:3672-3690.

Marquez et al. (2003) "Selective Fluorescence Quenching of 2,3-Diazabicyclo [2.2.2]oct-2-ene by Nucleotides," Organic Letters, 5:3911-3914.

Mathews C.K. et al. (1985) "Chemical Synthesis of Oligonucleotides," Biochemistry, 2nd Edition, pp. 127-128.

Meng et al. (2006) "Design and Synthesis of a Photocleavable Fluorescent Nucleotide 3'-O-Allyl-dGTP-PC-Biodipy-FL-510 as a Reversible Terminator for DNA Sequencing by Synthesis," J. Org. Chem 71:3248-3252.

Metzker, M.L. et al. (1994) "Termination of DNA synthesis by novel 3' modified deoxyribonucleoside 5' triphosphates," Nucleic Acids Res. 22: 4259-4267.

Mitra, R. D.; Shendure J.; Olejnik, J.; et al. (2003) "Fluorescent in situ sequencing on polymerase colonies." Anal. Biochem. 320:55-65.

Monforte, J.A. and Becker, C.H. (1997) "High-throughput DNA analysis by time-of-flight mass spectrometry," Nat. Med. 3(3):360-362.

Nazarenko et al. (2002) "Effect of primary and secondary structure of olligdeoxyribonucleotides on the fluorescent properties of conjugated dyes," Nucleic Acids Research, 30:2089-2095.

Nickel et al. (1992) "Interactions of Azidothymidine triphosphate with the Cellular DNA polymerases alpha, delta, and episilon and with DNA Primase," J. Biol. Chem. 267(2):848-854.

Nielsen et al. (2004) "Multiplexed Sandwich Assays in Microarray Format," Journal of Immunological Methods, vol. 290, pp. 107-120.

Nishino et al. (1991) "Efficient Deanilidation of Phosphoranilidates by the Use of Nitrites and Acetic Anhydride." Heteroatom Chemistry, vol. 2, pp. 187-196.

Olejnik, J. et al. (1995) "Photocleavable biotin derivatives: a versatile approach for the isolation of biomolecules," Proc. Natl. Acad. Sci. USA. 92:7590-7594.

Olejnik, J. et al. (1999) "Photocleavable peptide DNA conjugates: synthesis and applications to DNA analysis using MALDI MS," Nucleic Acids Res. 27:4626-4631.

Pastinen et al. (1997) "Minisequencing: A Specific Tool for DNA Analysis and Diagnostics on Oligonucleotide Arrays," Genomic Res., 7:606-614.

Pelletier, H. et al. (1994) "Structures of ternary complexes of rat DNA polymerase β, a DNA template-primer, and ddCTP," Science 264:1891-1903.

Prober, J.M. et al. (1987) "A system for rapid DNA sequencing with fluorescent chain-terminating dideoxynucleotides," Science 238:336-341.

Quaedflieg et al. (1992) "An Alternative Approach Toward the Synthesis of (3'->5') Methylene Acetal Linked Dinucleosides," Tetrahedron Letters, vol. 33, pp. 3081-3084.

Rao et al. (2001) "Four Color FRET Dye Nucleotide Terminators For DNA Sequencing," Nucleosides, Nucleotides and Nucleic Acids, 20:673-676.

Rasolonjatovo et al. (1998) "6-N-(N-Methylanthranylamido)-4-Oxo-Hexanoic Acid: A New Fluorescent Protecting Group Applicable to a New DNA Sequencing Method," Nucleosides and Nucleotides, 17:2021-2025.

Ronaghi, (1998) "PCR-Introduced Loop Structure as Primer in DNA Sequencing." BioTechniques, 25:876.

Ronaghi, M., Uhlen, M., and Nyren, P. (1998) "A Sequencing Method Based on Real-time Pyrophosphate," Science 281:364-365.

Rosenblum, B.B. et al. (1997) "New dye-labeled terminators for improved DNA sequencing patterns," Nucleic Acids Res. 25:4500-4504.

Roskey, M.T., Juhasz, P., Smirnov, I.P., Takach, B.J., Martin, S.A., and Haff, L.A. (1996) "DNA sequencing by delayed extraction-matrix-assisted laser desorption/ionization time of flight mass spectrometry," Proc. Natl. Acad. Sci. USA. 93:4724-4729.

Ross, P.L. et al. (1997) "Discrimination of Single-Nucleotide Polymorphisms in Human DNA Using Peptide Nucleic Acid Probes Detected by MALDI-TOF Mass Spectrometry," Anal. Chem. 69:4197-4202.

Ross, P. et al. (1998) High Level Multiplex Genotyping by MALDI-TOF Mass Spectrometry. Nat. Biotech 16:1347-1351.

Ruparel et al. (2005) "Design and Synthesis of a 3'-O-Allyl Photocleavable Fluorescent Nucleotide as a Reversible Terminator for DNA Sequencing by Synthesis," PNAS 102(17):5932-5937.

Sarfati et al., (1995) "Synthesis of fluorescent derivatives of 3'-O-(6-aminohexanoyl)-pyrimidine nucleosides 5'-triphosphates that act as DNA polymerase substrates reversibly tagged at C-3'," JCS Perkin Trans, 1163-1171.

Saxon, E. and Bertozzi, C.R. (2000) "Cell surface engineering by a modified Staudinger reaction," Science 287:2007-2010.

Schena, M., Shalon, D. and Davis, R. Brown P.O. (1995) "Quantitative monitoring of gene expression patterns with a cDNA microarray," Science 270: 467-470.

Seeger (1998) "Single Molecule Fluorescence: High-Performance Molecular Diagnosis and Screening," Bioforum, Git Verlag, Darmstadt, DE vol. 21, (German text).

Seo et al. (2003) "Click Chemistry to Construct Fluorescent Oligonucleotides for DNA Sequencing," J. Org. Chem. 68:609-612.

Seo et al. (2004) "Photocleavable Fluorescent Nucleotides for DNA Sequencing on a Chip Constructed by Site-Specific Coupling Chemistry," PNAS 101(15):5488-5493.

Shendure, J.; Porreca, G. J.; Reppas, N.B.; et al. (2005) "Accurate Multiplex Polony Sequencing of Evolved Bacterial Genome," Science 309:1728-1732.

Smith, L.M., Sanders, J.Z., Kaiser, R.J., et al. (1986) "Fluorescence Detection in Automated DNA Sequence Analysis," Nature 321:674-679.

Speicher, M.R., Ballard, S.G., and Ward, D.C. (1996) "Karyotyping human chromosomes by combinatorial multi-fluor FISH," Nature Genetics 12: 368-375.

Stoerker, J. et al. (2000) "Rapid Genotyping by MALDI-monitored nuclease selection from probe Libraries," Nat. Biotech 18:1213-1216.

Tang, K., Fu, D.J., Julien, D., Braun, A., Cantor, C.R., and Koster, H. (1999) "Chip-based genotyping by mass spectrometry," Proc. Natl. Acad. Sci. USA. 96:10016-10020.

Tong, X. and Smith, L.M. (1992) "Solid-Phase Method for the Purification of DNA Sequencing Reactions," Anal. Chem. 64:2672-2677.

(56) References Cited

OTHER PUBLICATIONS

Torimura et al. (2001) "Fluorescence-Quenching Phenomenon by Photoinduced Electron Transfer between a Fluorescent Dye and Nucleotide Base," Analytical Sciences, 17:155-160.

Tuncel et al. (1999) "Catalytically Self-Threading Polyrotaxanes," Chem. Comm. 1509-1510.

Veeneman et al. (1991) "An Efficient Approach to the Synthesis of Thymidine Derivatives Containing Phosphate-Isoteric Methylene Acetyl Linkages," Tetrahedron, 47:1547-1562.

Wada et al. (2001) "2-(Azidomethyl)benzoyl as a new protecting group in nucleosides," Tetrahedron Letters, 42:1069-1072.

Weiss (1999) "Fluorescent Spectroscopy of Single Biomolecules." Science, 283:1676.

Welch et al. (1999) "Synthesis of Nucleosides Designed for Combinatorial DNA Sequencing," Chemistry, European Journal, 5:951-960.

Welch MB, Burgess K, (1999) "Synthesis of fluorescent, photolabile 3'-O-protected nucleoside triphosphates for the base addition sequencing scheme," Nucleosides and Nucleotides 18:197-201.

Wendy, Jen. Et al. (2000) "New Strategies for Organic Catalysis: The First Enantioselective Orgacnocatalytic 1,3-Dipolar Cycloaddition," J. Am. Chem. Soc. 122:9874-9875.

Woolley, A. T. et al. (1997) "High-Speed DNA Genotyping Using Microfabricated Capillary Array Electrophoresis Chips," Anal. Chem. 69:2181-2186.

Yamashita et al. (1987) "Studies on Antitumor Agents VII, Antitumor Activities of O-Alkoxyalkyl Derivatives of 2'- Deoxy-5-trifluoromethyluridine." Chem Pharm. Bull., vol. 35, pp. 2373-2381.

Zavgorodny, S. et al. (1991) "1-Alkylthioalkylation of Nucleoside Hydroxyl Functions and Its Synthetic Applications: A New Versatile Method in Nucleoside Chemistry," Tetrahedron Letters, 32(51): 7593-7596.

Zavgorodny et al. (2000) "S,X-Acetals in Nucleoside Chemistry. III. Synthesis of 2'- and 3'-O-Azidomethyl Derivatives of Ribonucleosides" Nucleosides, Nucleotides and Nucleic Acids, 19(10-12):1977-1991.

Zhang et al. (2002) "Synthesis of Releasable Electophore Tags for Applications in Mass Spectrometry," Bioconjugate Chem., vol. 13, pp. 1002-1012.

Zhu, Z., Chao, J., Yu, H, et al. (1994) "Directly Labeled DNA Probes Using Fluorescent Nucleotides with Different Length Linkers," Nucleic Acids Res., 22:3418-3422.

Office Action dated Aug. 10, 2007 in connection with U.S. Appl. No. 11/119,231.

Restriction Requirement dated Oct. 1, 2007 in connection with U.S. Appl. No. 10/521,206.

Office Action dated Nov. 14, 2007 in connection with U.S. Appl. No. 10/735,081.

Office Action dated Jul. 8, 2008 in connection with U.S. Appl. No. 10/591,520.

DNA SEQUENCING WITH NON-FLUORESCENT NUCLEOTIDE REVERSIBLE TERMINATORS AND CLEAVABLE LABEL MODIFIED NUCLEOTIDE TERMINATORS

This application is a continuation of U.S. Ser. No. 12/734,229, a § 371 national stage of PCT International Application No. PCT/US2008/011913, filed Oct. 17, 2008, and claims the benefit of U.S. Provisional Applications No. 60/999,580, filed Oct. 19, 2007 and 60/999,575, filed Oct. 19, 2007, the contents of all of which are hereby incorporated by reference into this application.

This invention was made with government support under grant HG358205 awards by the National Institutes of Health. The Government has certain rights in this invention.

Throughout this application, various publications are referenced in parentheses by number. Full citations for these references may be found at the end of the specification immediately preceding the claims. The disclosures of these publications in their entireties are hereby incorporated by reference into this application to more fully describe the state of the art to which this invention pertains.

BACKGROUND OF THE INVENTION

The completion of the Human Genome Project (HGP) in early 2000 (1) was a monumental achievement with incredible amount of combined efforts among genome centers and scientists worldwide. The engine behind this decade long project was the Sanger sequencing method, which still currently maintains as the staple of large-scale genome sequencing methodology in high-throughput genome sequencing centers. The main reason behind this prolonged success was in the basic and efficient, yet elegant method that is Sanger dideoxy chain terminating reaction (2). With incremental improvements in this DNA sequencing technology including the use of laser induced fluorescent excitation of energy transfer dyes (3), engineered DNA polymerases (4) and capillary electrophoresis (5) as well as in the areas of sample preparation, informatics, and sequence analysis software (6-9), the Sanger sequencing platform has been able to maintain its status as champion in the sequencing world. Current state-of-the-art Sanger based DNA sequencers can produce over 700 bases of clearly readable sequence in a single run from templates up to 30 kb in length (10-12). However, as is with most of technological inventions, the continual improvements in this sequencing platform has come to a stagnant plateau, with the current cost estimate for producing a high-quality microbial genome draft sequence at around $10,000 per megabase pair. Current DNA sequencers based on the Sanger method allow up to 384 samples to be analyzed in parallel. However, one of the drawbacks to using electrophoresis for DNA separation is the deterioration of resolution due to band compressions. DNA sequences that are repeat rich and promote formation of secondary structures, such as hairpins, affect electrophoretic mobility, which also result in band compressions. This is the main reason behind maximum read-length limit for this sequencing method (13, 14). From a physics and engineering standpoint, the maximum read-length and parallelization based on capillary electrophoresis separation has already been reached (15).

At the onset of the post HGP-era, with realization of current sequencing platform's limitation, both public (National Human Genome Research Institute, NHGRI) and private genomic sciences sector (The J. Craig Venter Science Foundation and Archon X prize for genomics) have mandated a call for the development of next-generation sequencing technology that will reduce the cost of sequencing 100 and 10,000 fold in the next 5 to 10 years, respectively (16-19). With the development of a breakthrough DNA sequencing technology, which is already underway with heavy biotechnology industry involvement (20), it will allow for affordable genome sequencing. Genome research will be able to be conducted where it will be possible to move from studying single genes at a time to analyzing and comparing entire genomes. Recent data has demonstrated that the fundamental differences between many species including between mammals is not the overall number of genes, but lies at the more subtle regulatory level (21). This has led to the desire to sequence more genomes of closely related species as well as more human genomes. In addition, personalized medicine, gene expression analysis, splice form analysis and many other areas have demands for high-throughput sequencing projects that cannot be performed at the current speeds and costs. To overcome the limitations of the current sequencing technology based on electrophoresis using laser induced fluorescence detection (22-24), new methods must be developed which start from new paradigms to build a sequencer that can handle the new demands imposed by these new goals. Potential sequencing methods making significant steps forward into the new sequencing era include pyrosequencing (25-26), mass spectrometry sequencing (27-29), sequence specific detection of single-stranded DNA using engineered-nanopores (30), sequencing of single DNA molecules (31), polony sequencing (32) and sequencing by synthesis using cleavable fluorescent reversible terminators (33).

While fluorescent-based SBS methods have almost unlimited ability for parallelization, restricted only by the resolution of the imaging system, to date they have been limited to read lengths of about 35 bases. The successful implementation of sequencing by synthesis (SBS) is effectively dependent on the read length of the target DNA template. One of the major factors that determines the read length when performing SBS is the number of available templates. Our laboratory has recently developed two powerful approaches for SBS: 1) Hybrid SBS with nucleotide reversible terminator (NRTs, 3'-O—$R_1$-dNTPs) in combination with fluorescently labeled dideoxynucleotide (ddNTPs-$R_2$-fluorophore), and 2) SBS with cleavable fluorescent nucleotide reversible terminator (C—F-NRTs, 3'-O—$R_1$-dNTPs-$R_2$-fluorophore) ("Four-color DNA Sequencing with 3'-O-modified Nucleotide Reversible Terminators and Chemically Cleavable Fluorescent Dideoxynucleotides". J. Guo, N. Xu, Z. Li, S. Zhang, J. Wu, D. Kim, M. S. Marma, Q. Meng, H. Cao, X. Li, S. Shi, L. Yu, S. Kalachikov, J. Russo, N. J. Turro, J. Ju. Proceedings of the National Academy of Sciences USA. 2008, 105, 9145-9150) ("Four-Color DNA Sequencing by Synthesis Using Cleavable Fluorescent Nucleotide Reversible Terminators". J. Ju, D. Kim, L. Bi, Q. Meng, X. Bai, Z. Li, X. Li, M. S. Marma, S. Shi, J. Wu, J. R. Edwards, A. Romu, N. J. Turro. Proceedings of the National Academy of Sciences USA. 2006, 103, 19635-19640). Since the incorporation of ddNTPs-$R_2$-fluorophore into a strand of DNA permanently terminates further extensions of that template in the first approach and the incorporation and cleavage of C—F-NRTs leaves a tail of the modified nucleotide that causes possible steric hindrance to lower the incorporation efficiency of the subsequent base in the second approach, the total number of sequenceable templates decreases after each cycle of SBS reaction. Various means can be employed to minimize this rate of template reduction. Among those, a powerful method termed template "walking" can potentially diminish the negative effect of template termination or reduction and extend the read length of SBS at least two to three-fold.

SUMMARY OF THE INVENTION

A method for determining the identity of each of a series of consecutive nucleotide residues in a nucleic acid comprising:

a) contacting a plurality of the nucleic acids with (i) a dideoxynucleotide triphosphate (ddNTP) analogue having the structure:

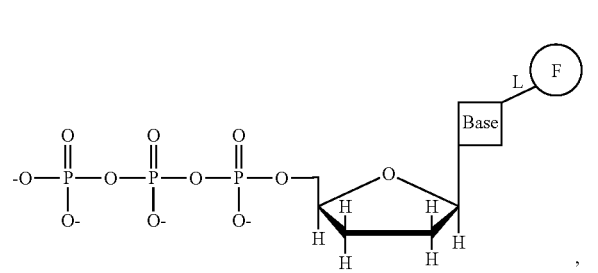

wherein F is a fluorophore, L is a cleavable linker molecule and the base is adenine, guanine, cytosine, uracil or thymine, and wherein each base has a different fluorophore attached, and wherein the fluorophore attached to each type of base differs in its excitation or emission spectra from the fluorophores attached to the other types of bases, (ii) a deoxynucleotide triphosphate (dNTP) analogue having the structure:

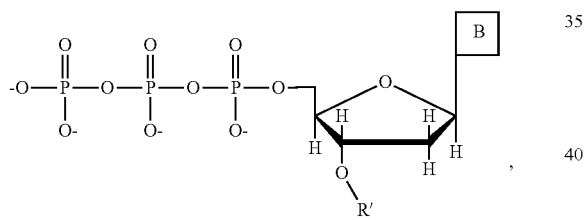

wherein B is a base and is adenine, guanine, cytosine, uracil, thymine or an inosine, and wherein R' is a cleavable chemical group, (iii) a nucleic acid polymerase and (iv) at least two primers each of which hybridizes with a separate nucleic acid of the plurality of nucleic acids,
under conditions permitting a ddNTP analogue that is complementary to the consecutive nucleotide residue to be identified to form a phosphodiester bond with the 3' end of one of the primers and a dNTP analogue that is complementary to the consecutive nucleotide residue to be identified to form a phosphodiester bond with the 3' end of another of the primers;

b) identifying the fluorophore of the ddNTP analogue which has formed the phosphodiester bond thereby identifying the identify of the consecutive nucleotide;

c) cleaving the fluorophore from the ddNTP analogue which has formed the phosphodiester bond and cleaving the cleavable chemical group from the dNTP which has formed the phosphodiester bond;

d) iteratively repeating steps a) through c) for each of the consecutive nucleotide residues to be identified until the final consecutive nucleotide residue is to be identified;

e) repeating steps a) and b) to identify the final consecutive nucleotide residue, thereby determining the identity of each of the series of consecutive nucleotide residues in the nucleic acid.

A method for determining the identity of consecutive nucleotide residues in a self-priming nucleic acid comprising:

a) contacting a plurality of the nucleic acids with (i) a dideoxynucleotide triphosphate (ddNTP) analogue having the structure:

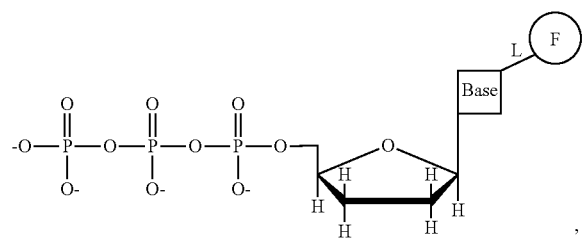

wherein F is a fluorophore, L is a cleavable linker molecule and the base is adenine, guanine, cytosine, uracil or thymine, wherein each base has a different fluorophore attached, (ii) a deoxynucleotide triphosphate (dNTP) analogue having the structure:

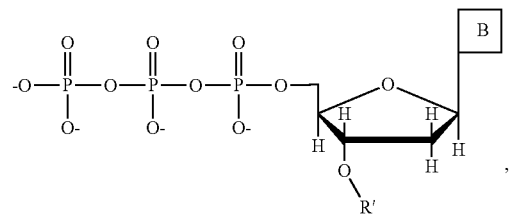

wherein B is a base and is adenine, guanine, cytosine, uracil, thymine or an inosine, and wherein R' is a cleavable chemical group, and (iii) a nucleic acid polymerase,
under conditions permitting a ddNTP analogue that is complementary to the consecutive nucleotide residue to be identified to form a phosphodiester bond with the 3' end of one of the self-priming nucleic acids and a dNTP analogue that is complementary to the consecutive nucleotide residue to be identified to form a phosphodiester bond with the 3' end of another of the self-priming nucleic acids;

b) identifying the fluorophore of the ddNTP analogue which has formed the phosphodiester bond thereby identifying the identify of the consecutive nucleotide;

c) cleaving the fluorophore from the ddNTP analogue which has formed the phosphodiester bond and cleaving the cleavable chemical group from the dNTP which has formed the phosphodiester bond;

d) iteratively repeating steps a) through c) for each of the consecutive nucleotide residues to be identified until the final consecutive nucleotide residue is to be identified;

e) repeating steps a) and b) to identify the final consecutive nucleotide residue, thereby determining the identity of each of the series of consecutive nucleotide residues in the nucleic acid.

A kit for sequencing a nucleic acid is provided comprising ddNTP analogues and dNTP analogues described herein and instructions for use in sequencing.

A compound having the structure:

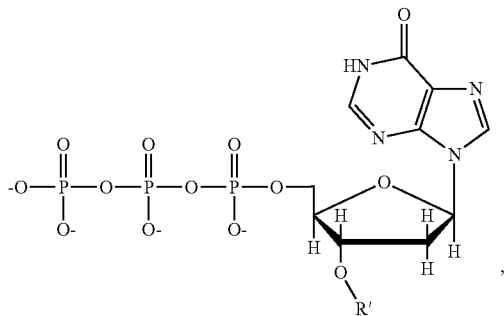

wherein R' is a cleavable chemical group.

A deoxyribonucleic acid having attached at a 3' end thereof, by a phosphodiester bond, a compound having the structure:

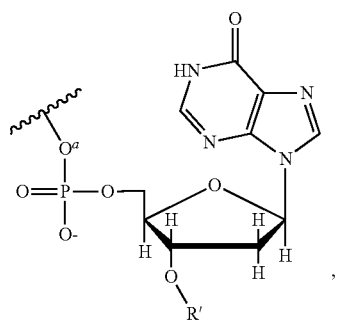

wherein the O atom labeled α is the 3' O atom of the deoxyribonucleic acid, the wavy line represents the remainder of the deoxyribonucleic acid that is 5' relative to the 3'O, and wherein R' is a cleavable chemical group.

A kit for sequencing a nucleic acid is provided comprising detectably-labeled dideoxynucleotide triphosphate analogues and the dITP analogue herein and instructions for use in sequencing.

DETAILED DESCRIPTION OF THE INVENTION

Terms

Figure 1:
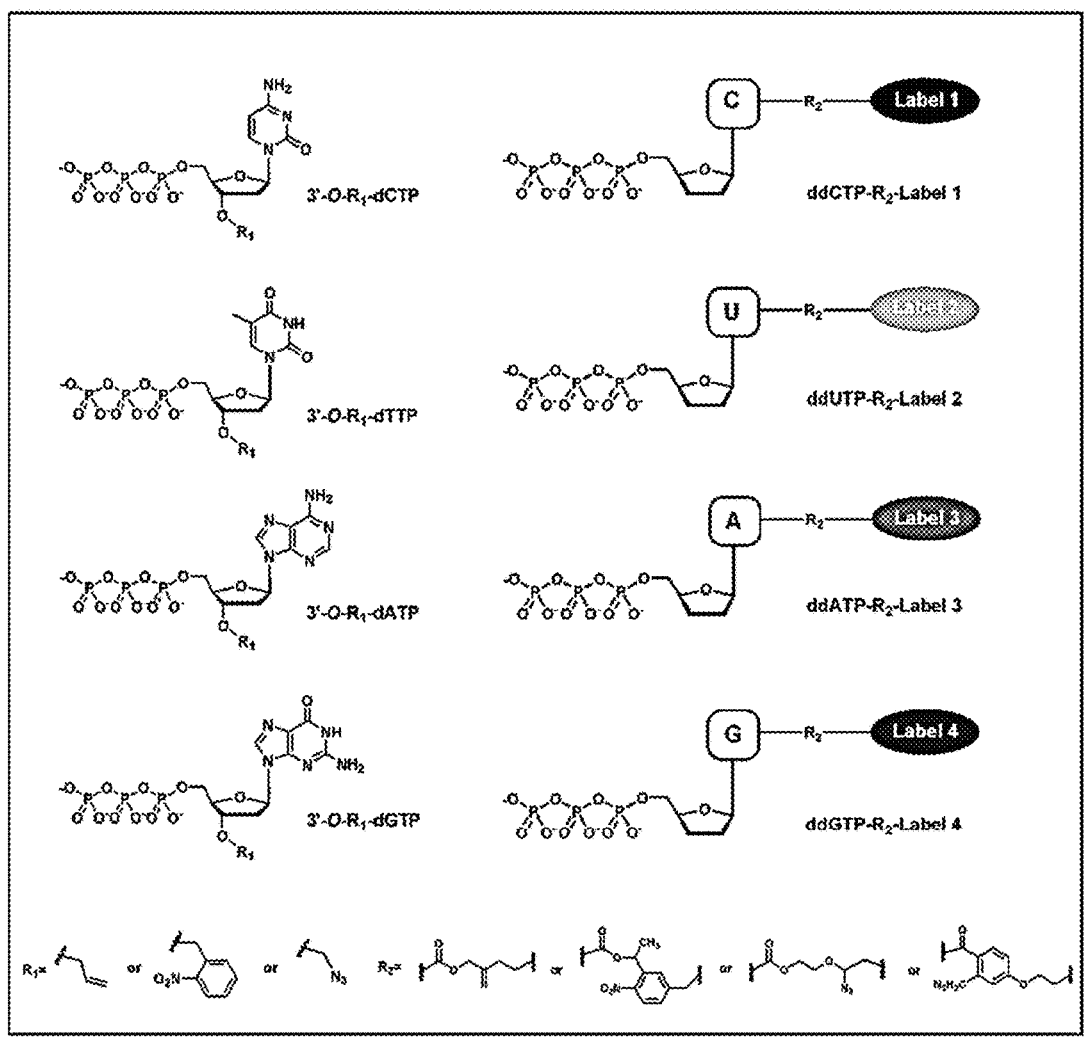
FIG. 1. Structures of the nucleotide reversible terminators, 3'-O—$R_1$-dATP, 3'-O—$R_1$-dCTP, 3'-O—$R_1$-dGTP, 3'-O—$R_1$-dTTP (left). Structures of the cleavable label modified dideoxynucleotide terminators, ddNTPs-$R_2$-Label (right), with 4 distinct labels corresponding to 4 different bases: ddCTP-$R_2$-Label 1, ddUTP-$R_2$-Label 2, ddATP-$R_2$-Label 3, and ddGTP-$R_2$-Label 4.

As used herein, and unless stated otherwise, each of the following terms shall have the definition set forth below.
A—Adenine;
C—Cytosine;
DNA—Deoxyribonucleic acid;
G—Guanine;
RNA—Ribonucleic acid;
T—Thymine; and
U—Uracil.

"Nucleic acid" shall mean any nucleic acid molecule, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA).

"Type" of nucleotide refers to Adenine, Guanine, Cytosine, Thymine or Uracil. "Type" of base refers to adenine, uracil, cytosine, guanine or thymine.

"Mass tag" shall mean a molecular entity of a predetermined size which is capable of being attached by a cleavable bond to another entity.

"Solid substrate" shall mean any suitable medium present in the solid phase to which a nucleic acid or an agent may be affixed. Non-limiting examples include chips, beads and columns.

"Hybridize" shall mean the annealing of one single-stranded nucleic acid to another nucleic acid based on sequence complementarity. The propensity for hybridization between nucleic acids depends on the temperature and ionic strength of their milieu, the length of the nucleic acids and the degree of complementarity. The effect of these parameters on hybridization is well known in the art (see Sambrook J, Fritsch E F, Maniatis T. 1989. Molecular cloning: a laboratory manual. Cold Spring Harbor Laboratory Press, New York.)

As used herein, hybridization of a primer sequence shall mean annealing sufficient such that the primer is extendable by creation of a phosphodiester bond.

As used herein, a ddNTP analogue, unless otherwise indicated, is a ddNTP substituted as its base with a linker molecule attached to a detectable marker, wherein the substitution is such that it does not prevent the ddNTP analogue from being incorporated by a nucleic acid polymerase into a primer extension stand resulting from a self-priming nucleic acid or from a primer hybridized to a nucleic acid of interest.

As used herein, a dNTP analogue, unless otherwise indicated, is a dNTP substituted as its base with a linker molecule attached to a detectable marker, wherein the substitution is such that it does not prevent the dNTP analogue from being incorporated by a nucleic acid polymerase into a primer extension stand resulting from a self-priming nucleic acid or from a primer hybridized to a nucleic acid of interest.

Where a range of values is provided, it is understood that each intervening value, to the tenth of the unit (if appropriate) of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Embodiments of the Invention

A method is provided for determining the identity of each of a series of consecutive nucleotide residues in a nucleic acid comprising:
a) contacting a plurality of the nucleic acids with (i) a dideoxynucleotide triphosphate (ddNTP) analogue having the structure:

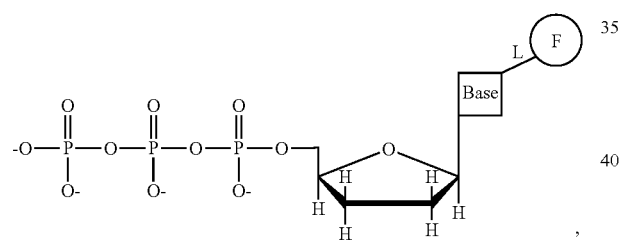

wherein F is a fluorophore, L is a cleavable linker molecule and the base is adenine, guanine, cytosine, uracil or thymine, and wherein each base has a different fluorophore attached, and wherein the fluorophore attached to each type of base differs in its excitation or emission spectra from the fluorophores attached to the other types of bases, (ii) a deoxynucleotide triphosphate (dNTP) analogue having the structure:

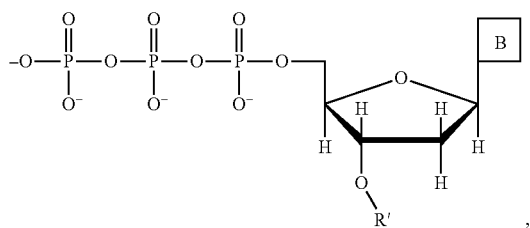

wherein B is a base and is adenine, guanine, cytosine, uracil or thymine, and wherein R' is a cleavable chemical group, (iii) a nucleic acid polymerase and (iv) at least two primers each of which hybridizes with a separate nucleic acid of the plurality of nucleic acids, under conditions permitting a ddNTP analogue that is complementary to the consecutive nucleotide residue to be identified to form a phosphodiester bond with the 3' end of one of the primers and a dNTP analogue that is complementary to the consecutive nucleotide residue to be identified to form a phosphodiester bond with the 3' end of another of the primers;
b) identifying the fluorophore of the ddNTP analogue which has formed the phosphodiester bond thereby identifying the identify of the consecutive nucleotide;
c) cleaving the fluorophore from the ddNTP analogue which has formed the phosphodiester bond and cleaving the cleavable chemical group from the dNTP which has formed the phosphodiester bond;
d) iteratively repeating steps a) through c) for each of the consecutive nucleotide residues to be identified until the final consecutive nucleotide residue is to be identified;
e) repeating steps a) and b) to identify the final consecutive nucleotide residue,
thereby determining the identity of each of the series of consecutive nucleotide residues in the nucleic acid.

In an embodiment, the dNTP is a deoxyinosine triphosphate (dITP) analogue having the structure:

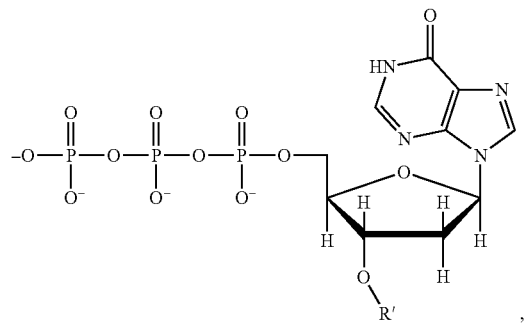

wherein R' is a cleavable chemical group.

In an embodiment, the dNTP is adenine, guanine, cytosine, uracil or thymine. In an embodiment, the nucleic acid is DNA and the nucleic acid polymerase is a DNA polymerase. In anther embodiment, the nucleic acid is RNA and the polymerase is an RNA polymerase. In an embodiment, the plurality of nucleic acids are contacted in step a) with ddNTP analogues and dNTP analogues in a ddNTP:dNTP analogue ratio of about 1:10, 1:50, 1:250, or 1:500. In an embodiment, R' is a nitrobenzyl group, an allyl group or a methylazido group. In an embodiment, the linker molecule is photocleavable. In an embodiment, the 1 carbon of the dideoxyribose is bonded to the 9 nitrogen of a guanine or adenine base or wherein the 1 carbon of the dideoxyribose is bonded to the 1 nitrogen of cytosine, thymine or uracil base. In an embodiment, the steps are performed in the order a), b), c), d) and e). In an embodiment, the steps are performed in the order a), c), b), d), and e).

In an embodiment, up to 1000 consecutive nucleotides are identified. In an embodiment, up to $1 \times 10^4$ consecutive nucleotides are identified. In an embodiment, up to $1 \times 10^6$ consecutive nucleotides are identified.

A method for determining the identity of consecutive nucleotide residues in a self-priming nucleic acid comprising:

a) contacting a plurality of the nucleic acids with (i) a dideoxynucleotide triphosphate (ddNTP) analogue having the structure:

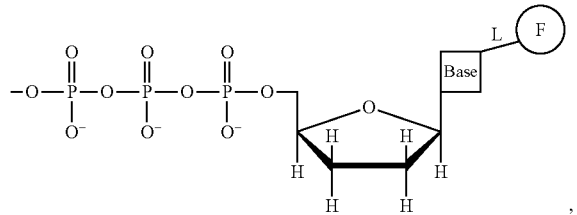

wherein F is a fluorophore, L is a cleavable linker molecule and the base is adenine, guanine, cytosine, uracil or thymine, wherein each base has a different fluorophore attached, (ii) a deoxynucleotide triphosphate (dNTP) analogue having the structure:

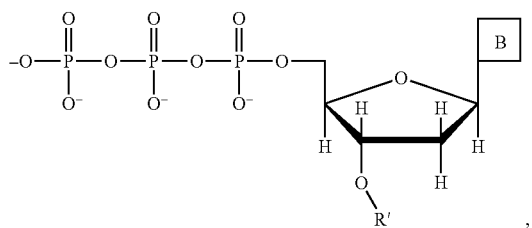

wherein B is a base and is adenine, guanine, cytosine, uracil, thymine or an inosine, and wherein R' is a cleavable chemical group, and (iii) a nucleic acid polymerase,
under conditions permitting a ddNTP analogue that is complementary to the consecutive nucleotide residue to be identified to form a phosphodiester bond with the 3' end of one of the self-priming nucleic acids and a dNTP analogue that is complementary to the consecutive nucleotide residue to be identified to form a phosphodiester bond with the 3' end of another of the self-priming nucleic acids;

b) identifying the fluorophore of the ddNTP analogue which has formed the phosphodiester bond thereby identifying the identify of the consecutive nucleotide;

c) cleaving the fluorophore from the ddNTP analogue which has formed the phosphodiester bond and cleaving the cleavable chemical group from the dNTP which has formed the phosphodiester bond;

d) iteratively repeating steps a) through c) for each of the consecutive nucleotide residues to be identified until the final consecutive nucleotide residue is to be identified;

e) repeating steps a) and b) to identify the final consecutive nucleotide residue, thereby determining the identity of each of the series of consecutive nucleotide residues in the nucleic acid.

In an embodiment, the dNTP is a deoxyinosine triphosphate (dITP) analogue having the structure:

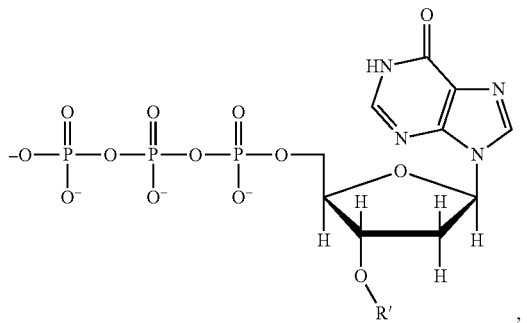

wherein R' is a cleavable chemical group.

In an embodiment, the dNTP is adenine, guanine, cytosine, uracil or thymine. In an embodiment, nucleic acid is DNA and the nucleic acid polymerase is a DNA polymerase. In another embodiment, the nucleic acid is RNA and the polymerase is an RNA polymerase. In an embodiment, the plurality of nucleic acids are contacted in step a) with ddNTP analogues and dNTP analogues in a ddNTP:dNTP analogue ratio of about 1:10, 1:50, 1:250, or 1:500. In an embodiment, R' is a nitrobenzyl group, an allyl group or a methylazido group. In an embodiment, the linker molecule is photocleavable. In an embodiment, the 1 carbon of the dideoxyribose is bonded to the 9 nitrogen of a guanine or adenine base or the 1 carbon of the dideoxyribose is bonded to the 1 nitrogen of cytosine, thymine or uracil base. In an embodiment, the steps are performed in the order a), b), c), d) and e). In an embodiment, the steps are performed in the order a), c), b), d), and e).

In an embodiment, up to 1000 consecutive nucleotides are identified. In an embodiment, up to $1 \times 10^4$ consecutive nucleotides are identified. In an embodiment, up to $1 \times 10^6$ consecutive nucleotides are identified.

A kit for sequencing a nucleic acid is provided comprising ddNTP analogues and dNTP analogues described herein and instructions for use in sequencing.

A compound is provided having the structure:

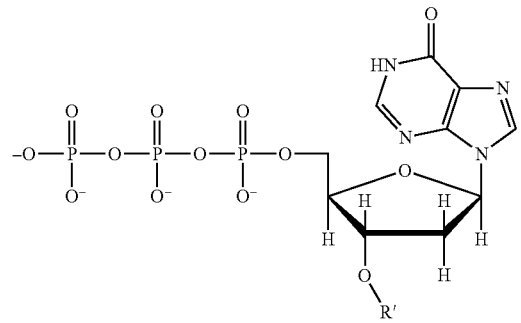

wherein R' is a cleavable chemical group.

In an embodiment, R' is a nitrobenzyl group, an allyl group or a methylazido group. In an embodiment, the base has a detectable marker cleavably linked thereto.

A deoxyribonucleic acid is provided having attached at a 3' end thereof, by a phosphodiester bond, a compound having the structure:

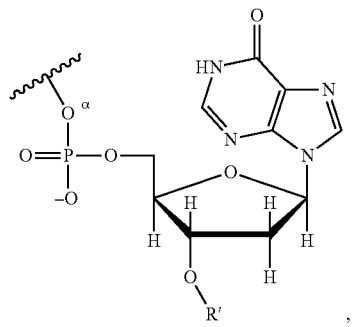

wherein the O atom labeled α is the 3' O atom of the deoxyribonucleic acid, the wavy line represents the remainder of the deoxyribonucleic acid that is 5' relative to the 3'O, and wherein R' is a cleavable chemical group.

In an embodiment, R' is a nitrobenzyl group, an allyl group or a methylazido group. In an embodiment, the deoxyribonucleic acid is attached to a solid surface.

R' can have the structure:

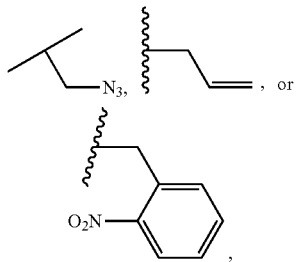

where the wavy line represents the point of attachment to the 3' O atom.

L, as the linker molecule, can comprise or consist of the structure:

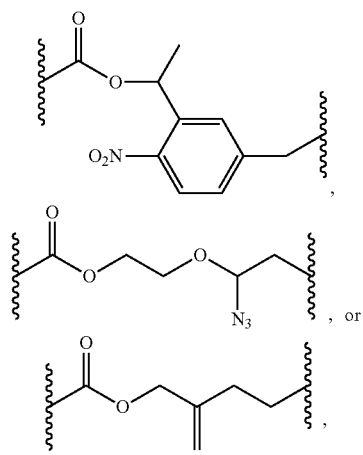

wherein the left hand wavy line represents the point of attachment to a base, or further molecule connecting to the base, and the right hand wavy line represents the point of attachment to a fluorophore or other detectable marker, or a further molecule connecting to the fluorophore or other detectable marker.

A kit for sequencing a nucleic acid is provided comprising ddNTP analogues and dITP analogues described herein and instructions for use in sequencing.

In the methods, compositions and kits disclosed herein, the dNTP:ddNTP ratio can be altered to optimize results. Embodiments include 10:1, 100:1, 1000:1, 10,000:1, 100,000:1, 10-100:1, 100-1,000:1, 1,000-10,1000:1, 10,000-100,000:1 of dNTP analogues to ddNTP analogues.

This invention provides the instant method, wherein the detectable bound to the base via a cleavable linker is a dye, a fluorophore, a chromophore, a combinatorial fluorescence energy transfer tag, a mass tag, or an electrophore.

This invention also provides the instant method, wherein the primer is a self-priming moiety.

This invention also provides the instant method, wherein the DNA is bound to a solid substrate. This invention also provides the instant method, wherein the DNA is bound to the solid substrate via 1,3-dipolar azide-alkyne cycloaddition chemistry. This invention also provides the instant method, wherein the DNA is bound to the solid substrate via a polyethylene glycol molecule. This invention also provides the instant method, wherein the DNA is alkyne-labeled. This invention also provides the instant method, wherein the DNA is bound to the solid substrate via a polyethylene glycol molecule and the solid substrate is azide-functionalized. This invention also provides the instant method, wherein the DNA is immobilized on the solid substrate via an azido linkage, an alkynyl linkage, or biotin-streptavidin interaction. Immobilization of nucleic acids is described in Immobilization of DNA on Chips II, edited by Christine Wittmann (2005), Springer Verlag, Berlin, which is hereby incorporated by reference.

This invention also provides the instant method, wherein the solid substrate is in the form of a chip, a bead, a well, a capillary tube, a slide, a wafer, a filter, a fiber, a porous media, or a column. This invention also provides the instant method, wherein the solid substrate is gold, quartz, silica, plastic, glass, diamond, silver, metal, or polypropylene. This invention also provides the instant method, wherein the solid substrate is porous. Chips or beads may be made from materials common for DNA microarrays, for example glass or nylon. Beads/micro-beads may be in turn immobilized to chips.

This invention also provides the instant method, wherein about 1000 or fewer copies of the DNA are bound to the solid substrate. This invention also provides the instant invention wherein $2 \times 10^7$, $1 \times 10^7$, $1 \times 10^6$ or $1 \times 10^4$ or fewer copies of the DNA are bound to the solid substrate.

This invention also provides the instant method, wherein the nucleotide analogues comprise one of the fluorophores Cy5, Bodipy-FL-510, ROX and R6G.

This invention also provides the instant method, wherein the four deoxynucleotide analogues are 3'-O-allyl-dGTP, 3'-O-allyl-dCTP, 3'-O-allyl-dATP and 3'-O-allyl-dUTP. This invention also provides the instant method, wherein the four deoxynucleotide analogues are 3'-O-methylazido-dGTP, 3'-O-methylazido-dCTP, 3'-O-methylazido-dATP and 3'-O-methylazido-dUTP. It is understood that in other embodiments the deoxynucleotide or dideoxynucleotide analogues are photocleavable. For example, photocleavable linkers such as 2-nitrobenzyl can replace any of the allyl moieties in the analogues described herein. For example, 3'-O-2-nitrobenzyl-dGTP, 3'-O-2-nitrobenzyl-dATP, 3'-O-2-nitrobenzyl-dGTP, 3'-O-2-nitrobenzyl-dATP. One of skill in the art would recognize various other chemically cleavable or photochemically cleavable moieties or linkers that can be used in place of the examples described herein. Additionally, the unique labels may also be varied, and the examples set forth herein are non-limiting. In an embodiment UV light is used to photochemically cleave the photochemically cleavable linkers and moieties.

This invention also provides the instant method, wherein the deoxynucleotide analogue is 3'-O-allyl-dITP, or 3'-O-methylazido-dITP. It is understood that in other embodiments the modifications of the deoxynucleotide or dideoxynucleotide analogues are photocleavable. For example, photocleavable linkers, such as 2-nitrobenzyl, can replace any of the allyl moieties in the analogues described herein. For example, 3'-O-2-nitrobenzyl-dITP. One of skill in the art would recognize various other chemically cleavable or photochemically cleavable moieties or linkers that can be used in place of the examples described herein. Additionally, the unique labels may also be varied, and the examples set forth herein are non-limiting. In an embodiment UV light is used to photochemically cleave the photochemically cleavable linkers and moieties.

This invention also provides the instant method, wherein the dideoxynucleotide terminators are have a detectable marker, for example a fluorophore, a mass tag, a chromophore etc., attached to the base thereof via an allyl linker, a photocleavable linker or other linkers known in the art including the photocleavable linkers set forth herein.

This invention also provides the instant method, wherein the dideoxynucleotide terminators are 3'-O-allyl-dGTP, 3'-O-allyl-dCTP, 3'-O-allyl-dATP and 3'-O-allyl-dUTP, 3'-O-2-nitrobenzyl-dGTP, 3'-O-2-nitrobenzyl-dCTP, 3'-O-2-nitrobenzyl-dATP and 3'-O-2-nitrobenzyl-dUTP, 3-O-methylazido-dGTP, 3'-O-methylazido-dCTP, 3'-O-methylazido-dATP and 3'-O-methylazido-dUTP, 3'-O-2-methylazido-dGTP, 3'-O-2-methylazido-dCTP, 3'-O-2-methylazido-dATP and 3'-O-2-methylazido-dUTP.

This invention also provides the instant method, wherein the DNA polymerase is a 9° N polymerase or a variant thereof. DNA polymerases which can be used in the instant invention include, for example E. Coli DNA polymerase I, Bacteriophage T4 DNA polymerase, Sequenase™, Taq DNA polymerase and 9° N polymerase (exo-) A485L/Y409V.RNA polymerases which can be used in the instant invention include, for example, Bacteriophage SP6, T7 and T3 RNA polymerases.

This invention also provides the instant method, wherein the DNA or nucleic acid being sequenced (i.e. consecutive nucleotides thereof being identified) is bound to the solid substrate via a polyethylene glycol molecule and the solid substrate is azide-functionalized or the DNA is immobilized on the solid substrate via an azido linkage, an alkynyl linkage, or biotin-streptavidin interaction. Immobilization of nucleic acids is described in Immobilization of DNA on Chips II, edited by Christine Wittmann (2005), Springer Verlag, Berlin, which is hereby incorporated by reference.

Methods for production of cleavably capped and/or cleavably linked nucleotide analogues are disclosed in U.S. Pat. No. 6,664,079, which is hereby incorporated by reference. Combinatorial fluorescence energy tags and methods for production thereof are disclosed in U.S. Pat. No. 6,627,748, which is hereby incorporated by reference.

In an embodiment, the DNA or nucleic acid is attached/bound to the solid surface by covalent site-specific coupling chemistry compatible with DNA.

A method for determining the identity of each of a series of consecutive nucleotide residues in a nucleic acid comprising:
  a) contacting a plurality of the nucleic acids with (i) a dideoxynucleotide triphosphate (ddNTP) analogue having the structure:

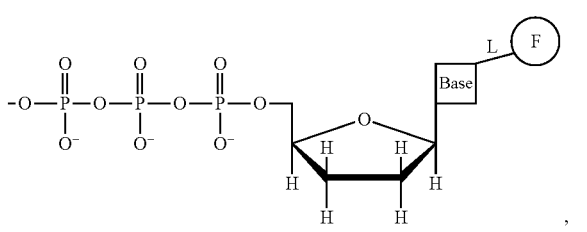

wherein F is a fluorophore, L is a cleavable linker molecule and the base is adenine, guanine, cytosine, uracil or thymine, and wherein each base has a different fluorophore attached, and wherein the fluorophore attached to each type of base differs in its excitation or emission spectra from the fluorophores attached to the other types of bases, (ii) a deoxynucleotide triphosphate (dNTP) analogue having the structure:

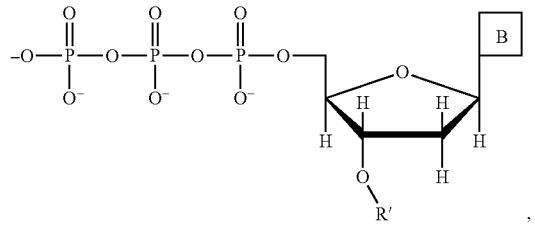

wherein B is a base and is adenine, guanine, cytosine, uracil, thymine or an inosine, and wherein R' is a cleavable chemical group, (iii) a nucleic acid polymerase and (iv) at least two primers each of which hybridizes with a separate nucleic acid of the plurality of nucleic acids,
  under conditions permitting a ddNTP analogue that is complementary to the consecutive nucleotide residue to be identified to form a phosphodiester bond with the 3' end of one of the primers and a dNTP analogue that is complementary to the consecutive nucleotide residue to be identified to form a phosphodiester bond with the 3' end of another of the primers;
  b) identifying the fluorophore of the ddNTP analogue which has formed the phosphodiester bond thereby identifying the identify of the consecutive nucleotide;
  c) cleaving the fluorophore from the ddNTP analogue which has formed the phosphodiester bond and cleaving the cleavable chemical group from the dNTP which has formed the phosphodiester bond;
  d) iteratively repeating steps a) through c) for each of the consecutive nucleotide residues to be identified until the final consecutive nucleotide residue is to be identified;
  e) repeating steps a) and b) to identify the final consecutive nucleotide residue,
  thereby determining the identity of each of the series of consecutive nucleotide residues in the nucleic acid.

In an embodiment the dNTP is a deoxyinosine triphosphate (dITP) analogue having the structure:

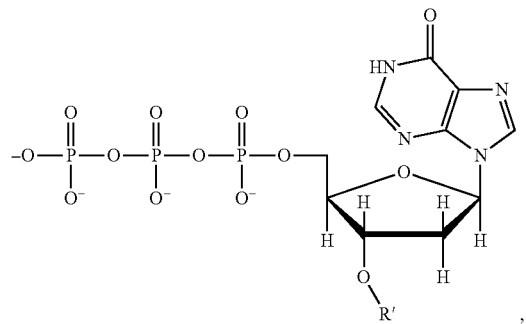

wherein R' is a cleavable chemical group.

In an embodiment the base of the dNTP is adenine, guanine, cytosine, uracil or thymine.

In an embodiment the nucleic acid is DNA and the nucleic acid polymerase is a DNA polymerase.

In an embodiment wherein the plurality of nucleic acids are contacted in step a) with ddNTP analogues and dNTP analogues in a ddNTP analogues:dNTP analogues ratio of about 1:10, 1:50, 1:250, or 1:500.

In an embodiment R' is a nitrobenzyl group, an allyl group or a methylazido group.

In an embodiment the linker molecule is photocleavable.

In an embodiment the 1 carbon of the dideoxyribose is bonded to the 9 nitrogen of a guanine or adenine base or wherein the 1 carbon of the dideoxyribose is bonded to the 1 nitrogen of cytosine, thymine or uracil base.

In an embodiment the 1 carbon of the dideoxyribose is bonded to the 9 nitrogen of an inosine base.

In an embodiment up to 1000 consecutive nucleotides are identified.

In an embodiment up to $1 \times 10^4$ consecutive nucleotides are identified.

In an embodiment up to $1 \times 10^6$ consecutive nucleotides are identified.

A method for determining the identity of consecutive nucleotide residues in a self-priming nucleic acid comprising:

a) contacting a plurality of the nucleic acids with (i) a dideoxynucleotide triphosphate (ddNTP) analogue having the structure:

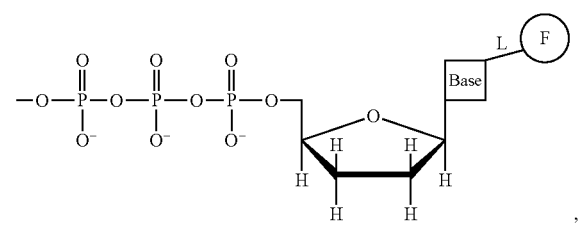

wherein F is a fluorophore, L is a cleavable linker molecule and the base is adenine, guanine, cytosine, uracil or thymine, wherein each base has a different fluorophore attached, (ii) a deoxynucleotide triphosphate (dNTP) analogue having the structure:

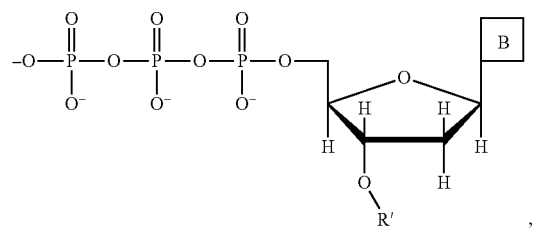

wherein B is a base and is adenine, guanine, cytosine, uracil, thymine or an inosine, and wherein R' is a cleavable chemical group, and (iii) a nucleic acid polymerase, under conditions permitting a ddNTP analogue that is complementary to the consecutive nucleotide residue to be identified to form a phosphodiester bond with the 3' end of one of the self-priming nucleic acids and a dNTP analogue that is complementary to the consecutive nucleotide residue to be identified to form a phosphodiester bond with the 3' end of another of the self-priming nucleic acids;

b) identifying the fluorophore of the ddNTP analogue which has formed the phosphodiester bond thereby identifying the identity of the consecutive nucleotide;

c) cleaving the fluorophore from the ddNTP analogue which has formed the phosphodiester bond and cleaving the cleavable chemical group from the dNTP which has formed the phosphodiester bond;

d) iteratively repeating steps a) through c) for each of the consecutive nucleotide residues to be identified until the final consecutive nucleotide residue is to be identified;

e) repeating steps a) and b) to identify the final consecutive nucleotide residue, thereby determining the identity of each of the series of consecutive nucleotide residues in the nucleic acid.

In an embodiment the dNTP is a deoxyinosine triphosphate (dITP) analogue having the structure:

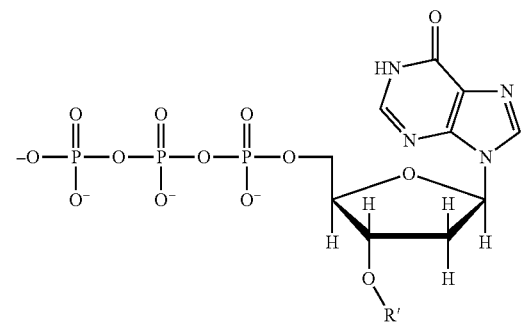

wherein R' is a cleavable chemical group.

In an embodiment the base of the dNTP is adenine, guanine, cytosine, uracil or thymine.

In an embodiment the nucleic acid is DNA and the nucleic acid polymerase is a DNA polymerase.

In an embodiment the plurality of nucleic acids are contacted in step a) with ddNTP analogues and dNTP analogues in a ddNTP analogues:dNTP analogue ratio of about 1:10, 1:50, 1:250, or 1:500.

In an embodiment R' is a nitrobenzyl group, an allyl group or a methylazido group.

In an embodiment the linker molecule is photocleavable.

In an embodiment the 1 carbon of the dideoxyribose is bonded to the 9 nitrogen of a guanine or adenine base or wherein the 1 carbon of the dideoxyribose is bonded to the 1 nitrogen of cytosine, thymine or uracil base.

In an embodiment the 1 carbon of the dideoxyribose is bonded to the 9 nitrogen of an inosine base.

In an embodiment up to 1000 consecutive nucleotides are identified.

In an embodiment up to $1 \times 10^4$ consecutive nucleotides are identified.

In an embodiment up to $1 \times 10^6$ consecutive nucleotides are identified.

In an embodiment the steps are performed in the order a), b), c), d), and e).

In an embodiment the steps are performed in the order a), c), b), d), and e).

A kit for sequencing a nucleic acid is provided comprising ddNTP analogues and dNTP analogues described herein and instructions for use in sequencing.

A compound having the structure:

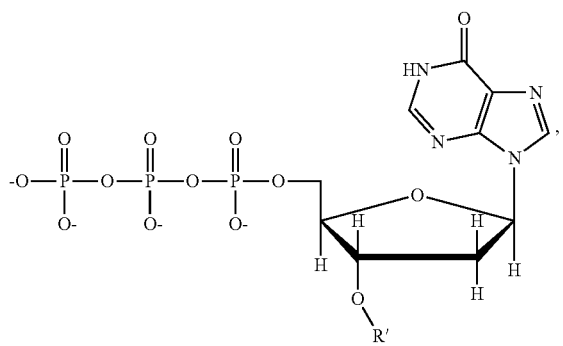

wherein R' is a cleavable chemical group.

In an embodiment R' is a nitrobenzyl group, an allyl group or a methylazido group.

In an embodiment the base has a detectable marker cleavably linked thereto.

A deoxyribonucleic acid having attached at a 3' end thereof, by a phosphodiester bond, a compound having the structure:

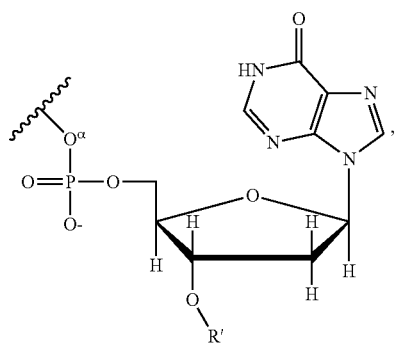

wherein the O atom labeled α is the 3' O atom of the deoxyribonucleic acid, the wavy line represents the remainder of the deoxyribonucleic acid that is 5' relative to the 3'O, and wherein R' is a cleavable chemical group.

In an embodiment R' is a nitrobenzyl group, an allyl group or a methylazido group.

In an embodiment the deoxyribonucleic acid is attached to a solid surface.

A kit for sequencing a nucleic acid is provided comprising detectably-labeled dideoxynucleotide triphosphate analogues and the dITP analogue of claim 31 and instructions for use in sequencing.

A method for determining the identity of each of a series of consecutive nucleotide residues in a nucleic acid comprising:
a) contacting a plurality of the nucleic acids with (i) at least four different dideoxynucleotide triphosphate (ddNTP) analogues, each having the structure:

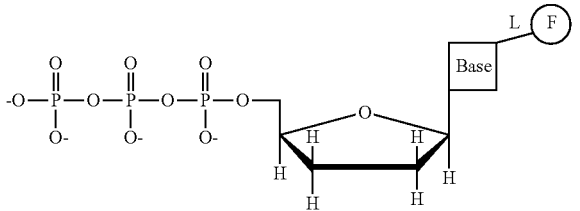

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four ddNTP analogues differs from the remaining three ddNTP analogues by having a different base, wherein L is a cleavable linker molecule, (ii) at least four deoxynucleotide triphosphate (dNTP) analogues having the structure:

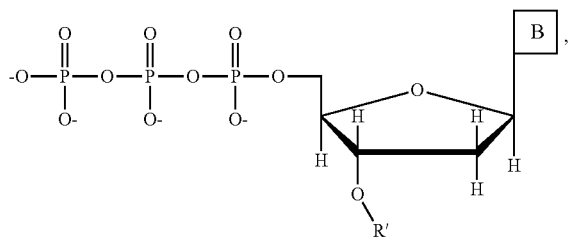

wherein B is a base and is adenine, guanine, cytosine, uracil, or thymine, and wherein R' is a cleavable chemical group, wherein each of the four dNTP analogues differs from the remaining three dNTP analogues by having a different base, (iii) a nucleic acid polymerase and (iv) a plurality of nucleic acid primers which can each hybridize with a separate one of each of the plurality of nucleic acids, under conditions permitting (a) one of the four ddNTP analogues that is complementary to the consecutive nucleotide residue to be identified to form a phosphodiester bond with the 3' end of one of the nucleic acid primers and thereby extend the primer and (b) one of the four dNTP analogues that is complementary to a consecutive nucleotide residue to be identified to form a phosphodiester bond with the 3' end of another one of the nucleic acid primers and thereby extend that primer;
b) identifying the fluorophore of the ddNTP analogue which has formed the phosphodiester bond, thereby identifying the consecutive nucleotide;
c) cleaving the linker attaching the fluorophore of the ddNTP analogue which has formed the phosphodiester bond and cleaving the cleavable chemical group from the dNTP which has formed the phosphodiester bond;
d) iteratively repeating steps a) through c) for each of the consecutive nucleotide residues to be identified until the final consecutive nucleotide residue is to be identified;
e) repeating steps a) and b) to identify the final consecutive nucleotide residue,
f) denaturing the extended primers so that they dehybridize from the plurality of nucleic acids;
g) contacting the plurality of nucleic acids with (i) at least four different deoxynucleotide triphosphate (dNTP) analogues each comprising a base chosen from adenine, thymine, cytosine, uracil, inosine, or 5-nitroindole, each differing from a deoxynucleotide triphosphate by having a cleavable chemical group attached to the 3' O-atom of the dNTP, (ii) a nucleic acid polymerase and (iii) a plurality of second nucleic acid primers which each separately hybridize with a separate one of the plurality of nucleic acids, under conditions permitting one of the four dNTP analogues that is complementary to the consecutive nucleotide residue to be identified to form a phosphodiester bond with the 3' end of one of the second nucleic acid primers and thereby extend that second primer;

h) cleaving the chemical group from the 3' O-atom of the dNTP analogue which has formed the phosphodiester bond so as to thereby permit incorporation of a further dNTP analogue into the extended second nucleic acid primer;

i) iteratively repeating steps g) and h) until the second primer is extended up to and including a residue corresponding to the final consecutive nucleotide residue identified in step e);

j) contacting the plurality of extended second primers with (i) at least four different dideoxynucleotide triphosphate (ddNTP) analogues, each having the structure:

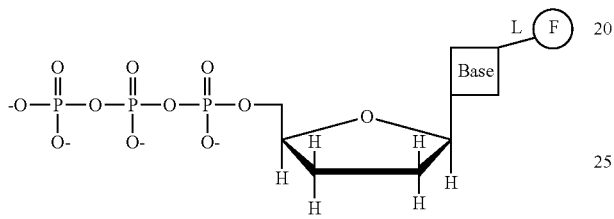

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four ddNTP analogues differs from the remaining three ddNTP analogues by having a different base, wherein L is a cleavable linker molecule, (ii) at least four deoxynucleotide triphosphate (dNTP) analogues having the structure:

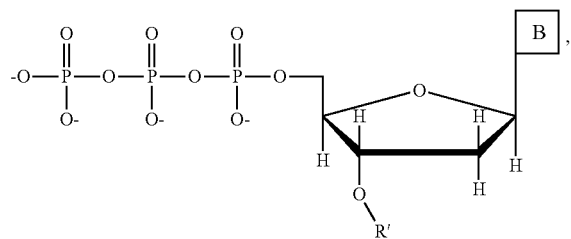

wherein B is a base and is adenine, guanine, cytosine, uracil, or thymine, and wherein R' is a cleavable chemical group, wherein each of the four dNTP analogues differs from the remaining three dNTP analogues by having a different base, and (iii) a nucleic acid polymerase, under conditions permitting (a) one of the four ddNTP analogues that is complementary to the next consecutive nucleotide residue to be identified to form a phosphodiester bond with the 3' end of one of the extended second nucleic acid primers and thereby extend the second primer and (b) one of the four dNTP analogues that is complementary to a consecutive nucleotide residue to be identified to form a phosphodiester bond with the 3' end of another one of the extended second nucleic acid primers and thereby extend that second primer;

k) identifying the fluorophore of the ddNTP analogue which has formed the phosphodiester bond, thereby identifying the consecutive nucleotide;

l) cleaving the linker attaching the fluorophore of the ddNTP analogue which has formed the phosphodiester bond and cleaving the cleavable chemical group from the dNTP which has formed the phosphodiester bond;

m) iteratively repeating steps j) through l) for each of the consecutive nucleotide residues to be identified until the final consecutive nucleotide residue is to be identified;

n) repeating steps j) and k) to identify the final consecutive nucleotide residue, so as to thereby determine the identity of each of the series of consecutive nucleotide residues in the nucleic acid.

In an embodiment the linker in each of step a) and j) independently each comprise the structure:

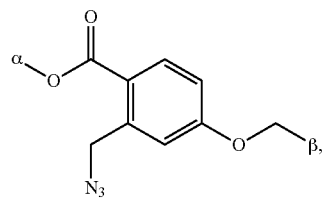

or the structure:

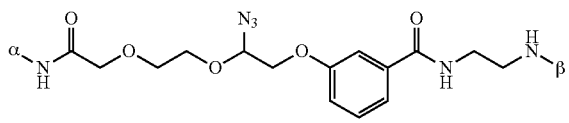

wherein α represents a point of attachment to the base and β represents a point of attachment to the fluorophore, and wherein R is a cleavable chemical group.

In an embodiment a linker is cleaved by contacting the linker with tris(2-carboxyethyl)phosphine.

In an embodiment one or more linkers are photocleavable or chemically cleavable.

In an embodiment one or more chemical groups are photocleavable or chemically cleavable.

In an embodiment R in the structures set forth in steps a) and or j) is independently chosen from a —$N_3$ group or an allyl group.

In an embodiment the cleavable chemical group in step g) is independently chosen from a —$N_3$ group or an allyl group.

A method for determining the identity of each of a series of consecutive nucleotide residues in a nucleic acid comprising:

a) contacting a plurality of the nucleic acids with (i) at least four different dideoxynucleotide triphosphate (ddNTP) analogues, each having the structure:

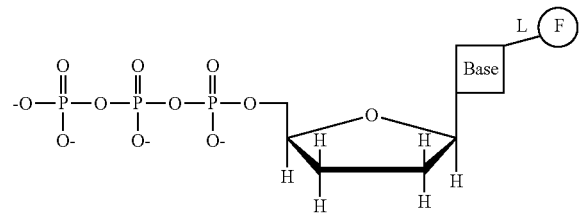

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four ddNTP analogues differs from the remaining three ddNTP analogues by having a different base, wherein L is a cleavable linker molecule, (ii) at least four deoxynucleotide triphosphate (dNTP) analogues having the structure:

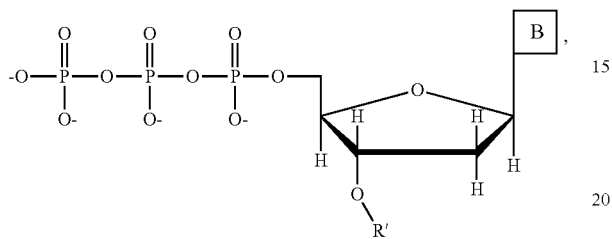

wherein B is a base and is adenine, guanine, cytosine, uracil, or a thymine, and wherein R' is a cleavable chemical group, wherein each of the four dNTP analogues differs from the remaining three dNTP analogues by having a different base, (iii) a nucleic acid polymerase and (iv) a plurality of nucleic acid primers which can each hybridize with a separate one of each of the plurality of nucleic acids,
under conditions permitting (a) one of the four ddNTP analogues that is complementary to the consecutive nucleotide residue to be identified to form a phosphodiester bond with the 3' end of one of the nucleic acid primers and thereby extend the primer and (b) one of the four dNTP analogues that is complementary to a consecutive nucleotide residue to be identified to form a phosphodiester bond with the 3' end of another one of the nucleic acid primers and thereby extend that primer;
b) identifying the fluorophore of the ddNTP analogue which has formed the phosphodiester bond, thereby identifying the consecutive nucleotide;
c) cleaving the linker attaching the fluorophore of the ddNTP analogue which has formed the phosphodiester bond and cleaving the cleavable chemical group from the dNTP which has formed the phosphodiester bond;
d) iteratively repeating steps a) through c) for each of the consecutive nucleotide residues to be identified until the final consecutive nucleotide residue is to be identified;
e) repeating steps a) and b) to identify the final consecutive nucleotide residue,
f) denaturing the extended primers so as to de-hybridize them from the plurality of nucleic acids;
g) contacting the nucleic acids with (i) three different types of deoxynucleotide triphosphate, (ii) a nucleic acid polymerase and (iii) a second plurality of nucleic acid primers which each hybridize with a separate one of the plurality of nucleic acids, under conditions permitting one of the three dNTP analogues that is complementary to the consecutive nucleotide residue to be identified to form a phosphodiester bond with the 3' end of the second nucleic acid primer and thereby extend the second nucleic acid primer;
h) contacting the nucleic acid with (i) three different types of deoxynucleotide triphosphate, wherein at least one of the types of deoxynucleotide triphosphate is not used in step g), under conditions permitting one of the three dNTP that is complementary to the consecutive nucleotide residue to be identified to form a phosphodiester bond with the 3' end of the extended second nucleic acid primer and thereby further extend the second nucleic acid primer;
i) repeating steps g) and h) until the second nucleic acid primer is extended up to and including a residue corresponding to the final consecutive nucleotide residue identified in step e)
j) contacting the plurality of extended second primers with (i) at least four different dideoxynucleotide triphosphate (ddNTP) analogues, each having the structure:

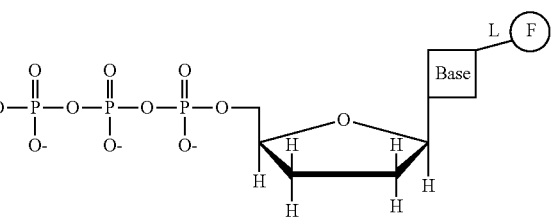

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four ddNTP analogues differs from the remaining three ddNTP analogues by having a different base, wherein L is a cleavable linker molecule, (ii) at least four deoxynucleotide triphosphate (dNTP) analogues having the structure:

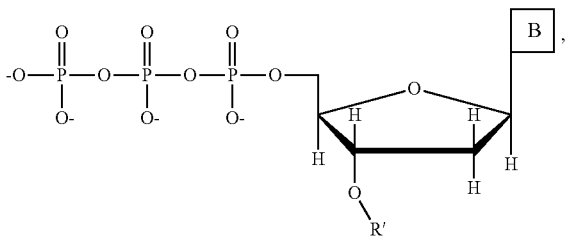

wherein B is a base and is adenine, guanine, cytosine, uracil, or a thymine, and wherein R' is a cleavable chemical group, wherein each of the four dNTP analogues differs from the remaining three dNTP analogues by having a different base, and (iii) a nucleic acid polymerase,
under conditions permitting (a) one of the four ddNTP analogues that is complementary to the consecutive nucleotide residue to be identified to form a phosphodiester bond with the 3' end of one of the extended second nucleic acid primers and thereby extend the second primer and (b) one of the four dNTP analogues that is complementary to a consecutive nucleotide residue to be identified to form a phosphodiester bond with the 3' end of another one of the extended second nucleic acid primers and thereby extend that second primer;
k) identifying the fluorophore of the ddNTP analogue which has formed the phosphodiester bond, thereby identifying the consecutive nucleotide;
l) cleaving the linker attaching the fluorophore of the ddNTP analogue which has formed the phosphodiester bond and cleaving the cleavable chemical group from the dNTP which has formed the phosphodiester bond;

m) iteratively repeating steps j) through l) for each of the consecutive nucleotide residues to be identified until the final consecutive nucleotide residue is to be identified;

n) repeating steps j) and k) to identify the final consecutive nucleotide residue, so as to thereby determine the identity of each of the series of consecutive nucleotide residues in the nucleic acid.

In an embodiment in steps g) and h) the three types of dNTPs are chosen from the group dATP, dCTP, dGTP and dTTP.

In an embodiment the linker in each of step a) and j) independently each comprise the structure:

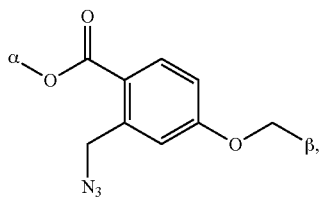

or the structure:

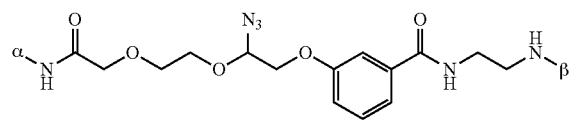

wherein α represents a point of attachment to the base and β represents a point of attachment to the fluorophore, and wherein R is a cleavable chemical group.

In an embodiment a linker is cleaved by contacting the linker with tris(2-carboxyethyl)phosphine.

In an embodiment one or more linkers are photocleavable or chemically cleavable.

In an embodiment one or more chemical groups are photocleavable or chemically cleavable.

In an embodiment R in the structures set forth in steps a) and or j) is independently chosen from a —N$_3$ group or an allyl group.

In an embodiment the cleavable chemical group in step g) is independently chosen from a —N$_3$ group or an allyl group.

A method for determining the identity of each of a series of consecutive nucleotide residues in a nucleic acid comprising:

a) contacting a plurality of the nucleic acids with (i) at least four different dideoxynucleotide triphosphate (ddNTP) analogues, each having the structure:

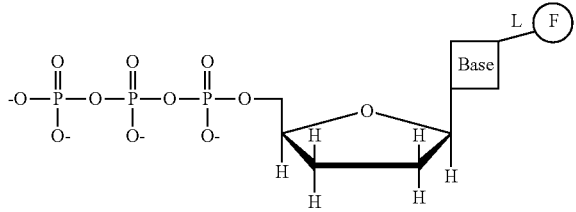

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four ddNTP analogues differs from the remaining three ddNTP analogues by having a different base, wherein L is a cleavable linker molecule, (ii) at least four deoxynucleotide triphosphate (dNTP) analogues having the structure:

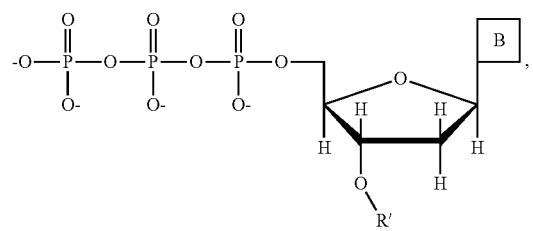

wherein B is a base and is adenine, guanine, cytosine, uracil, or a thymine, and wherein R' is a cleavable chemical group, wherein each of the four dNTP analogues differs from the remaining three dNTP analogues by having a different base, (iii) a nucleic acid polymerase and (iv) a plurality of nucleic acid primers which can each hybridize with a separate one of each of the plurality of nucleic acids, under conditions permitting (a) one of the four ddNTP analogues that is complementary to the consecutive nucleotide residue to be identified to form a phosphodiester bond with the 3' end of one of the nucleic acid primers and thereby extend the primer and (b) one of the four dNTP analogues that is complementary to a consecutive nucleotide residue to be identified to form a phosphodiester bond with the 3' end of another one of the nucleic acid primers and thereby extend that primer;

b) identifying the fluorophore of the ddNTP analogue which has formed the phosphodiester bond, thereby identifying the consecutive nucleotide;

c) cleaving the linker attaching the fluorophore of the ddNTP analogue which has formed the phosphodiester bond and cleaving the cleavable chemical group from the dNTP which has formed the phosphodiester bond;

d) iteratively repeating steps a) through c) for each of the consecutive nucleotide residues to be identified until the final consecutive nucleotide residue is to be identified;

e) repeating steps a) and b) to identify the final consecutive nucleotide residue, f) denaturing the extended primers so as to de-hybridize them from the plurality of nucleic acids;

g) contacting the nucleic acid with (i) three different types of deoxynucleotide triphosphates, (ii) a deoxynucleotide triphosphate analogue, differing from a deoxynucleotide triphosphate by having a cleavable chemical group attached to the 3' O-atom of the dNTP analogue and differing from the three different types of deoxynucleotide triphosphates by having a different base therefrom, (iii) a nucleic acid polymerase and (iv) a second nucleic acid primer which hybridizes with the nucleic acid, under conditions permitting one of the three dNTPs or the dNTP analogue that is complementary to the consecutive nucleotide residue to be identified to form a phosphodiester bond with the 3' end of one of the second nucleic acid primers and thereby extend that second nucleic acid primer;

h) cleaving the cleavable chemical group from the 3'-O-atom group;
i) repeating steps g) and h) until the second nucleic acid primer is extended up to and including a residue corresponding to the final consecutive nucleotide residue identified in step e)
j) contacting the plurality of extended second primers with (i) at least four different dideoxynucleotide triphosphate (ddNTP) analogues, each having the structure:

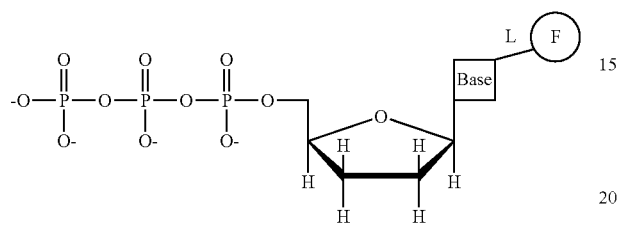

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four ddNTP analogues differs from the remaining three ddNTP analogues by having a different base, wherein L is a cleavable linker molecule, (ii) at least four deoxynucleotide triphosphate (dNTP) analogues having the structure:

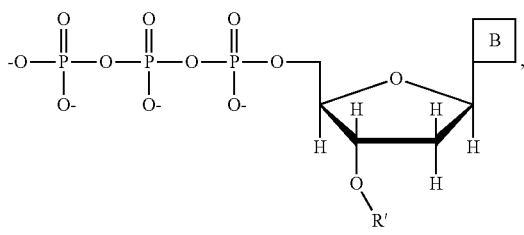

wherein B is a base and is adenine, guanine, cytosine, uracil, or thymine, and wherein R' is a cleavable chemical group, wherein each of the four dNTP analogues differs from the remaining three dNTP analogues by having a different base, and (iii) a nucleic acid polymerase,
under conditions permitting (a) one of the four ddNTP analogues that is complementary to the consecutive nucleotide residue to be identified to form a phosphodiester bond with the 3' end of one of the extended second nucleic acid primers and thereby extend the second primer and (b) one of the four dNTP analogues that is complementary to a consecutive nucleotide residue to be identified to form a phosphodiester bond with the 3' end of another one of the extended second nucleic acid primers and thereby extend that second primer;
k) identifying the fluorophore of the ddNTP analogue which has formed the phosphodiester bond, thereby identifying the consecutive nucleotide;
l) cleaving the linker attaching the fluorophore of the ddNTP analogue which has formed the phosphodiester bond and cleaving the cleavable chemical group from the dNTP which has formed the phosphodiester bond;

m) iteratively repeating steps j) through h) for each of the consecutive nucleotide residues to be identified until the final consecutive nucleotide residue is to be identified;
n) repeating steps j) and k) to identify the final consecutive nucleotide residue,
so as to thereby determine the identity of each of the series of consecutive nucleotide residues in the nucleic acid.
In an embodiment in step c) the three types of dNTPs are chosen from the group dATP, dCTP, dGTP and dTTP.
In an embodiment the linker in each of step a) and f) independently each comprise the structure:

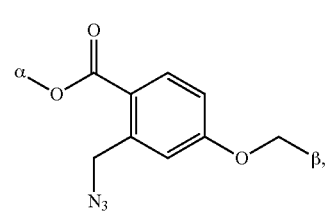

or the structure:

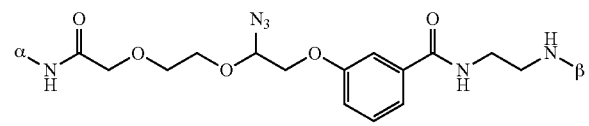

wherein α represents a point of attachment to the base and β represents a point of attachment to the fluorophore, and wherein R is a cleavable chemical group.
In an embodiment a linker is cleaved by contacting the linker with tris(2-carboxyethyl)phosphine.
In an embodiment one or more linkers are photocleavable or chemically cleavable.
In an embodiment one or more chemical groups are photocleavable or chemically cleavable.
In an embodiment R in the structures set forth in steps a) and or f) is independently chosen from a —$N_3$ group or an allyl group.
In an embodiment the cleavable chemical group in step f) is independently chosen from a —$N_3$ group or an allyl group.
In an embodiment the first and second plurality of primers have the same sequence.
In an embodiment one or more washing steps are performed in between one or more of the steps set forth.
The methods described herein can be applied mutatis mutandis to sequencing RNA using the appropriate ddNTPS or analogues thereof and dNTPS and analogues thereof.
In the methods, base-pairing complementarity allows the sequence of the extended primer or of the target nucleic to be readily determined.
Dehybridize is understood by those skilled in the art to mean to disassociate the hybridized primer (or extended strand thereof) from the target nucleic acid without destroying the target nucleic acid and thus permitting further hybridization of a second primer to the target nucleic acid. Hybridization as used herein in one embodiment means stringent hybridization, for examples as described in Sambrook, J., Russell, D. W., (2000) Molecular Cloning: A Laboratory Manual: Third Edition. Cold Spring Harbor Laboratory Press "Type" of dNTP or ddNTP is used to distinguish dNTP or ddNTPs comprising different bases.

All combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

Experimental Details

Here, an alternative sequencing method that is a hybrid between Sanger dideoxy chain terminating reaction and sequencing by synthesis (SBS) is disclosed and some advantages that come with this hybrid sequencing approach are discussed. The fundamental difference between the two methods is that that the Sanger approach produces all possible complementary DNA extension fragments for a given DNA template and obtains the sequence after the separation of these fragments by reading the fluorescent labeled terminated base, while SBS relies on identification of each base as the DNA strand is synthesized by utilizing fluorescent labeled modified nucleotides that temporarily pauses the DNA synthesis for base identification. The limiting factors for increasing sequencing throughput in Sanger based method, as mentioned previously, is in the DNA separation using electrophoresis and limited parallelization of the capillaries. Concerns using SBS with labeled modified nucleotides lie on base modification where the labels are attached, and the fact that after cleavage of the label there may still remain a small trace of modification. This can affect the 3-D double helix structure of the DNA and, furthermore, the ability of DNA polymerase to bind to the double stranded DNA and efficiently incorporate the incoming nucleotide. The advantage in the Sanger based method is clearly in the Sanger dideoxy chain fragment producing reaction. It is a simple reaction, where DNA extensions are made with natural nucleotides. When the fluorescent labeled dideoxynucleotides are incorporated into a DNA strand, it no longer is involved in further DNA extension reactions. Therefore, the DNA polymerase extension reaction occurs with only natural substrates, and the efficiency of this reaction is clearly evident by its long read-length. The most attractive features in the SBS sequencing approach are the potentially massive parallel readout capability via high-density microarray and simplified sample preparation method. The integration of the advantageous features between the two methods to develop a hybrid DNA sequencing approach has been explored. The key molecular inventions suitable for the proposed hybrid DNA sequencing approach are rationally modified nucleotide and dideoxynucleotide analogue sets, which will allow generation of Sanger sequencing fragments on a DNA chip to produce sequencing data, thus bypassing the electrophoresis DNA separation steps.

Previous research efforts have firmly established the molecular level strategy to rationally modify the nucleotides by attaching a cleavable fluorophore to the base and capping the 3'-OH with a small capping moiety for SBS. Here, the design and synthesis of four photocleavable fluorescent dideoxynucleotides and four photocleavable nucleotide analogues as reversible terminators is disclosed for Sanger/SBS hybrid sequencing approach. Each of the four photocleavable dideoxynucleotide analogues contains a unique fluorophore with a distinct fluorescence emission at the base through a photocleavable linker. The four photocleavable reversible terminator nucleotides contain, in an embodiment, a 3'-O-(2-nitrobenzyl) group, which caps the 3'-OH on the sugar ring. It was first established that these dideoxynucleotide and nucleotide analogues are good substrates for DNA polymerase in a solution-phase DNA extension reaction and that the fluorophore and the 3'-O-(2-nitrobenzyl) group can be removed with high efficiency via laser irradiation at 355 nm in 10 sec. SBS was then performed using the combination mixture (such as in Sanger dideoxy chain termination reaction) of these 4 photocleavable fluorescent dideoxynucleotide analogues and 4 photocleavable 3'-O-modified reversible terminator nucleotides to accurately identify continuous bases of a DNA template immobilized on a chip. These results indicated that these photocleavable fluorescent dideoxynucleotides and photocleavable 3'-O-modified reversible terminator nucleotides can be rationally designed by attaching a cleavable fluorophore to the base of dideoxynucleotides and capping the 3'-OH with a small reversible moiety to the natural nucleotides so that they are still recognized by DNA polymerase as substrates. Furthermore, these analogues can generate 4-color DNA sequencing data by producing Sanger sequencing fragments on a sequencing by synthesis platform.

A modified inosine triphosphate (having a cleavable group attached to the 3' O atom thereof) is used in the Sanger/sequencing by synthesis hybrid method to increase readlength and/or simplify the procedure. The dITP is used in conjunction with the ddNTPs, and as universal nucleotide can extend the nucleic acid by being complementary to any of the four natural nucleotides in the nucleic acid being sequenced.

Sequence by Synthesis with Template "Walking"

The fundamental rationale behind primer resetting is to regenerate the original primer site or to insert two or more primer sites of known sequences into the target DNA so SBS can be carried out at each site sequentially. In general, three steps are involved with this approach: 1) annealing of the first primer, 2) performing SBS, 3) denaturing the sequenced section of the template to recover a single-stranded DNA for the second primer annealing. These steps are carried out repeatedly until the target DNA is sequenced in its entirety. The advantage of primer resetting lies in its ability to restore all the templates after the denaturation step, including those that are terminated with ddNTPs, so the next cycle of SBS can restart with potentially the same amount of sequenceable DNA as the previous round.

Three approaches for achieving longer read lengths that rely on this template "walking" concept are described. In the first strategy, the DNA sequence is reset by reattaching the original primer, extending the chain with natural or minimally modified nucleotides to the end of the first round sequence, and then sequencing from that point. The second strategy relies on annealing of a second round primer that is longer than the first, containing at its 5' end the same sequence as the original primer, followed by a run of 20 universal nucleotides such as inosine, from which the second round of sequencing can be primed. If the duplex stability of this highly degenerate primer with DNA templates is found to be low, a number of locked nucleotides can be added at either end of the primer to increase the stability of the primer-template complex. In the third strategy, extra priming sites are inserted within a template strand via Type IIS or Type III restriction-recircularization. Each of these approaches has distinct advantages and some difficulties that need to be overcome. None of the three aforementioned strategies are sensitive to the type of library (genomic, cDNA or other), to the method of amplification prior to sequencing (spotting of clones, ePCR, polony PCR), or the mode of sequencing (Hybrid SBS and SBS with C—F-NRTs). Hence they are all sequence unbiased, thus greatly increasing their range of applications in sequencing technologies.

Results

Design and Synthesis of Photocleavable Fluorescent Dideoxyribonucleotides for SBS.

To demonstrate the feasibility of carrying out de novo DNA sequencing by synthesis on a chip, four photocleavable fluorescent dideoxynucleotide analogues (ddCTP-PC-Bodipy-FL-510, ddUTP-PC-R6G, ddATP-PC-ROX and ddGTP-PC-Bodipy-650) (FIG. 1) were designed and synthesized as fluorescent terminators for DNA polymerase reaction. Modified DNA polymerases have been shown to be highly tolerant to nucleotide modifications with bulky groups at the 5-position of pyrimidines (C and U) and the 7-position of purines (A and G). Thus, each unique fluorophore was attached to the 5 position of C/U and the 7 position of A/G through a 2-nitrobenzyl linker. It was found that the fluorophore on a DNA extension product, which is generated by incorporation of the photocleavable fluorescent dideoxynucleotide analogues, are removed by 10 sec irradiation of the DNA extension product at 355 nm in aqueous solution. This rapid photocleavage reaction thus allows quantitative removal of the fluorophore after the DNA extension reaction. The detailed synthesis procedure and characterization of the 4 novel dideoxynucleotide analogues in FIG. 1 are described in Supporting materials and methods.

Figure 2:
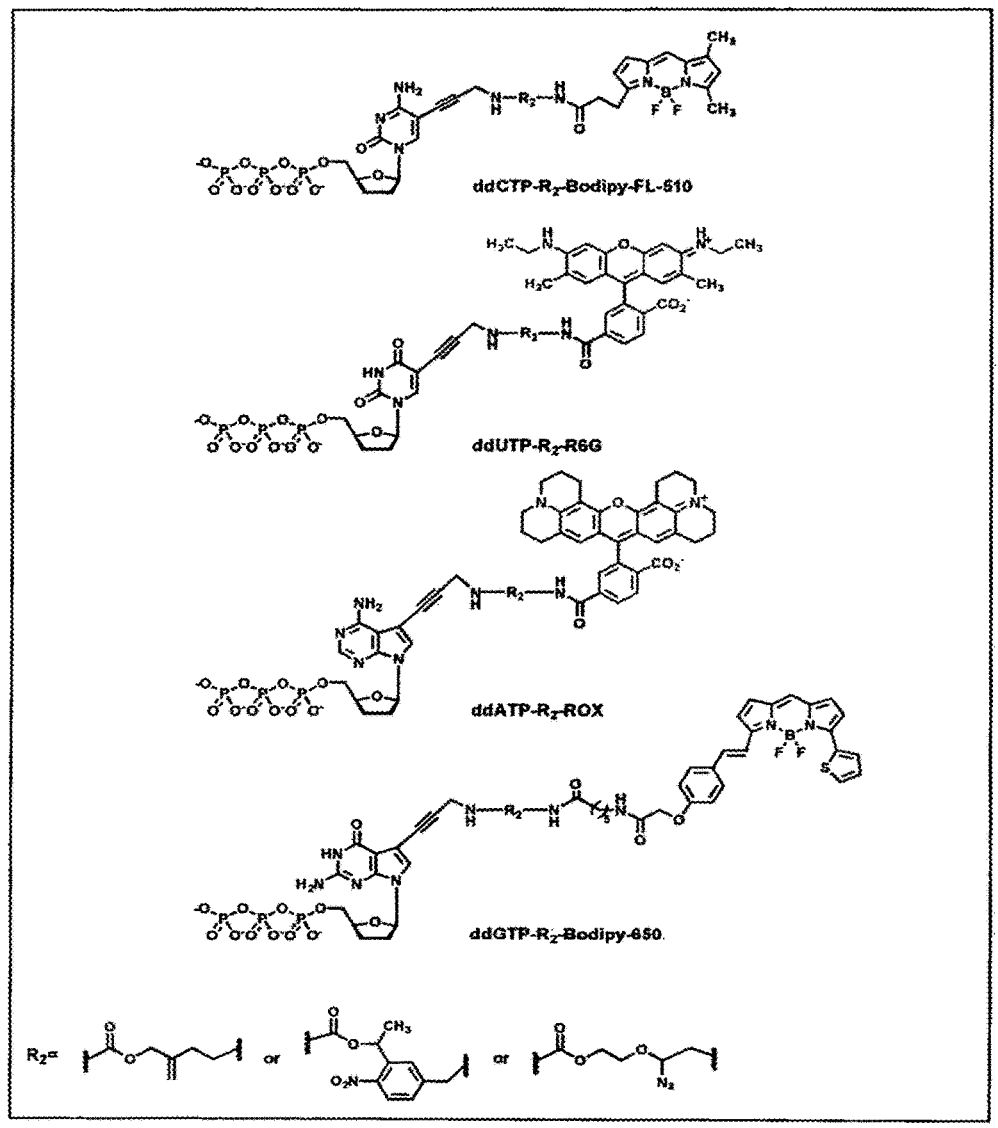
FIG. 2. Structures of ddNTPs-$R_2$-fluorophore, with the 4 fluorophores having distinct fluorescent emissions: ddCTP-$R_2$-Bodipy-FL-510 (λabs (max)=502 nm; λem (max)=510 nm), ddUTP-$R_2$-R6G (λabs (max)=525 nm; λem (max)=550 nm), ddATP-$R_2$-ROX (λabs (max)=575 nm; λem (max)=602 nm), and ddGTP-$R_2$-Bodipy-650 (λabs (max)=630 nm; λem (max)=650 nm).

The efficient removal of the fluorophore from the DNA after detection is crucial for the SBS approach. Four photocleavable fluorescent dideoxynucleotides (FIG. 1) were synthesized and demonstrated that 10 seconds of irradiation with a laser at 355 nm led to the complete photocleavage of the fluorophore from the DNA. These nucleotide analogues were characterized by using them in a single base extension reaction and investigating the photocleavage of the fluorophore by UV irradiation. In order to verify that these fluorescent dideoxynucleotide analogues are incorporated accurately in a base-specific manner in a polymerase reaction, four separate DNA extensions and photocleavage via UV irradiation were carried out in solution. This allows the isolation of the DNA product at each step for detailed molecular structure characterization by MALDI-TOF mass spectrometry (MS) as shown in FIG. 2. The first extension product 5'-primer-A(PC-ROX)-3' (1) was purified by HPLC and analyzed using MALDI-TOF MS [FIG. 2(A)]. This product was then irradiated at 355 nm using an Nd-YAG laser for 10 seconds and the photocleavage product was also analyzed using MALDI-TOF MS (FIG. 2(B)). The UV absorption by the aromatic 2-nitrobenzyl linker causes reduction of the 2-nitro group to a nitroso group and an oxygen insertion into the carbon-hydrogen bond located in the 2-position followed by cleavage and decarboxylation. As can be seen from FIG. 2(A), the MALDI-TOF MS spectrum consist of a distinct peak corresponding to the DNA extension product 5'-primer-A(PC-ROX)-3' (m/z 9054), which confirms that the dideoxynucleotide analogue can be incorporated base specifically by DNA polymerase into a growing DNA strand. The small peak at m/z 8315 corresponding to the photocleavage product is seen due to the partial cleavage caused by the nitrogen laser pulse (337 nm) used in MALDI ionization. For the photocleavage experiment, near UV-irradiation at 355 nm by a laser was used for 10 seconds to cleave off the fluorophore from the DNA extension product. FIG. 2(B) shows the photocleavage result of the extension products. The extended mass peak at m/z 9054 completely disappeared while the peak corresponding to the photocleavage product 5'-primer-A appear as the sole dominant peak at m/z 8315, which establishes that laser irradiation completely cleaves the fluorophore with high speed and efficiency. DNA extension reactions using self-priming templates that incorporates the other three fluorescent dideoxynucleotide analogues as the first base were similarly carried out. As described above, the extension product 5'-primer-C(PC-Bodipy-FL-510)-3' (FIG. 2(C)) was purified and analyzed by MALDI-TOF MS, then photocleaved (FIG. 2(D)) for further MS analysis. Extension products 5'-primer-G(PC-Bodipy-650)-3' (FIG. 2(E)), 5'-primer-U(PC-R6G)-3' (FIG. 2(G)) and their photocleavage to yield products 6 (FIG. 2(F)) and 8 (FIG. 2(H)) were similarly carried out and analyzed by MALDI-TOF MS. These results demonstrate that all four photocleavable fluorescent dideoxynucleotide analogues were correctly synthesized and successfully incorporated into the growing DNA strand in a polymerase reaction and the fluorophore can be efficiently cleaved by near UV irradiation, which makes it feasible to use these nucleotide analogues for SBS on a chip.

Design and Synthesis of 3'-Modified Photocleavable Nucleotides as Reversible Terminators for SBS.

A critical requirement for using SBS methods to sequence DNA unambiguously is a suitable chemical moiety to cap the 3'-OH of the nucleotide such that it terminates the polymerase reaction to allow the identification of the incorporated nucleotide. A stepwise separate addition of nucleotides with a free 3'-OH group has inherent difficulties in detecting sequences in homopolymeric regions. A 3'-OH capping group of the nucleotides allows for the addition of all four nucleotides simultaneously in performing SBS. This will decrease the number of cycles needed for sequencing with the requirement that the capping group then needs to be efficiently removed to regenerate the 3'-OH thereby allowing the polymerase reaction to proceed.

Figure 3:
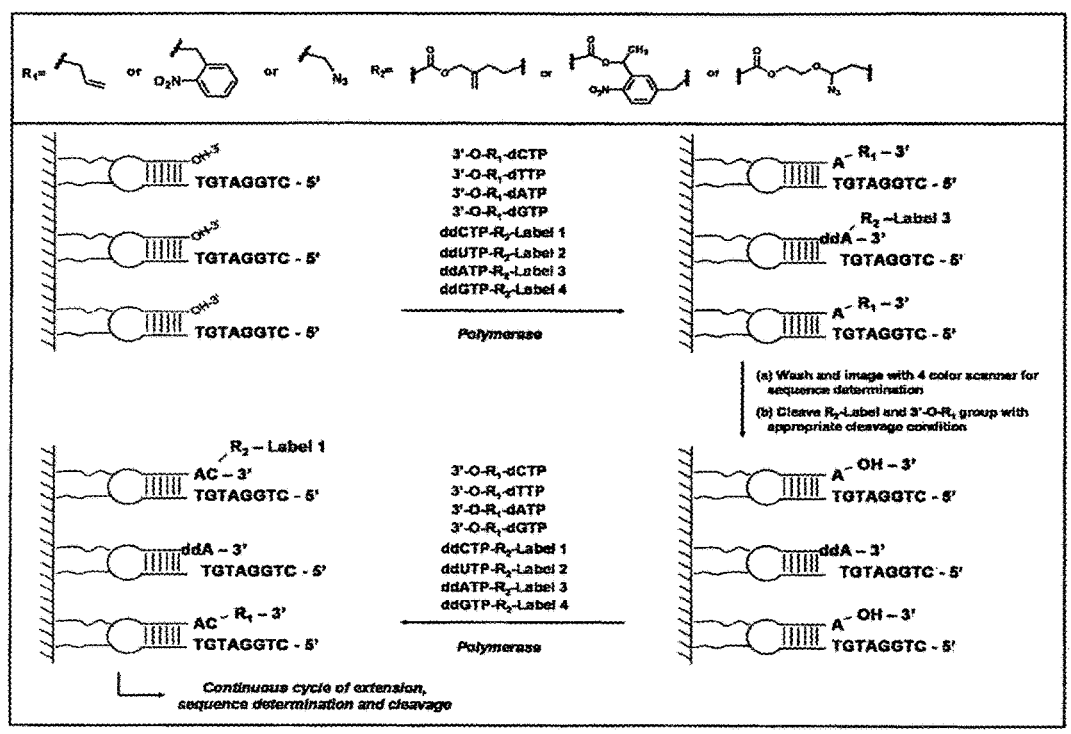
FIG. 3. Reaction scheme of sequencing on a chip using combination of 3'-O-modified nucleotide reversible terminators (3'-O—$R_1$-dNTPs) and cleavable label modified dideoxynucleotide terminators (ddNTPs-$R_2$-label). In this sequencing approach, a chip is constructed with immobilized DNA templates that are able to self-prime for initiating the polymerase reaction. Four cleavable label modified dideoxynucleotides are designed such that each is attached with a unique label on the base through a cleavable linker ($R_2$). The four 3'-O-modified nucleotides have a small chemically reversible group ($R_1$) to cap the 3'-OH moiety. Upon adding the mixture of 3'-O—$R_1$-dNTPs and ddNTPs-$R_2$-label with the DNA polymerase, only the dideoxynucleotide/nucleotide analogue complementary to the next nucleotide on the template is incorporated by polymerase on each spot of the chip. The ratio of the two sets of nucleotides are tuned so that in each extension step, only a small amount of the labeled ddNTPs are incorporated into the self-priming DNA template to produce adequate signal for detection, while the rest are incorporated by the nucleotide reversible terminators. After removing the excess reagents and washing away any unincorporated dideoxynucleotide/nucleotide analogues, a 4 color fluorescence imager (if the label is a fluorescent dye) is used to image the surface of the chip, and the unique fluorescence emission from the specific fluorescent dye on the dideoxynucleotide analogues on each spot of the chip will yield the identity of the nucleotide. After imaging, the $R_2$-label and the $R_1$ protecting group will be removed by appropriate cleavage conditions to generate DNA products with the label removed and a free 3'-OH group with high yield, respectively. The self-primed DNA moiety on the chip at this stage is ready for the next cycle of the reaction to identify the next nucleotide sequence of the template DNA. The scheme may be performed mutatis mutandis for RNA, and may also be performed with a non-self-priming nucleic acid if primers are included in the reaction conditions.
Figure 4:
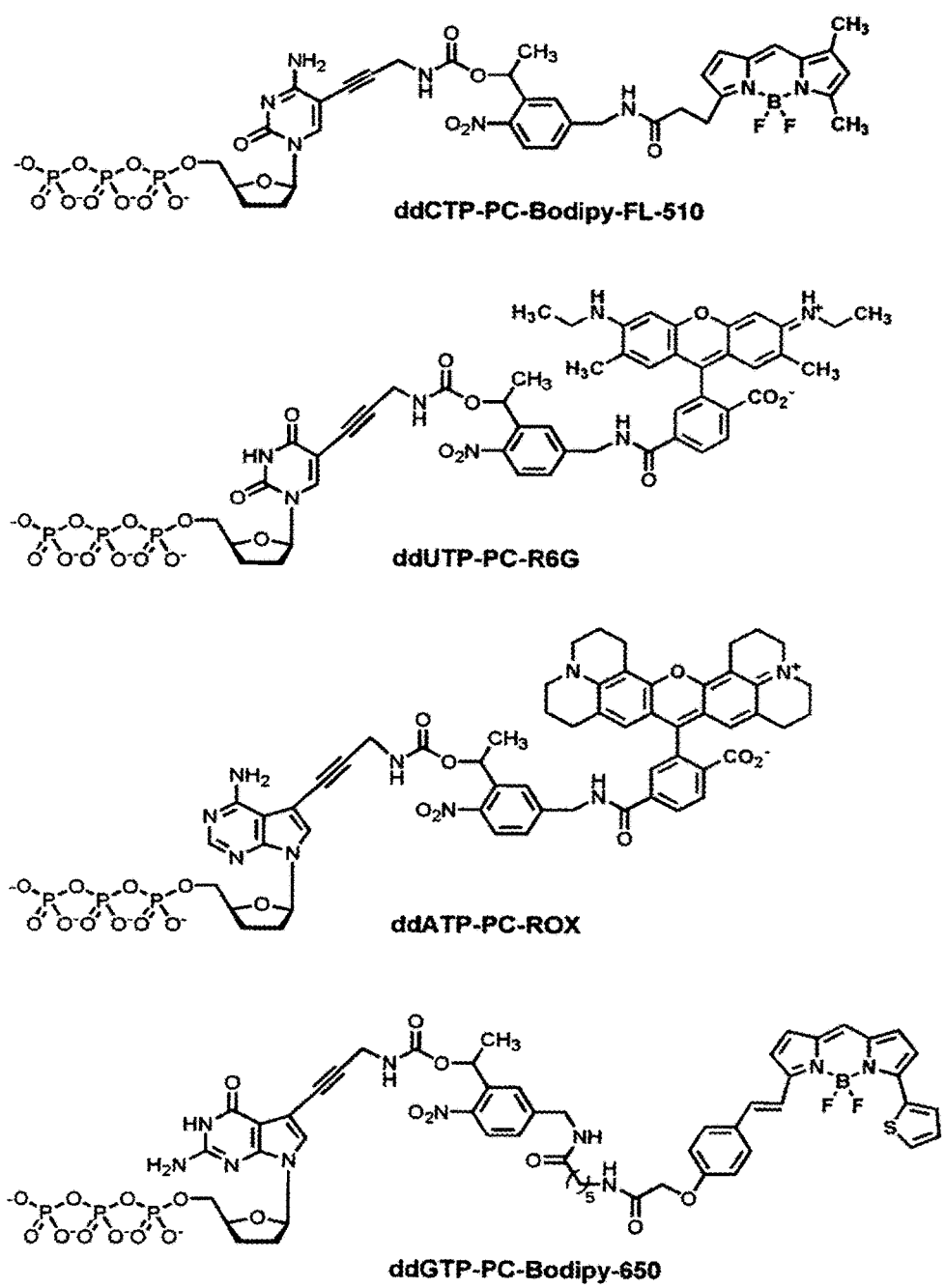
FIG. 4. Exemplified structures of ddNTPs having photocleavably linked fluorophores (ddNTPs-PC-fluorophore), with the 4 fluorophores having distinct fluorescent emissions: ddCTP-PC-Bodipy-FL-510 (λabs (max)=502 nm; λem (max)=510 nm), ddUTP-PC-R6G (λabs (max)=525 nm; λem (max)=550 nm), ddATP-PC-ROX (λabs (max)=575 nm; λem (max)=602 nm), and ddGTP-PC-Bodipy-650 (λabs (max)=630 nm; λem (max)=650 nm).

Four 3'-modified photocleavable nucleotides (3'-O-PC-dATP, 3'-O-PC-dCTP, 3'-O-PC-dGTP and 3'-O-PC-dTTP) as reversible terminators (FIG. 3) were synthesized and demonstrated that 10 seconds of irradiation with a laser at 355 nm led to the complete removal of the 3'-OH capping group (2-nitrobenzyl) from the DNA, thereby regenerating a free 3'-OH group for subsequent polymerase reaction. In order to verify that these fluorescent nucleotides incorporate accurately in a base specific manner, four continuous DNA extension reaction and photocleavage via UV irradiation were carried out in solution phase. This allowed the isolation of the DNA product at each step for detailed molecular structure characterization as shown in FIG. 4. The first extension product 5'-primer-T-3'-PC was purified by HPLC and analyzed using MALDI-TOF MS (FIG. 4(A)). This product was then irradiated at 355 nm using a laser for 10 seconds and the photocleavage product was also analyzed using MALDI-TOF MS (FIG. 4(B)). As can be seen from FIG. 4(A), the MALDI-TOF MS spectrum consist of a distinct peak corresponding to the DNA extension product 5'-primer-T-3'-PC (m/z 5965), which confirms that the nucleotide analogue can be incorporated base specifically by DNA polymerase into a growing DNA strand. The small peak at m/z 5830 corresponding to the photocleavage product is seen due to the partial cleavage caused by the nitrogen laser pulse (337 nm) used in MALDI ionization. FIG. 4(B) shows the photocleavage result on the extension product. The extended mass peak at m/z 5965 completely disappeared while the peak corresponding to the photocleavage product 5'-primer-T appear as the sole dominant peak at m/z 5830, which establishes that laser irradiation completely cleaves the 3'-OH capping group with high speed and efficiency. The next extension reaction was carried out using this photocleaved product, which now has a free 3'-OH group, as a primer to give a second extension product, 5'-primer-TG-3'-PC (FIG. 4(C)). As described above, the extension product was purified and analyzed by MALDI-TOF MS, then photocleaved (FIG. 4(D)) for further MS analysis. The third extension reaction to yield 5'-primer-UGA-3'-PC (FIG. 4(E)), the fourth extension to yield 5'-primer-UGAC-3'-PC (FIG. 4(G)) and their photocleavage to yield products 6 (FIG. 4(F)) and 8 (FIG. 4(H)) were similarly carried out and analyzed by MALDI-TOF MS. These results demonstrate that all four 3'-modified photocleavable nucleotide analogues were successfully incorporated into the growing DNA strand in a continuous polymerase reaction as reversible terminators and the 3'-OH capping group was efficiently cleaved by near UV irradiation.

4-Color DNA Sequencing by Synthesis on a Chip Using Photocleavable Fluorescent Dideoxynucleotide/3'-Modified Photocleavable Nucleotide Combination Remnant of Sanger Sequencing.

The combination of photocleavable fluorescent ddNTPs and 3'-modified photocleavable dNTPs were then used in an SBS reaction to identify the sequence of the DNA template immobilized on a solid surface. A site-specific 1,3-dipolar cycloaddition coupling chemistry was used to covalently immobilize the alkyne-labeled self-priming DNA template on the azido-functionalized surface in the presence of a Cu(I) catalyst. The principal advantage offered by the use of a self-priming moiety as compared to using separate primers and templates is that the covalent linkage of the primer to the template in the self-priming moiety prevents any possible dissociation of the primer from the template during the process of SBS. To prevent non-specific absorption of the unincorporated fluorescent nucleotides on the surface of the chip, a polyethylene glycol (PEG) linker is introduced between the DNA templates and the chip surface. This approach was shown to produce very low background fluorescence after cleavage to remove the fluorophore as demonstrated by the DNA sequencing data described below.

Figure 5:
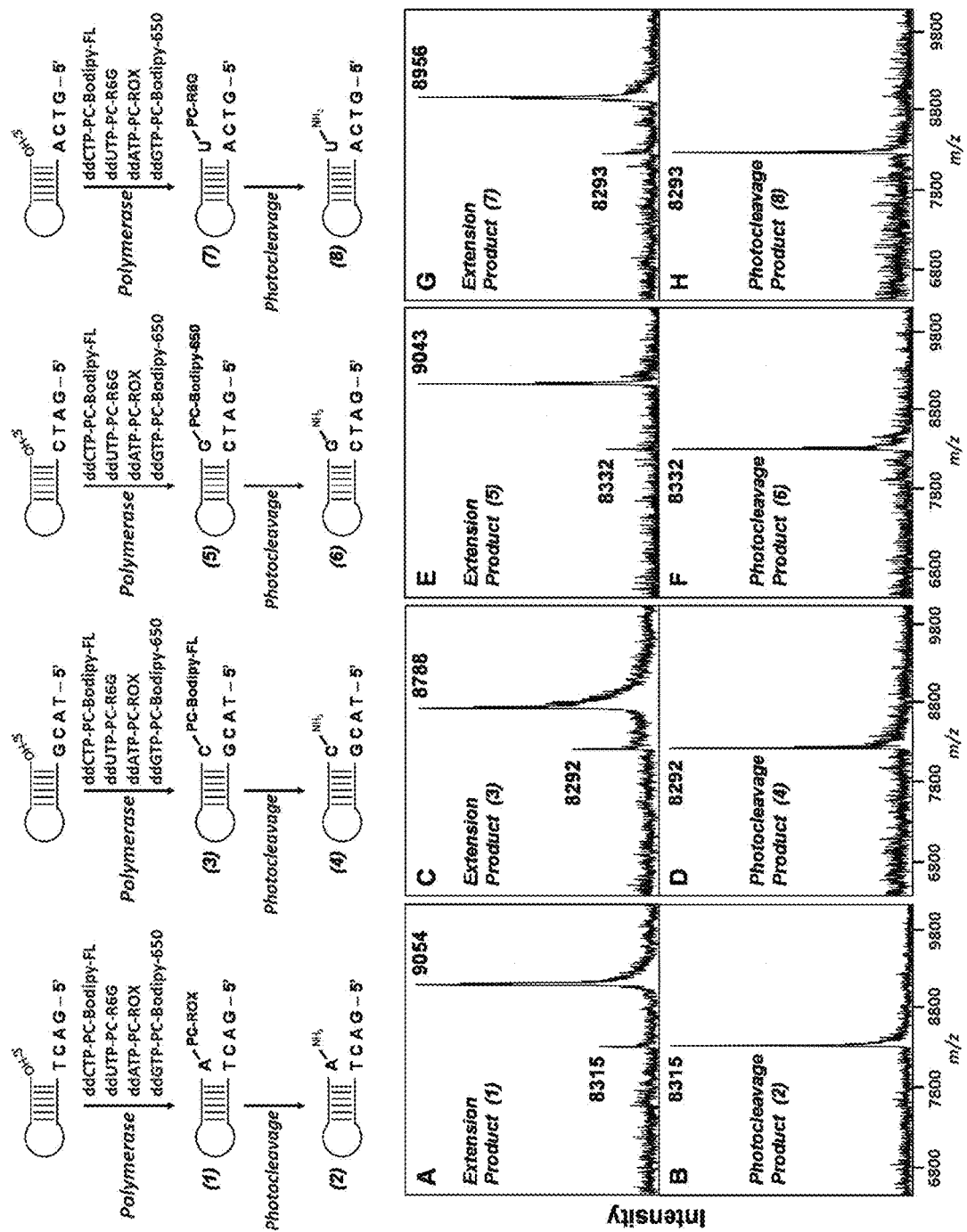
FIG. 5. A detailed scheme (top half of fig.) of polymerase reaction using all four photocleavable fluorescent dideoxynucleotides to extend with an "ddA", "ddC", "ddG" and "ddU" and the subsequent photocleavage reaction to cleave off the fluorophore from the DNA extension product. MALDI-TOF MS spectra (bottom half of fig.) verifying base specific incorporation of: (A) ddATP-PC-ROX (peak at 9,054 m/z) among pool of all four photocleavable fluorescent dideoxynucleotides, (B) the corresponding photocleavage product (8,315 m/z); (C) ddCTP-PC-Bodipy-FL-510 (peak at 8,788 m/z), (D) the corresponding photocleavage product (8,292 m/z); (E) ddGTP-PC-Bodipy-650 (peak at 9,043 m/z), (F) the corresponding photocleavage product (8,332 m/z); (G) ddUTP-PC-R6G (peak at 8,956 m/z) and (H) the corresponding photocleavage product (8,293 m/z).
Figure 6:
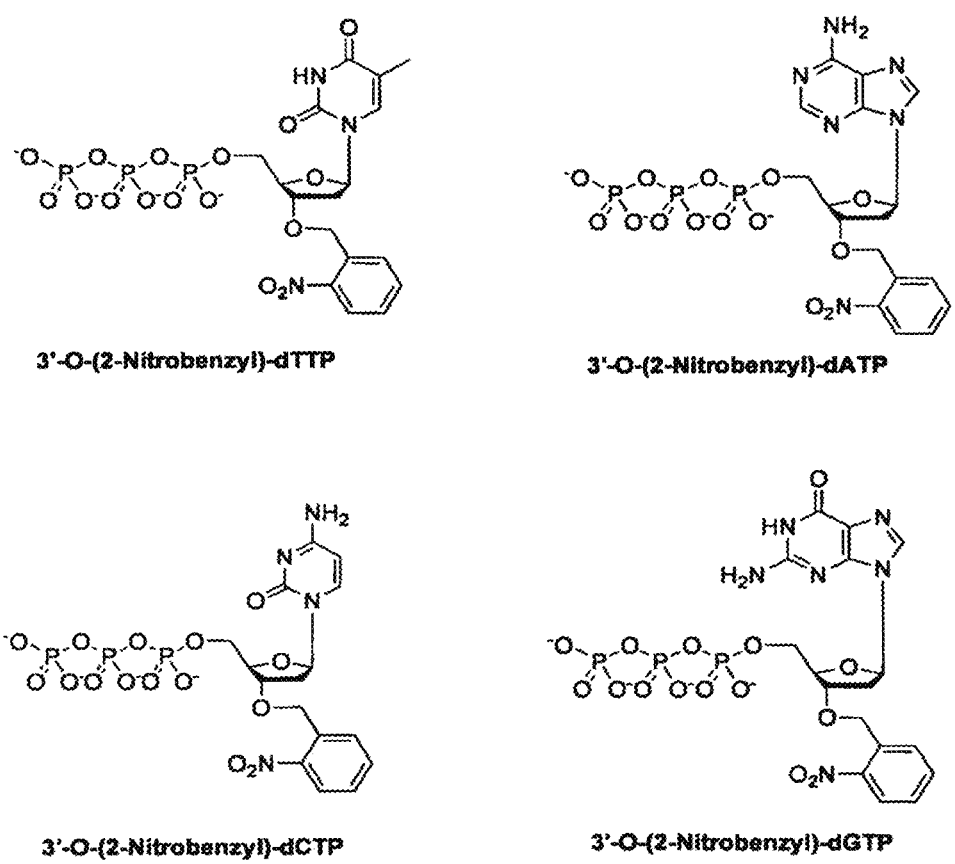
FIG. 6. Structures of photocleavable dNTPs; exemplified are 3'-O-PC-dATP, 3'-O-PC-dCTP, 3'-O-PC-dGTP, and 3'-O-PC-dTTP.
Figure 7:
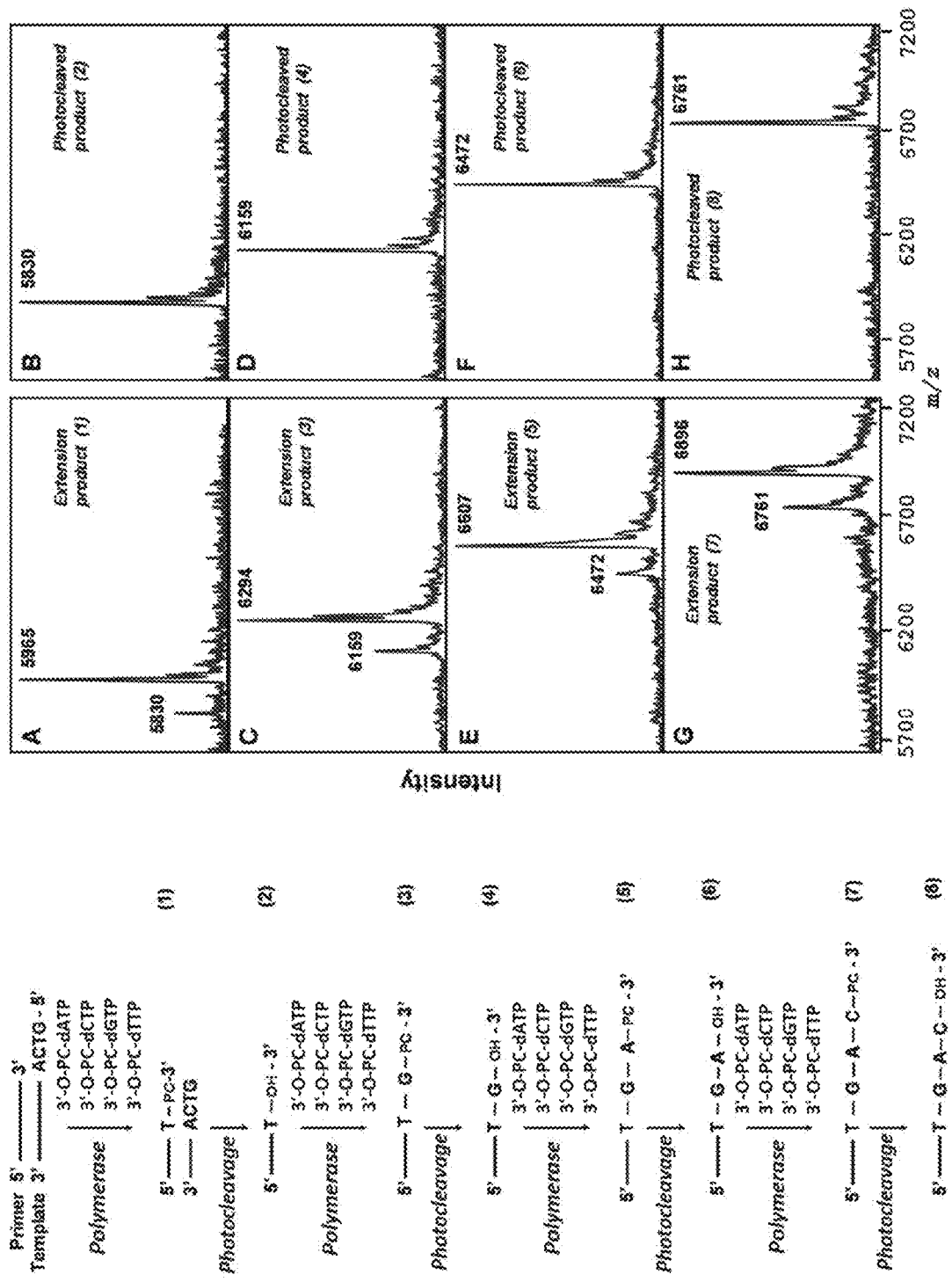
FIG. 7. The polymerase extension scheme (left hand side of Fig.) and MALDI-TOF MS spectra of the four consecutive extension products and their photocleaved products (right hand side of Fig.). Primer extended with 3'-O-PC-dTTP (1), and its photocleaved product 2; Product 2 extended with 3'-O-PC-dGTP (3), and its photocleaved product 4; Product 4 extended with 3'-O-PC-dATP (5), and its photocleaved product 6; Product 6 extended with 3'-O-PC-dCTP (7), and its photocleaved product 8. After 10 seconds of irradiation at 355 nm the photocleavage is complete with the 3'-O-(2-nitrobenzyl) group cleaved from the extended DNA products.
Figure 8:
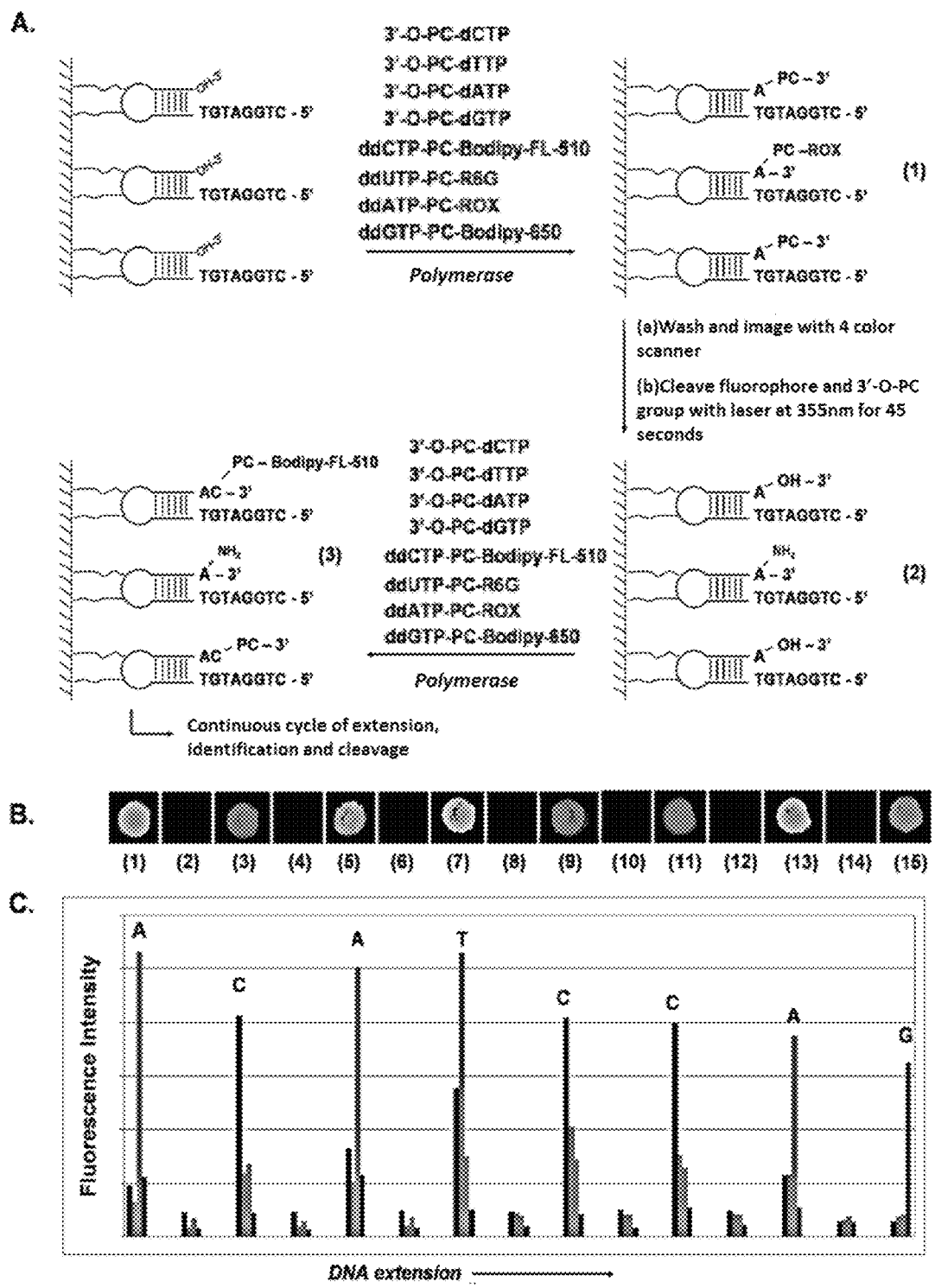
FIG. 8. (A) Reaction scheme of Sanger/sequencing by synthesis hybrid sequencing on a chip using combination of photocleavable fluorescent dideoxynucleotides and 3'-O-PC-modified nucleotides. (B) The scanned 4-color fluorescence images (shown here in grayscale) for each step of Sanger/SBS hybrid sequencing on a chip: (1) incorporation of ddATP-PC-ROX and 3'-O-PC-dATP; (2) cleavage of PC-ROX and 3'-PC group; (3) incorporation of ddCTP-PC-Bodipy-FL-510 and 3'-O-PC-dCTP; (4) cleavage of PC-Bodipy-FL-510 and 3'-PC group; (5) incorporation of ddATP-PC-ROX and 3'-O-PC-dATP; (6) cleavage of PC-ROX and 3'-PC group; (7) incorporation of ddUTP-PC-R6G and 3'-O-PC-dTTP; (8) cleavage of PC-R6G and 3'-PC group; images (9) to (15) are similarly produced. (C) A plot (4-color sequencing data) of raw fluorescence emission intensity at the four designated emission wavelength of the four photocleavable fluorescent dideoxynucleotides.

SBS was performed on a chip-immobilized DNA template using the photocleavable fluorescent ddNTPs and 3'-modified photocleavable dNTPs combination (ddCTP-PC-Bodipy-FL-510, ddUTP-PC-R6G, ddATP-PC-ROX and ddGTP-PC-Bodipy-650, 3'-O-PC-dATP, 3'-O-PC-dCTP, 3'-O-PC-dGTP and 3'-O-PC-dTTP) and the results are shown in FIG. 5. The structure of the self-priming DNA moiety is shown schematically in FIG. 5A, with the first 8 nucleotide sequences immediately after the priming site. The de novo sequencing reaction on the chip was initiated by extending the self-priming DNA using a solution containing the four 3'-O-PC-dNTPs as well as the four ddNTPs-PC-fluorophore, and 9° N mutant DNA polymerase. In order to negate any lagging fluorescence signal that is caused by previously unextended priming strand, a synchronization step was added to reduce the amount of unextended priming strands after the initial extension reaction. A synchronization reaction mixture consisting of just the four 3'-O-PC-dNTPs (FIG. 3) was used along with the 9° N mutant DNA polymerase to extend any remaining priming strand that has a free 3'-OH group to synchronize the incorporation. This extension method where the combination of 3'-O-PC-dNTPs/ddNTPs-PC-fluorophore are used, will not have a negative impact on the enzymatic incorporation of the next nucleotide analogue, because after cleavage to remove the 3'-OH capping group, the DNA product extended by 3'-O-PC-dNTPs carry no modification groups. Previous designs of cleavable fluorescent reversible terminators left small traces of modification (propargyl amine linker) after the cleavage of the fluorophore on the base of the nucleotide. Successive addition of these reversible terminators into a growing DNA strand during SBS will lead to a newly synthesized DNA strand with, at each base site, a small leftover linker. This may decrease the ability of the enzyme to efficiently incorporate the next incoming nucleotide, which will undoubtedly lead to loss of synchrony and furthermore, maximal readlength. With this combination approach, DNA products extended by ddNTPs-PC-fluorophore, after fluorescence detection and cleavage, are no longer involved in the subsequent polymerase reaction because they are permanent terminators. Therefore, further polymerase reaction only occurs on a DNA strand that incorporates the 3'-O-PC-dNTPs, and subsequently turned back into natural bases, which should have no ill effect on the enzyme. After washing, the extension of the primer by the complementary fluorescent dideoxynucleotide was confirmed by observing an orange signal (the emission from ROX) in a 4-color fluorescent scanner, [FIG. 5. (1)]. After detection of the fluorescent signal, the surface was immersed in dH$_2$O/acetonitrile (50/50, v/v) solution and irradiated at 355 nm for 1 min using a laser to cleave both the fluorophore from the DNA product extended with ddNTPs-PC-fluorophore and 3'-O-PC group from the DNA product extended with 3'-O-PC-dNTPs. The surface was then rinsed with dH$_2$O, and the residual fluorescent signal was detected again to confirm photocleavage, FIG. 5(2). This was followed by another extension reaction using 3'-O-PC-dNTPs/ddNTPs-PC-fluorophore combination mixture to incorporate the next base complementary to the subsequent base on the template. The entire process of incorporation, synchronization, detection and cleavage was performed multiple times using the combination mixture of photocleavable fluorescent dideoxynucleotides and 3'-O-modified photocleavable reversible terminator nucleotides to identify 8 successive bases in the DNA template. The fluorescence image of the chip after each incorporation event is shown in FIG. 5B, while a plot of the fluorescence intensity vs. the progress of sequencing extension (raw 4-color sequencing data) is shown in FIG. 5C. The DNA sequences are unambiguously identified from the 4-color raw fluorescence data without any processing.

Strategy 1: Template "Walking" by Unlabeled Nucleotides

Figure 9:
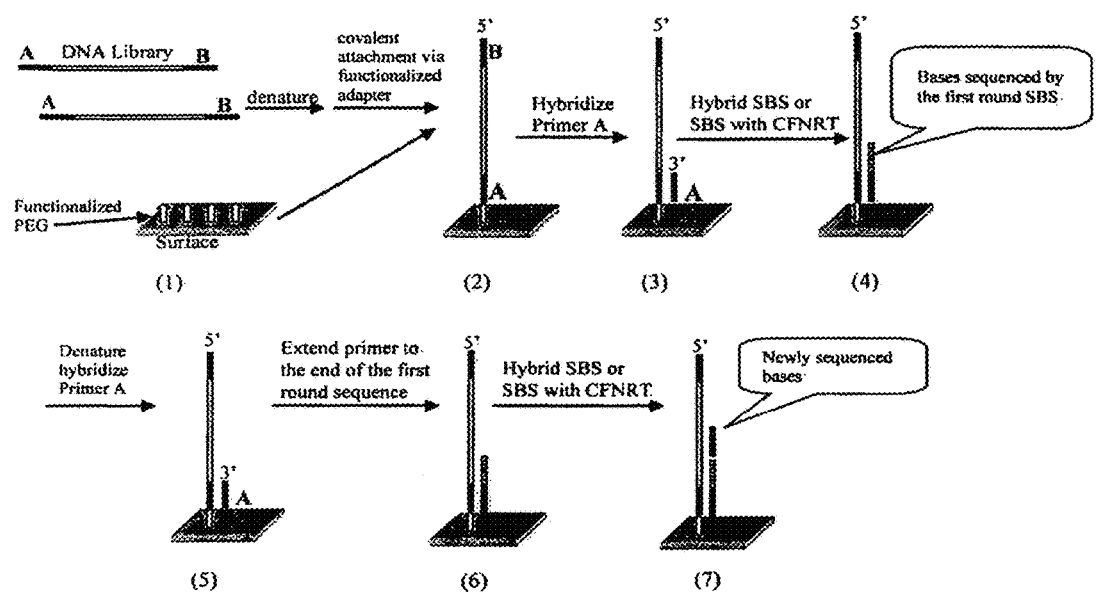
FIG. 9. "Walking" Strategy 1

The fundamental rationale behind this template "walking" strategy is the removal of the sequenced strand and reattaching of the original primer to allow the extension, or walking, of the template with a combination of natural and modified nucleotides to the end of the first round sequence so that SBS can be carried out from that point. Since the original sequenced strand is stripped away, including those terminated with ddNTPs, all the templates become available for "walking". Given that "walking" is carried out with either natural or 3'-modified nucleotides, the subsequent round of SBS is performed on nascent DNA strands for maximum read length. The advantage of template "walking" is its ability to restore all the templates after the denature step, includes those that are terminated with ddNTPs, so the next cycle of SBS can restart with potentially the same amount of nascent DNA as the previous round. The "walking" methodology is applicable to both hybrid SBS and SBS with C—F-NRTs, and has the potential to dramatically increase the read lengths of these SBS technologies (FIG. 9).

Template "Walking" for Hybrid SBS
1. Hybrid SBS (1$^{st}$ Round)

Figure 10:
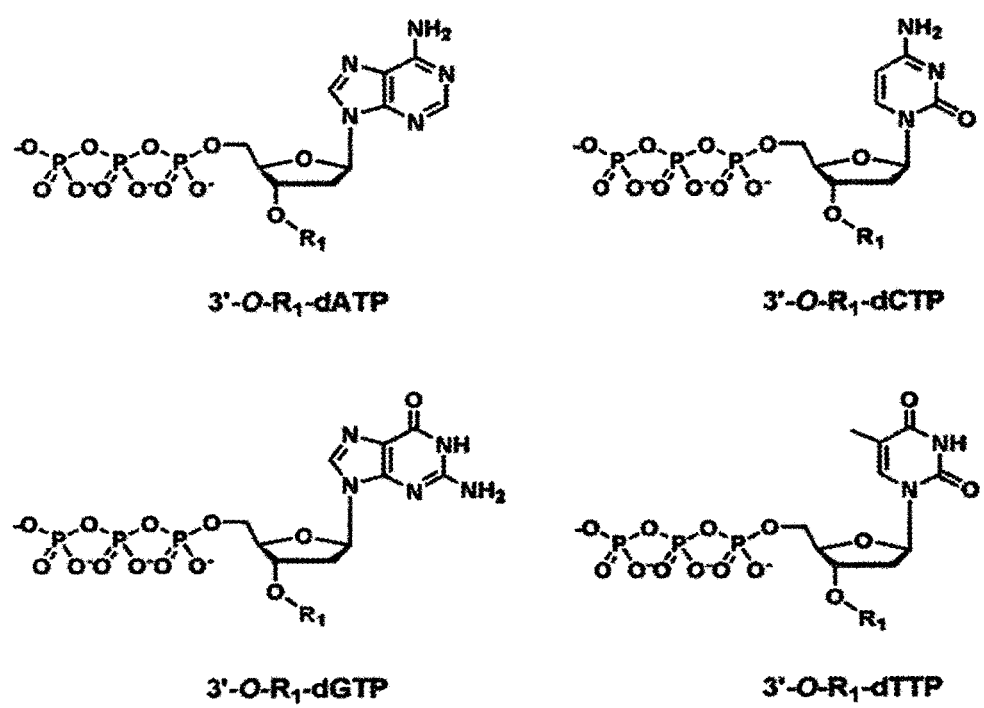
FIG. 10. Structures of the nucleotide reversible terminators
Figure 11:
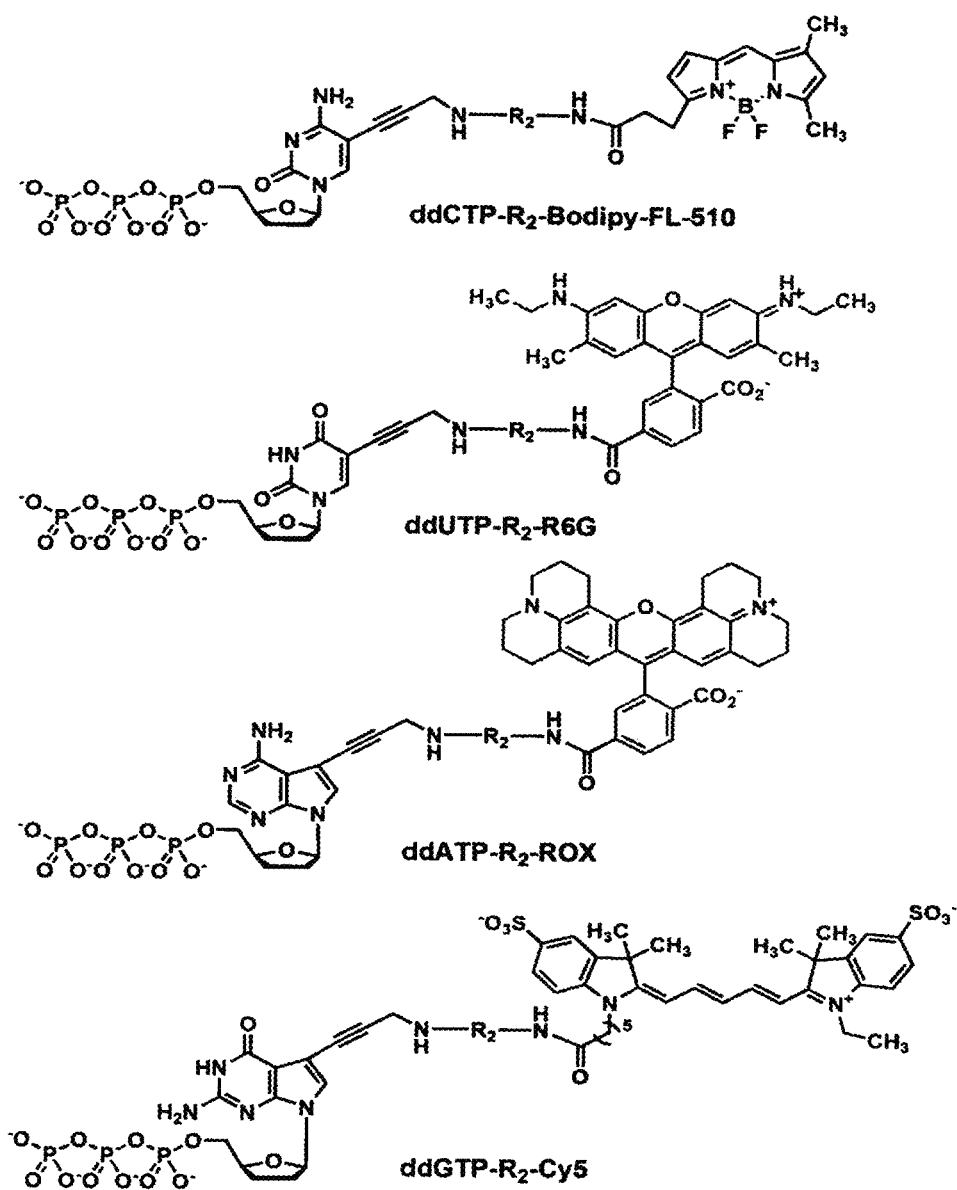
FIG. 11. Structures of cleavable fluorescent dideoxynucleotide terminators
Figure 12:
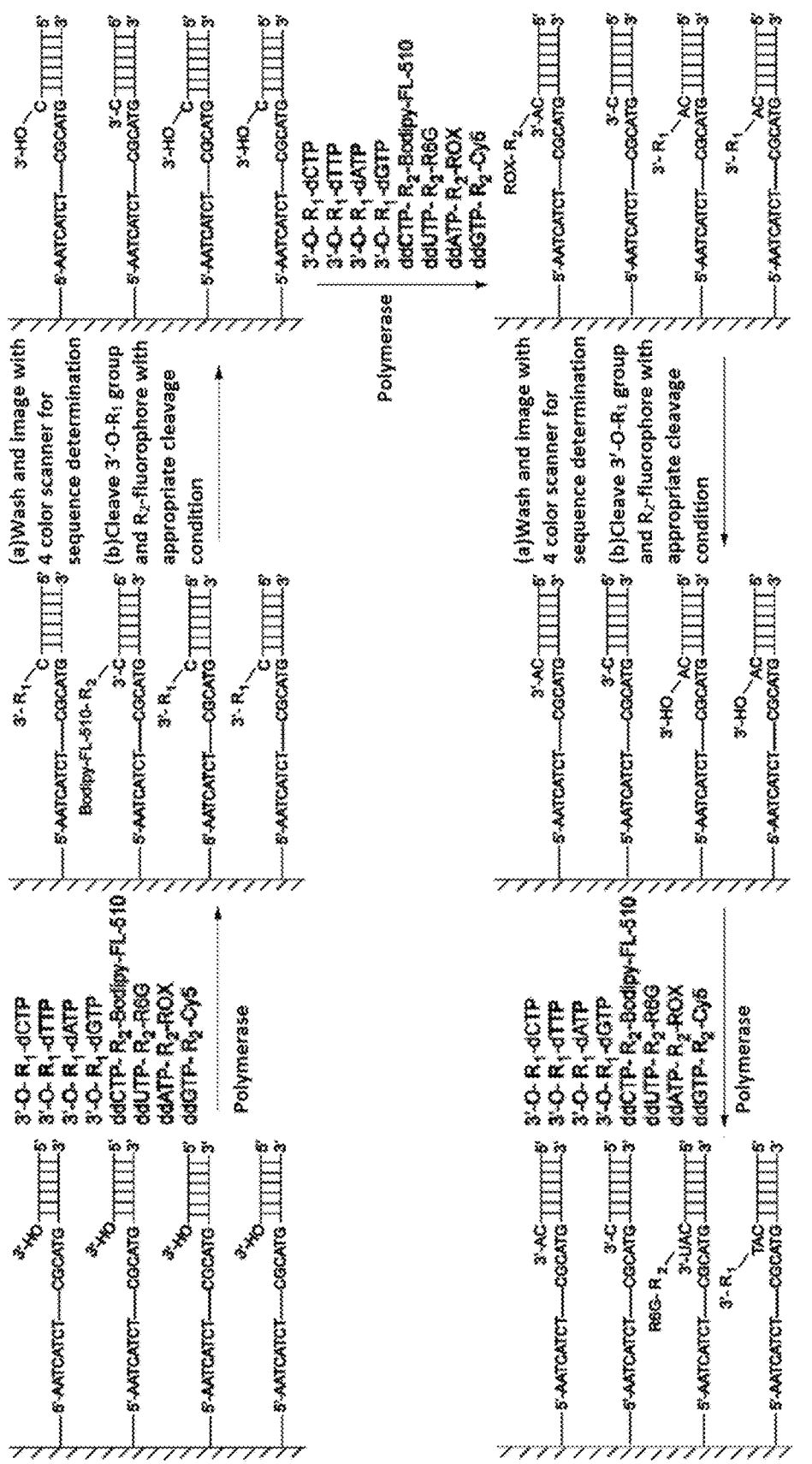
FIG. 12. Hybrid SBS scheme

DNA sequencing by synthesis (SBS) on a solid surface during polymerase reaction offers a paradigm to efficiently decipher multiple DNA sequences in parallel. Hybrid SBS is a hybrid DNA sequencing method between the Sanger dideoxy chain terminating reaction and SBS. In this approach, four nucleotides (FIG. 10) modified as reversible terminators by capping the 3'-OH with a small reversible moiety so that they are still recognized by DNA polymerase as substrates to extend the DNA chain, are used in combination with a small percentage of four cleavable fluorescent dideoxynucleotides (FIG. 11) to perform SBS. Sequences are determined by the unique fluorescence emission of each fluorophore on the DNA products terminated by ddNTPs, while the role of the 3'-O-modified dNTPs is to further extend the DNA strand to continue the determination of the DNA sequence. Upon removing the 3'-OH capping group from the DNA products generated by incorporating the 3'-O-modified dNTPs and the fluorophore from the DNA products terminated with the ddNTPs, the polymerase reaction reinitiates to continue the sequence determination (FIG. 12). Such incorporation, fluorescence measurement and dye removal is repeatedly conducted until the detectable fluorescence intensity is not distinguishable, indicating a situation in which all the elongated primers are terminated with ddNTP. To overcome this "halted sequencing" due to ddNTP termination, a "walking" step is carried out to reset the templates.

2. Template "Walking"

Immediately after the first round of SBS, all of the elongated primers ended terminated with ddNTPs are removed from the template by denaturing. The templates are freed again and available for further sequencing reactions. To achieve template "walking", the same starting primer is annealed to the template again and enzymatic incorporation is conducted to fill the gap between first and second stages of SBS. Five strategies are available for the walking process. Each approach has its advantages and shortcomings, which are summarized in the following.

Figure 13:
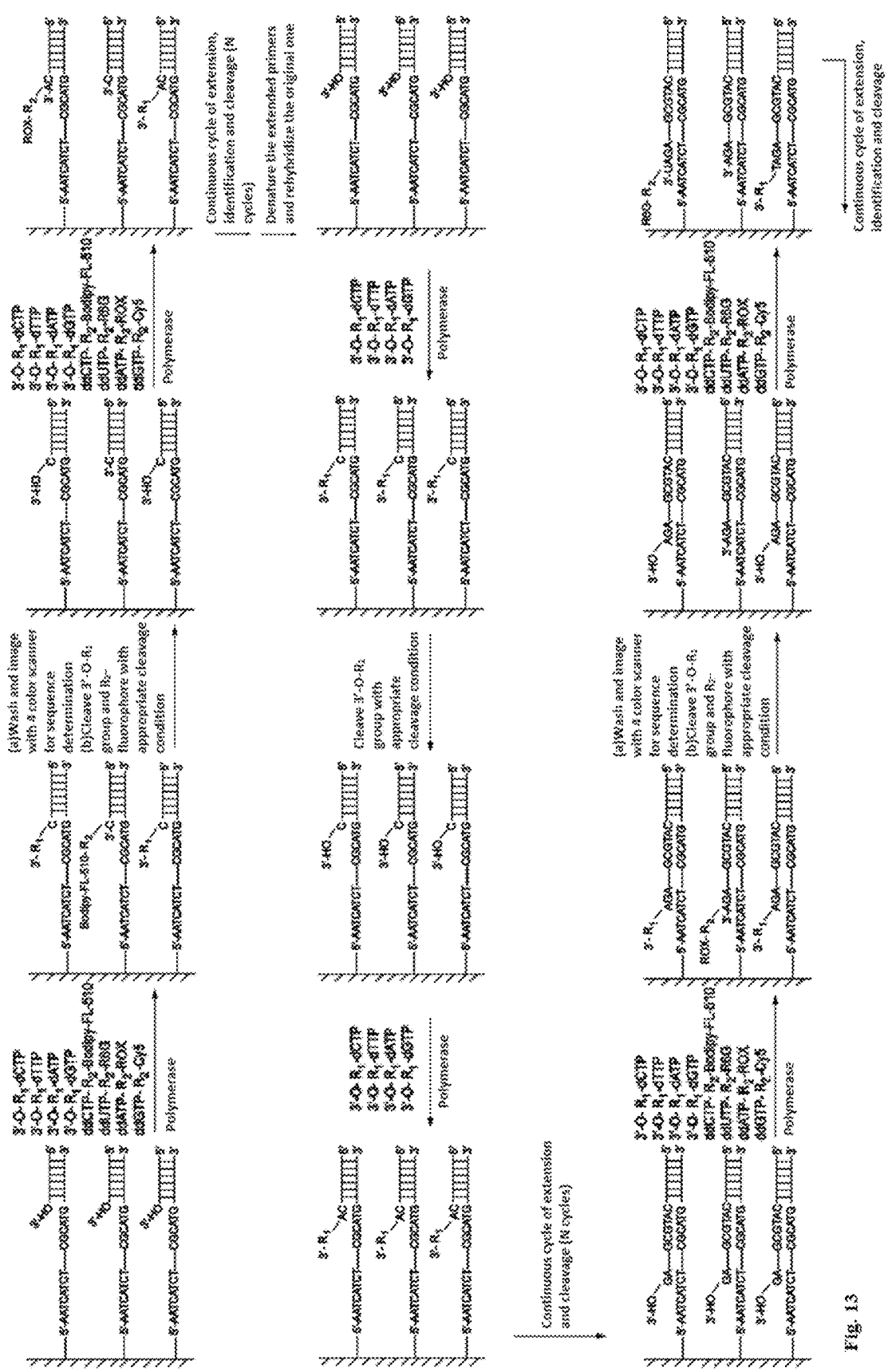
FIG. 13. Template "Walking" Method 1

Method 1. Nucleotide reversible terminators (3'-O—R$_1$-dNTPs) are used as substrates to perform enzymatic incorporation (FIG. 13). After incorporation, specific chemical reaction is applied to regenerate 3'-OH to ensure the subsequent incorporation. The number of repeated cycles of such incorporation and cleavage will exactly match the actual read length in the first stage of SBS, so that this "filling gap" incorporation stops at the same point where the longest ddNTP primer reaches.

Figure 14:
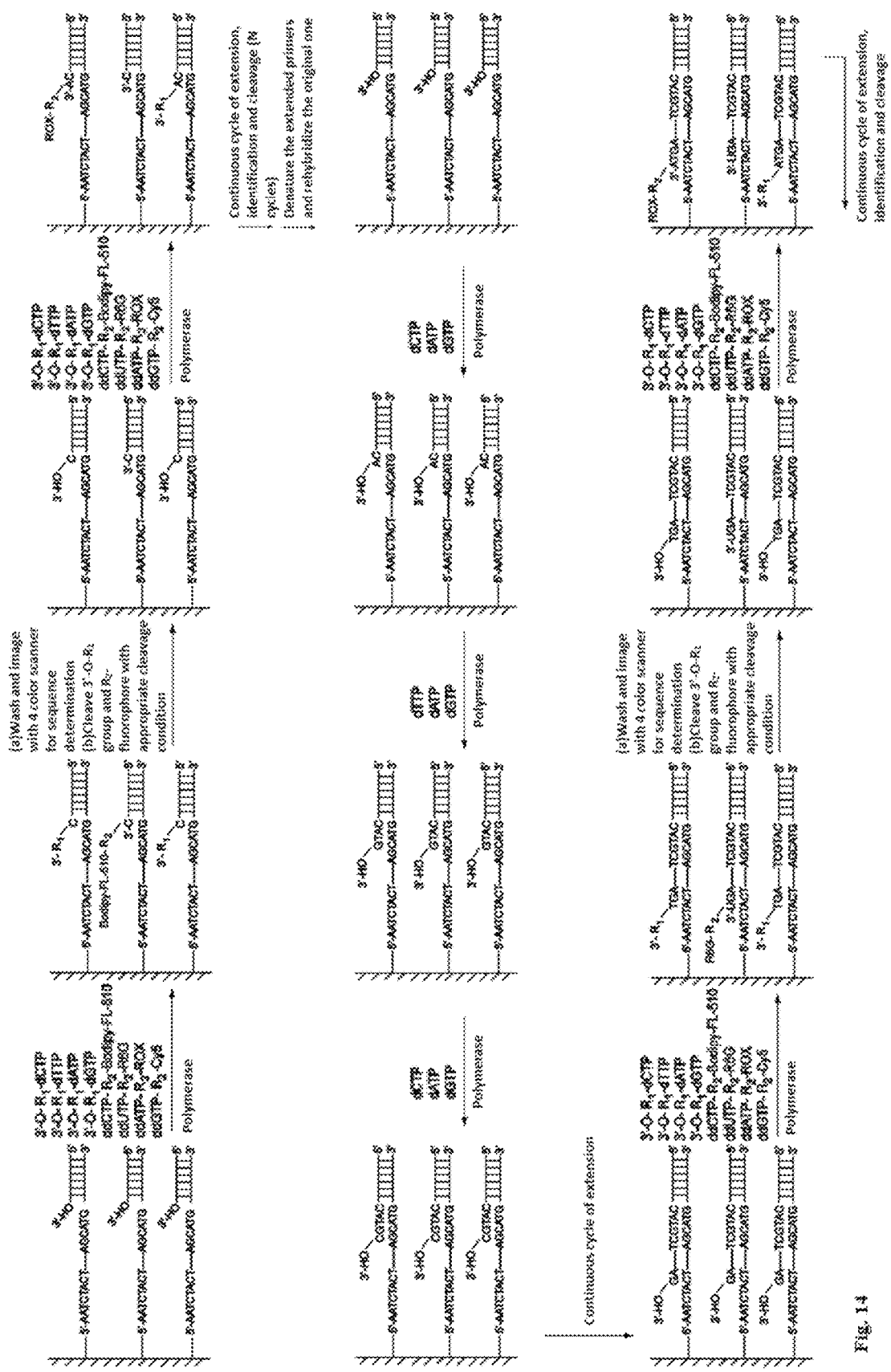
FIG. 14. Template "Walking" Method 2

Methods 2, 3, and 4. Enzymatic incorporation is conducted using two sets of nucleotides as substrates (FIG. 14). For example, the first set of nucleotides composed of dCTP, dATP, and dGTP (sans dTTP) was used to perform incorporation, so that the polymerase reaction stops once it reaches a base "A" in template. Then enzymatic incorporation is resumed with the second set of nucleotides composed of dTTP, dATP, and dGTP (sans dCTP), resulting in a polymerase reaction that stops at the base "G" in template. The repeated cycles of such incorporations fill the gap between first and second stages of SBS.

Figure 15:
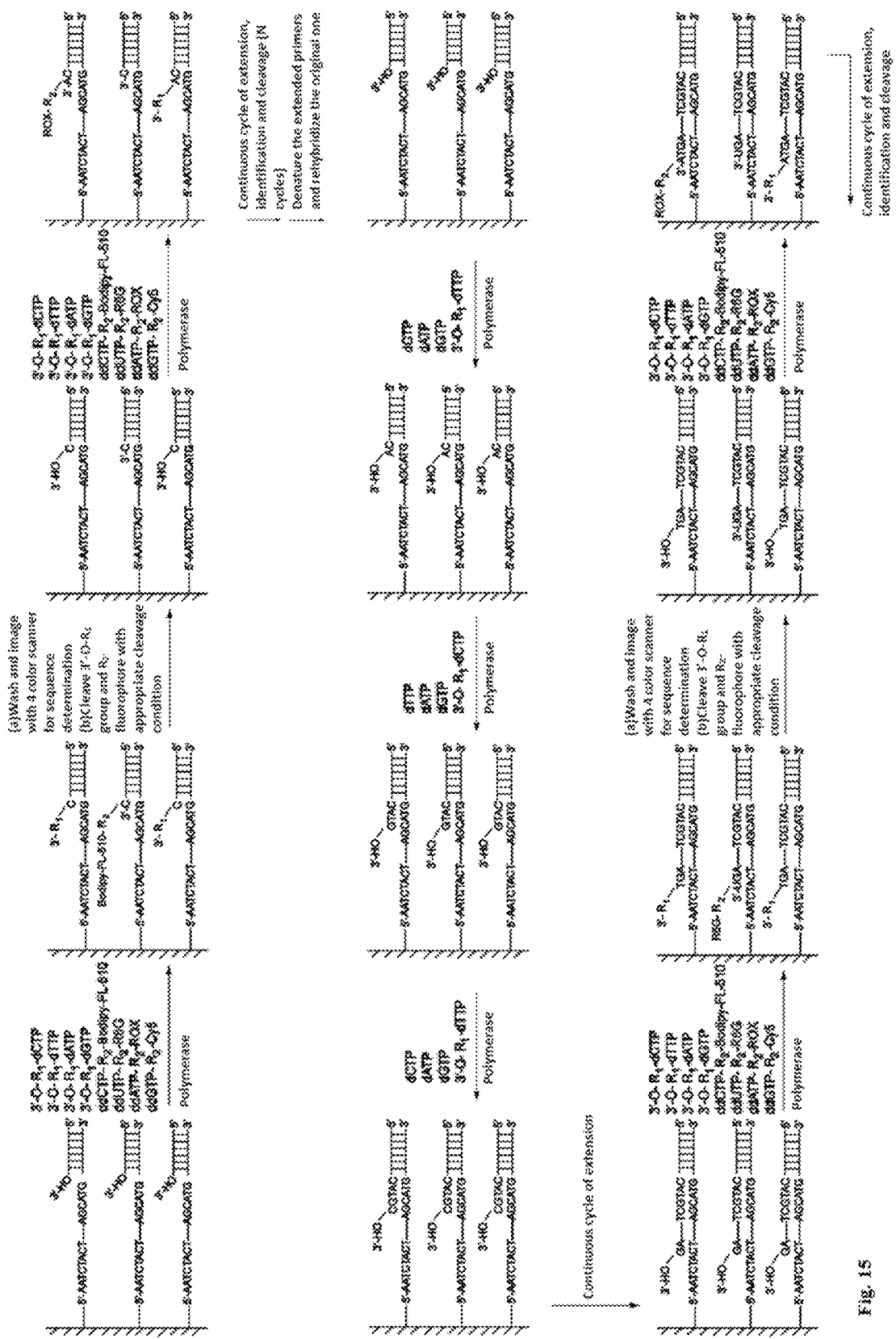
FIG. 15. Template "Walking" Method 3

To minimize the mis-incorporation rate, another enzyme substrate which can be recognized but not incorporated by the polymerase is assigned to each set of nucleotides. For instance, if the DNA polymerase used can only incorporate dNTP but not 3' blocked nucleotides, 3'-O—R$_1$-dTTP will be combined with dCTP, dATP and dGTP as the first set, while 3'-O—R$_1$-dCTP will be combined with dTTP, dATP and dGTP as the second set to elongate the primer (FIG. 15).

Figure 16:
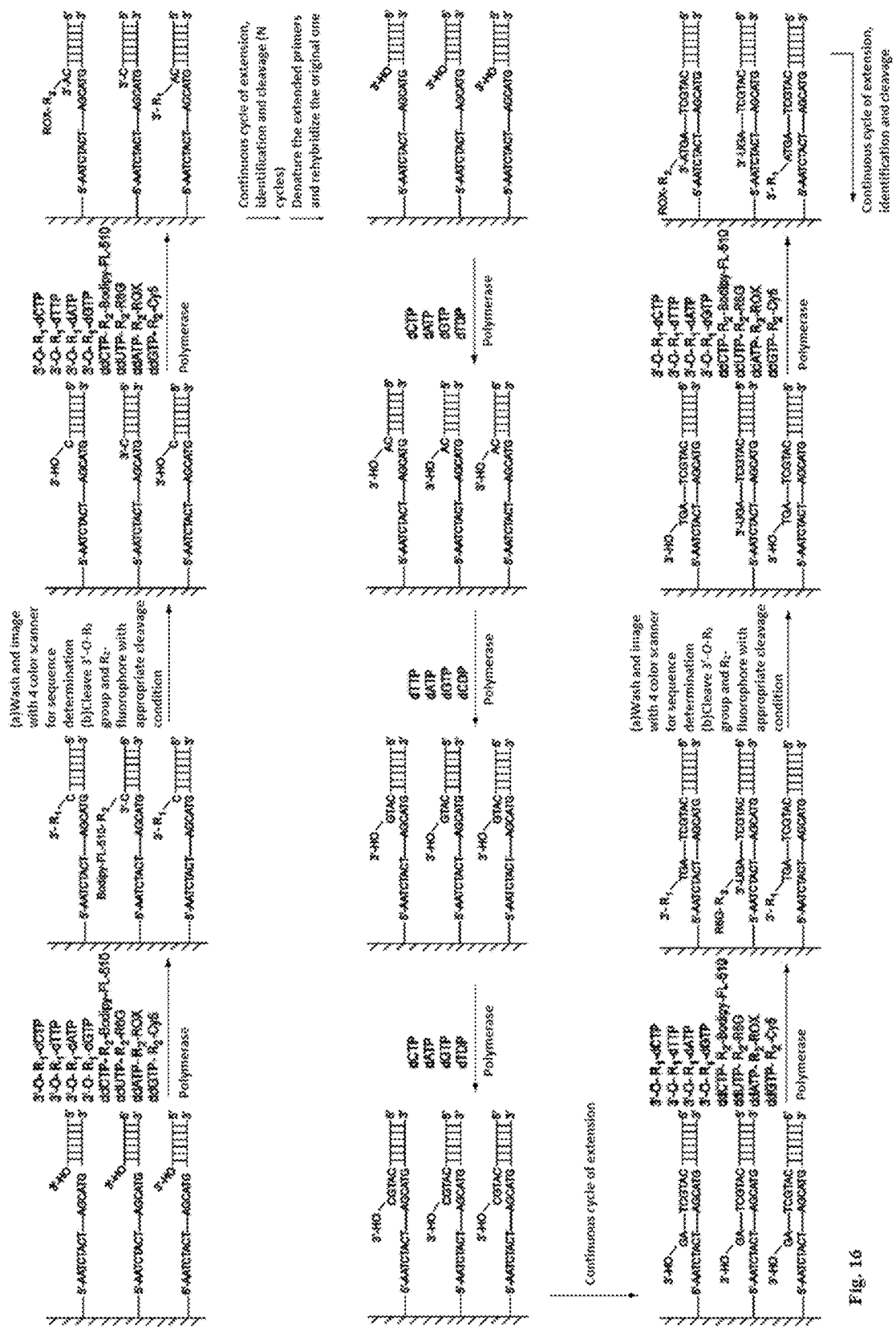
FIG. 16. Template "Walking" Method 4

Alternatively, deoxyribonucleotides diphosphate can also play such role, replacing the 3'-O—R$_1$-dNTPs, during enzymatic incorporation (FIG. 16).

Figure 17:
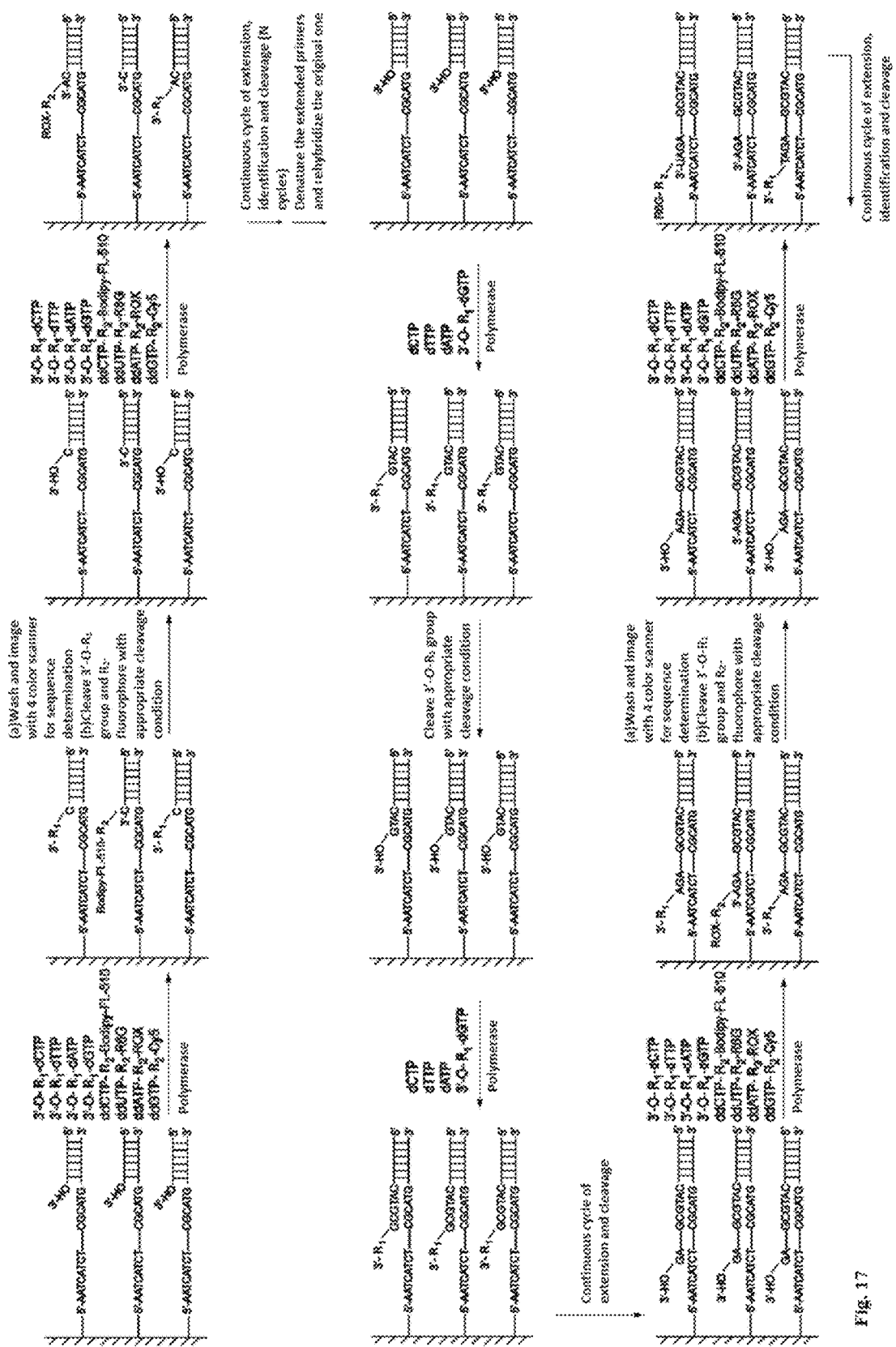
FIG. 17. Template "Walking" Method 5

Method 5. Enzymatic incorporation is conducted using three dNTPs and another nucleotide reversible terminator as substrates (FIG. 17). Primer elongation will only be stopped once it incorporates nucleotide reversible terminator. After incorporation, specific chemical reaction is applied to regenerate 3'-OH which ensure consecutive incorporation of the next round. Repeated cycles of such incorporation and cleavage will fill the gap between first and second stages of SBS.

3. Re-Initiation of Hybrid SBS

Once the "walking" process is completed, the second stage of SBS is conducted using mixture of nucleotide reversible terminators and fluorescently labeled dideoxynucleotides as incorporation substrates same as described above. Another cluster of bases on the template can be continuously revealed, leading to the doubling of the original read length. The SBS-walking-SBS process is repeated to generate maximum read length.

EXAMPLES

Figure 18:
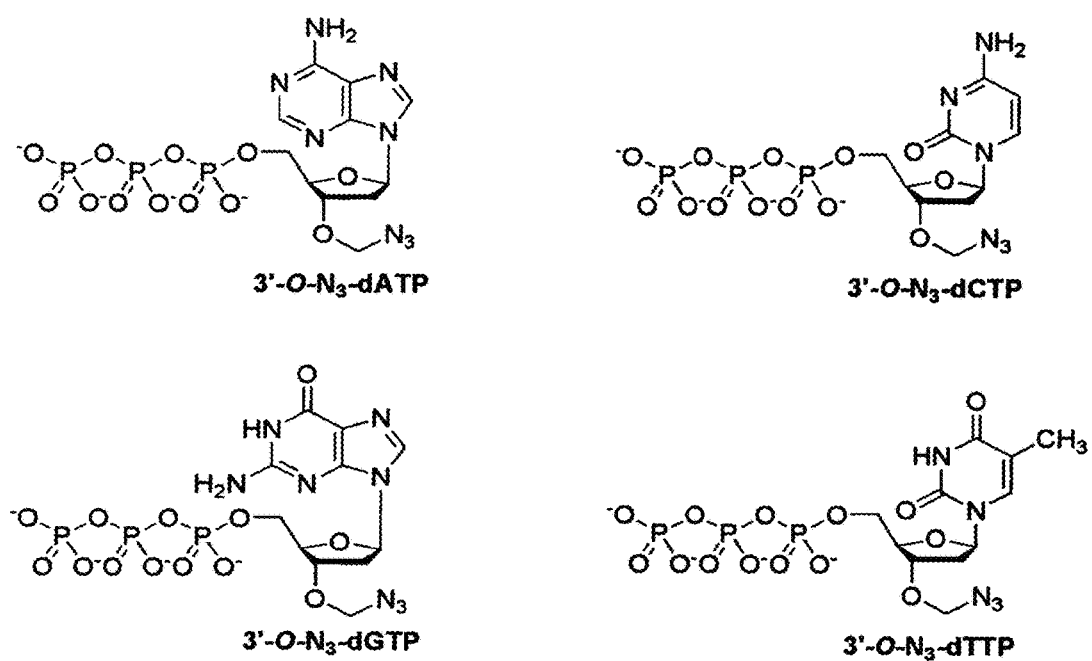
FIG. 18. Structures of the nucleotide reversible terminators, 3'-O—N$_3$-dATP, 3'-O—N$_3$-dCTP, 3'-O—N$_3$-dGTP, 3'-O—N$_3$-dTTP FIG. 19. Structures of cleavable fluorescent dideoxynucleotide terminators ddNTP-N$_3$-fluorophores, with the 4 fluorophores having distinct fluorescent emissions: ddCTP-N$_3$-Bodipy-FL-510 ($\lambda_{abs\,(max)}$=502 nm; $\lambda_{em\,(max)}$=510 nm), ddUTP-N$_3$-R6G ($\lambda_{abs\,(max)}$=525 nm; $\lambda_{em\,(max)}$=550 nm), ddATP-N$_3$-ROX ($\lambda_{abs\,(max)}$=585 nm; $\lambda_{em\,(max)}$=602 nm), and ddGTP-N$_3$-Cy5 ($\lambda_{abs\,(max)}$=649 nm; $\lambda_{em\,(max)}$=670 nm).
Figure 20:
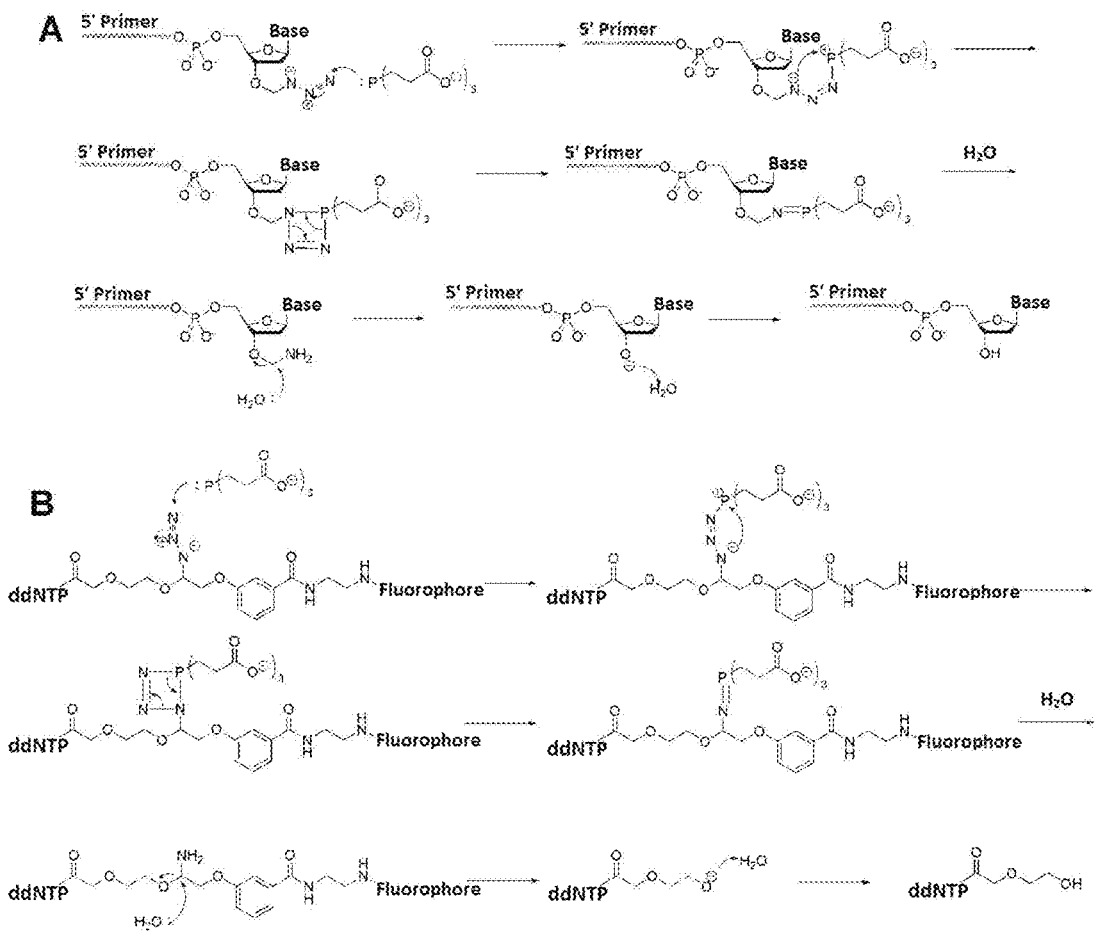
FIG. 20. (A) Staudinger reaction with TCEP to regenerate the 3'-OH group of the DNA extension product. (B) Staudinger reaction with TCEP to cleave the N$_3$-fluorophore from the dideoxynucleotide.

1. Design and Synthesis of 3'-O-Modified NRTs and Cleavable Fluorescent Dideoxynucleotide Terminators for the Hybrid SBS Four 3'-O-azidomethyl-modified NRTs (3'-O—N$_3$-dNTPs) were synthesized and evaluated (FIG. 18) for use in the hybrid SBS approach. The 3'-O-modified NRTs containing an azidomethyl group to cap the 3'-OH on the sugar ring were synthesized based on similar method to that reported by Zavgorodny et al. The 3'-O-azidomethyl group on the DNA extension product generated by incorporating each of the NRTs is efficiently removed by the Staudinger reaction using aqueous Tris(2-carboxy-ethyl)phosphine (TCEP) solution followed by hydrolysis to yield a free 3'-OH group for elongating the DNA chain in subsequent cycles of the hybrid SBS (FIG. 20A).

Figure 19:
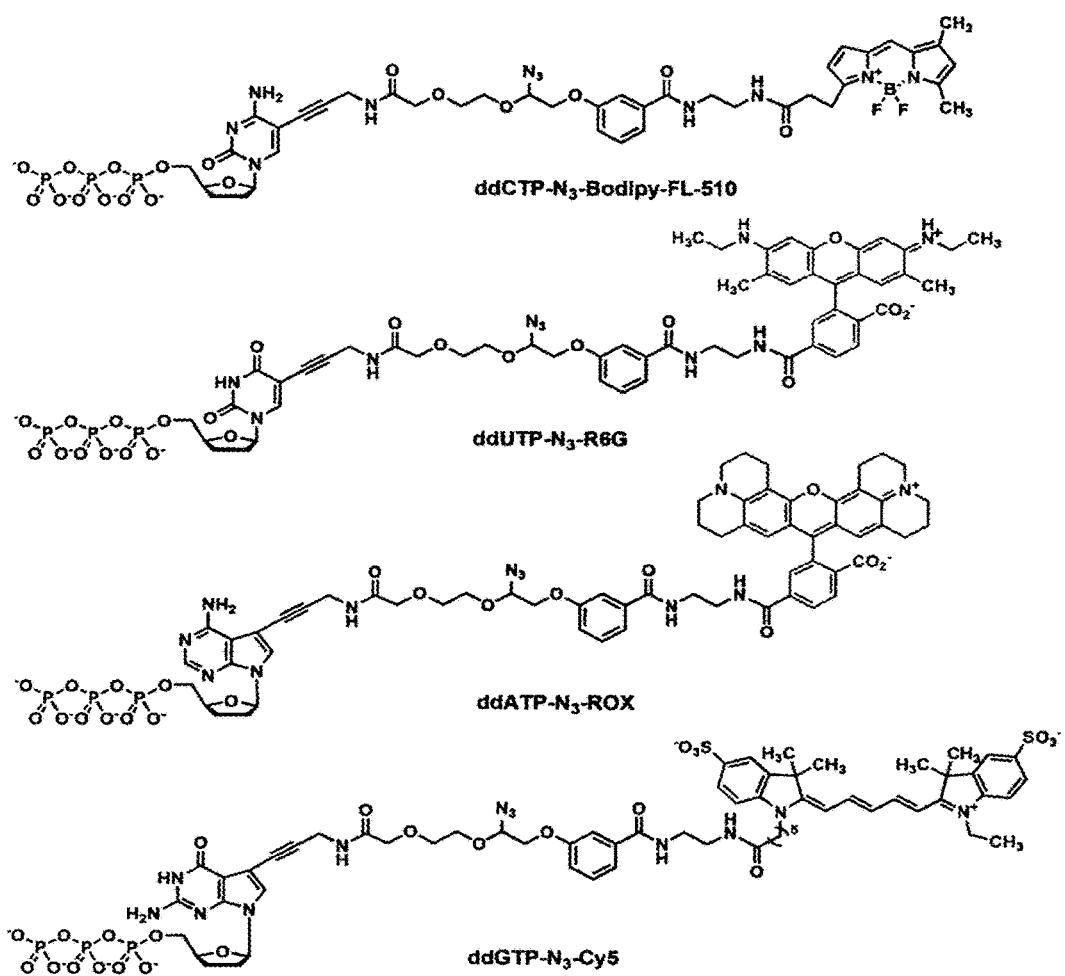

To demonstrate the feasibility of carrying out the hybrid SBS on a DNA chip, four cleavable fluorescent dideoxynucleotide terminators were designed and synthesized, ddNTP-N$_3$-Fluorophores (ddCTP-N$_3$-Bodipy-FL-510, ddUTP-N$_3$-R6G, ddATP-N$_3$-ROX and ddGTP-N$_3$-Cy5) (FIG. 19). The ddNTP-N$_3$-Fluorophore were used in combination with the four NRTs (FIG. 18) to perform the hybrid SBS. Modified DNA polymerases have been shown to be highly tolerant to nucleotide modifications with bulky groups at the 5-position of pyrimidines (C and U) and the 7-position of purines (A and G). Thus, a each unique fluorophore was attached to the 5 position of C/U and the 7 position of A/G through a cleavable linker. The cleavable linker is also based on an azido modified moiety as a trigger for cleavage, a mechanism that is similar to the removal of the 3'-O-azidomethyl group (FIG. 20B).

2. Four-Color DNA Sequencing on a Chip by the Hybrid SBS Approach

Figure 21:
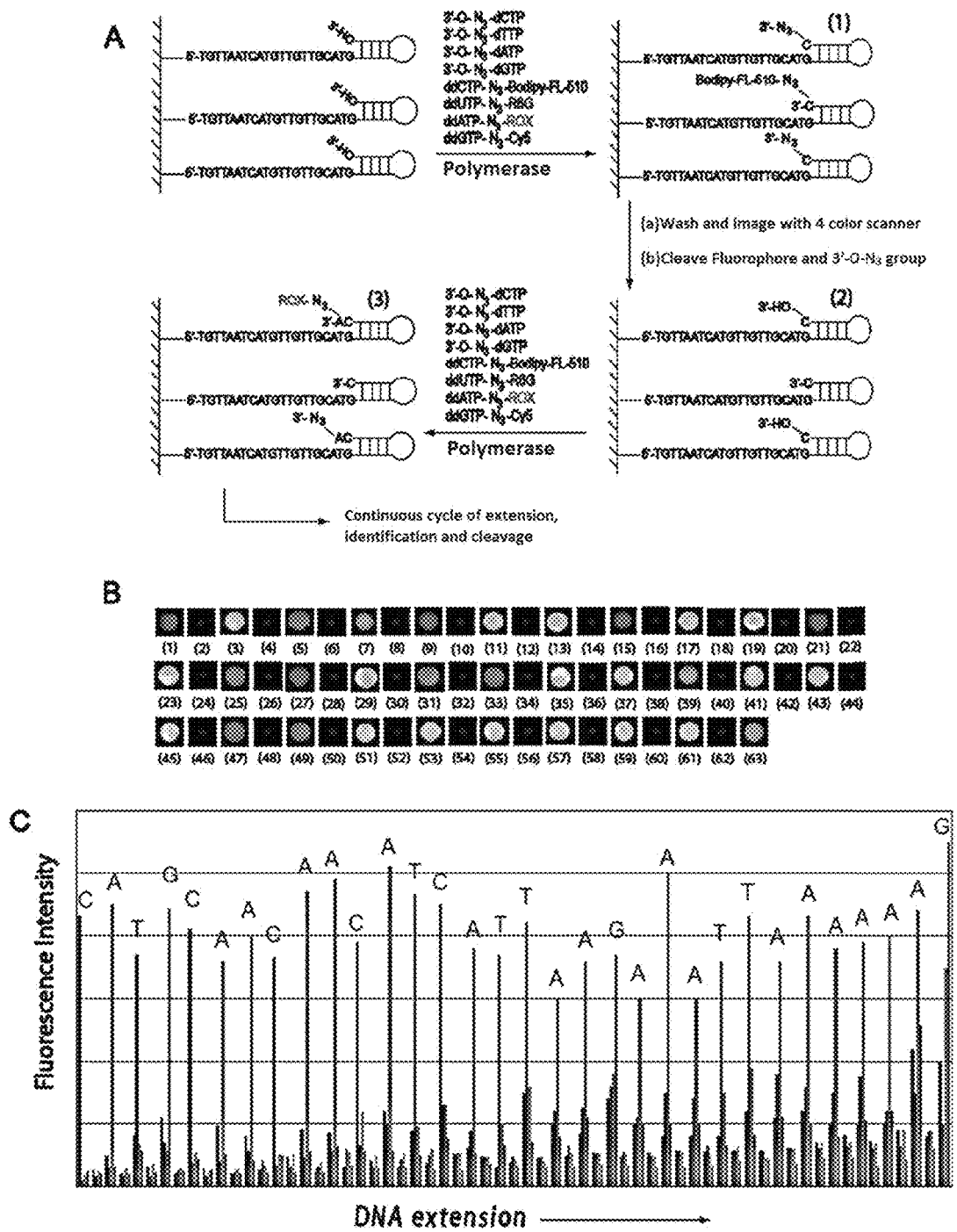
FIG. 21. Four-color DNA sequencing by the hybrid SBS approach

Hybrid SBS was performed on a chip-immobilized DNA template using the 3'-O—N$_3$-dNTP/ddNTP-N$_3$-fluorophore combination and the results are shown in FIG. 21. The general four-color sequencing reaction scheme on a chip is shown in FIG. 21A. The de novo sequencing reaction on the chip was initiated by extending the self-priming DNA using a solution containing the combination of the four 3'-O—N$_3$-dNTPs and the four ddNTP-N$_3$-fluorophores, and 9° N DNA polymerase.

The four-color images from a fluorescence scanner for each step of the hybrid SBS on a chip is shown in FIG. 21B. The entire process of incorporation, synchronization, detection and cleavage was performed multiple times to identify 32 successive bases in the DNA template. The plot of the fluorescence intensity vs. the progress of sequencing extension (raw 4-color sequencing data) is shown in FIG. 21C. The DNA sequences were unambiguously identified with no errors from the 4-color raw fluorescence data without any processing.

3. Primer Reset and 2nd Round SBS

Figure 22:
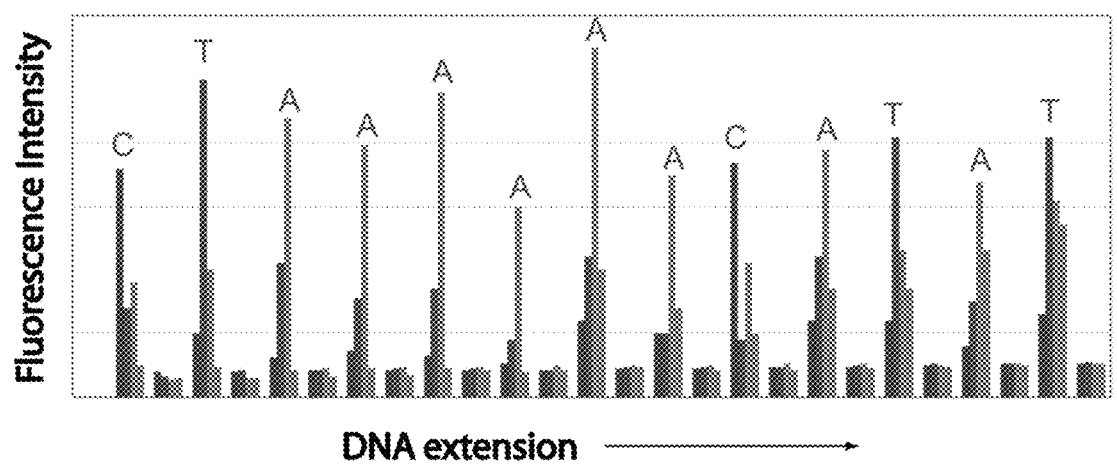
FIG. 22. Four-color DNA sequencing by the hybrid SBS after template "walking"

To demonstrate the concept of walking, the same self-priming DNA was immobilized on surface as template. After identifying the first 32 bases unambiguously with no errors by the first round hybrid SBS, the primer was reset for the second round SBS by elongating the original primer over the sequenced region via enzymatic incorporations. A solution containing dATP, dTTP, dCTP and 3'-O—N$_3$-dGTP was used to perform the polymerase reaction. 9° N DNA polymerase incorporates 3' unblocked nucleotides more efficiently, leading to certain percentage of primers not fully extended by 3'-O—N$_3$-dGTP. To minimize this effect, a synchronization step was added to reduce the amount of out-of-phase primers after the initial extension reaction. A synchronization reaction mixture consisting of just 3'-O—N$_3$-dGTP in relative high concentration was used along with the 9° N DNA polymerase. The 3'-O-azidomethyl group on the DNA extension product generated by incorporating 3'-O—N$_3$-dGTP was efficiently removed by using aqueous Tris(2-carboxy-ethyl)phosphine (TCEP) solution to yield a free 3'-OH group for elongating the DNA chain in subsequent cycles of enzymatic incorporation. The entire process of incorporation, synchronization and cleavage were conducted repeatedly until the sequenced bases during the first round SBS were "walked" over. After the primer was reset by the enzymatic incorporation, the second stage of SBS was conducted using mixture of nucleotide reversible terminators and fluorescently labeled dideoxynucleotides as incorporation substrates same as described above. Another 13 bases were successfully identified after template "walking" (FIG. 22).

Template "Walking" for SBS with CFNRTs
1. SBS with C—F-NRTs

Figure 23:
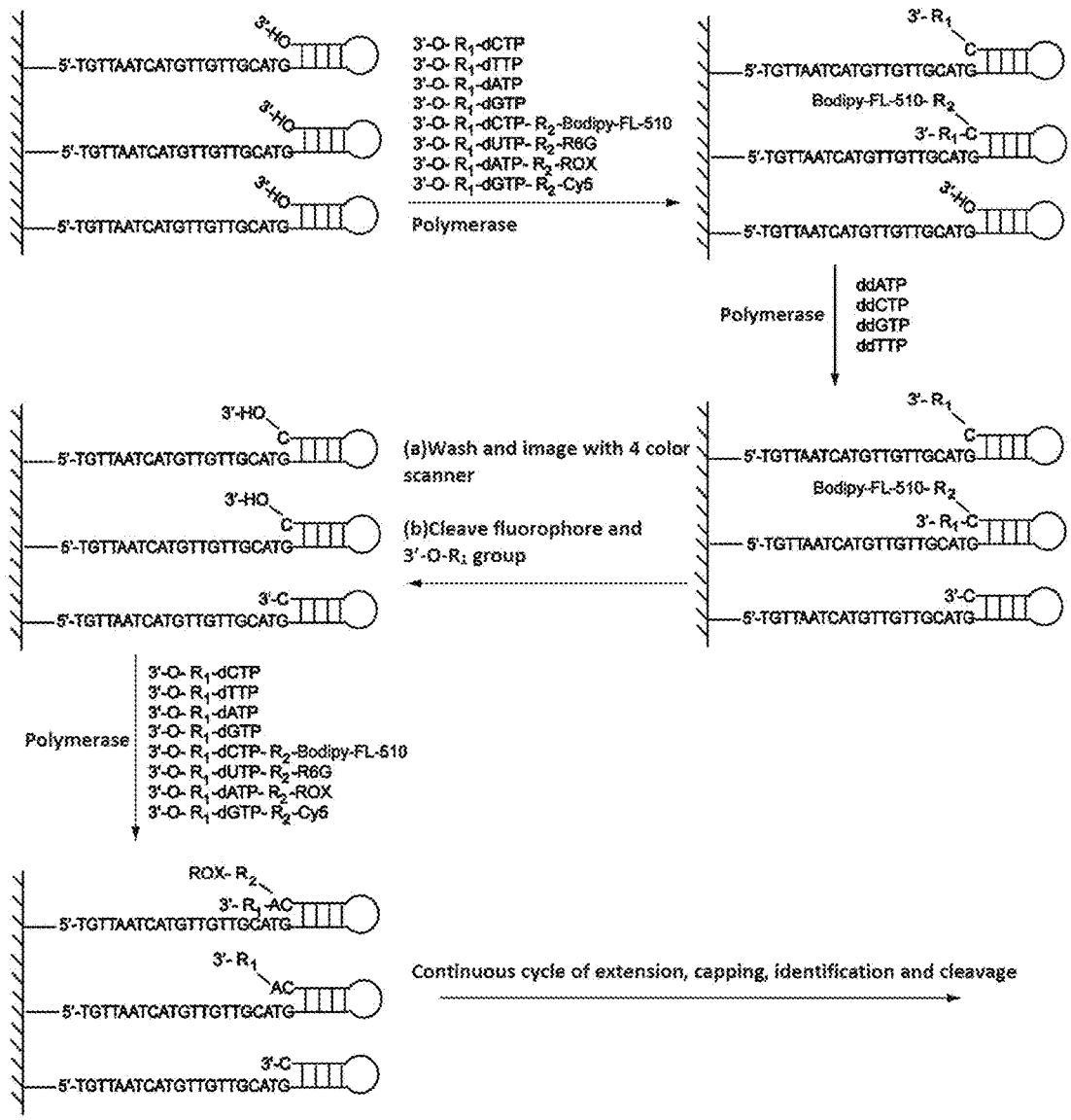
FIG. 23. General Scheme for SBS with C—F-NRTs

DNA sequencing by synthesis (SBS) on a solid surface during polymerase reaction offers a paradigm to efficiently decipher multiple DNA sequences in parallel. Disclosed is the development of a DNA sequencing method that involves the extension of target DNA strand with modified cleavable fluorescent nucleotide reversible terminators (C—F-NRTs, 3'-O—R$_1$-dNTPs-R$_2$-fluorophore) in combination with cleavable nucleotide reversible terminators (C-NRTs, 3'-O—R$_1$-dNTPs). A set of four C—F-NRTs is produced via dual modifications by capping the 3'-OH group with a small chemical moiety and tethering a fluorophore through a cleavable linker to either the 7-position of the purines (A, G) or the 5-position of the pyrimidines (C, T) so that they are still recognized as substrates by DNA polymerase. Another set of four C-NRTs is modified similarly as the C—F-NRTs except no fluorophore is attached, which results in a reduction of the size of C-NRTs and the increment of DNA polymerase incorporation efficiency. In this approach, an extension mixture composed of the C-NRTs with a small percentage of the C—F-NRTs is used to perform SBS. Sequences are determined by the unique fluorescence emission of each fluorophore on the DNA products terminated by the C—F-NRTs. Immediately following the detection step, a synchronization reaction is performed using only the C-NRTs to extend the un-extended DNA strands. A dideoxynucleotides (ddNTPs) capping step is carried out afterwards to completely rid of the remaining un-extended DNA. Upon removing the 3'-OH capping group from the DNA products generated by incorporating both C—F-NRTs and C-NRTs and the fluorophore from the C—F-NRTs, the polymerase reaction reinitiates to continue the sequence determination. The following scheme (FIG. 23) illustrates the general process for SBS with C—F-NRTs.

Figure 24:
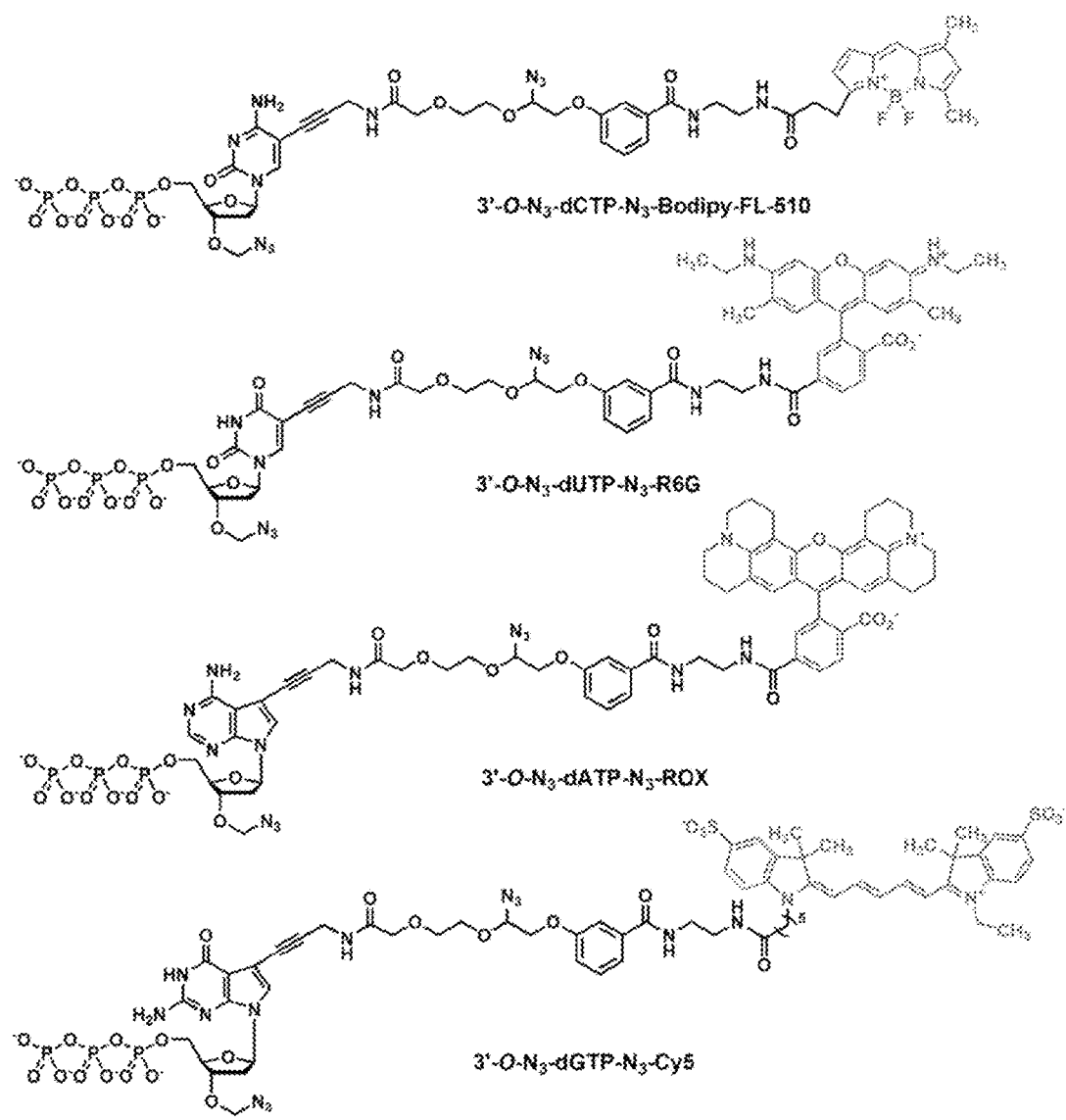
FIG. 24. Structure of 3'-O—N$_3$-dNTPs-N$_3$-fluorophore
Figure 25:
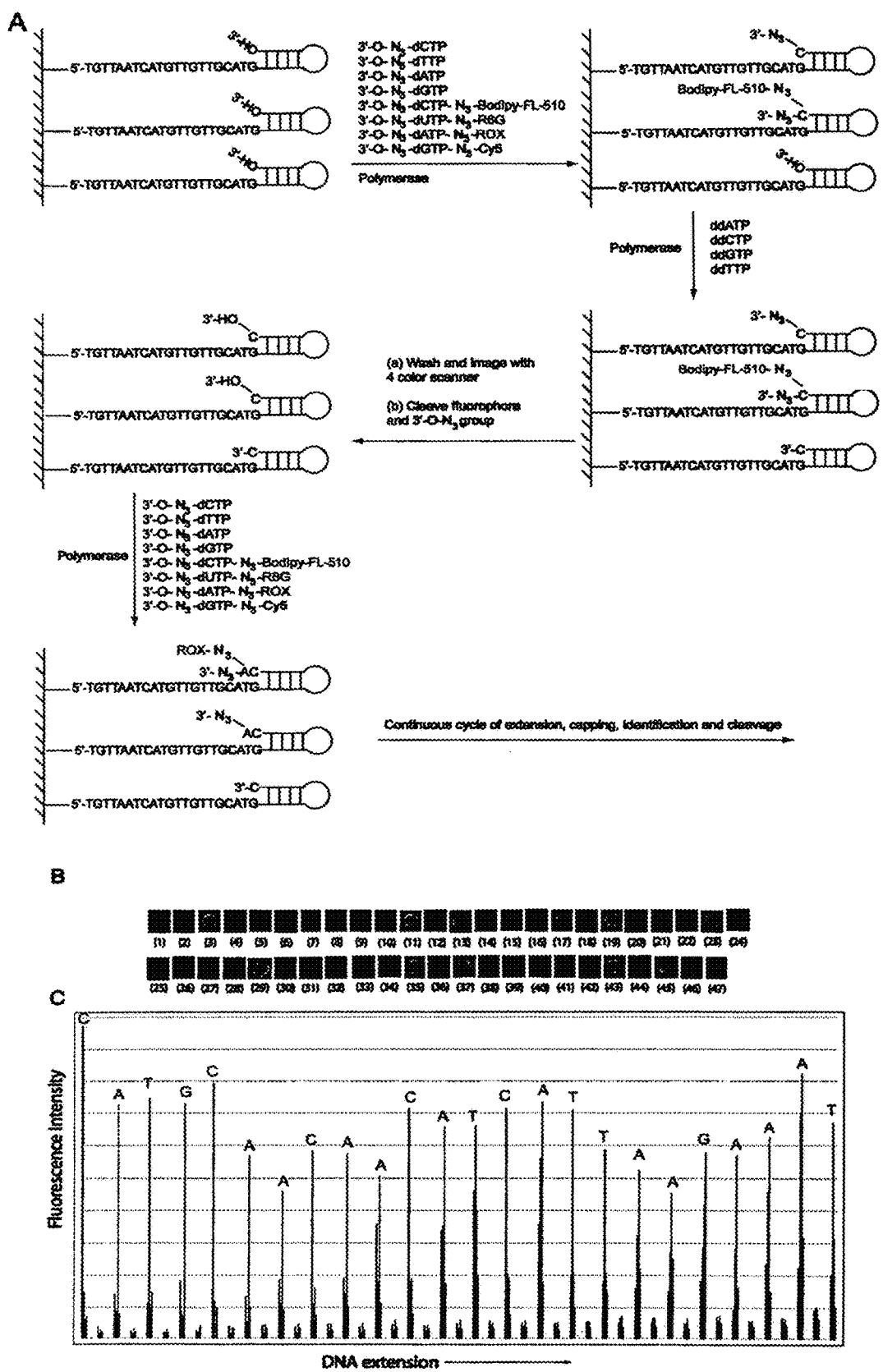
FIG. 25. Four-color DNA SBS with 3'-O—N$_3$-dNTPs-N$_3$-fluorophore. (A) A SBS with C—F-NRTs scheme for four-color sequencing on a chip by using four 3'-O—N$_3$-dNTPs-N$_3$-fluorophore and 3'-O—N$_3$-dNTPs with ddNTPs capping. (B) Four-color fluorescence images for each step of the SBS: (1) incorporation of 3'-O—N$_3$-dCTP-N$_3$-Bodipy-Fl-510 and 3'-O—N$_3$-dCTP; (2) cleavage of N$_3$-Bodipy-Fl-510 and 3'-CH$_2$N$_3$ group; (3) incorporation of 3'-O—N$_3$-dATP-N$_3$-Rox and 3'-O—N$_3$-dATP; (4) cleavage of N$_3$-Rox and 3'-CH$_2$N$_3$ group; images 5-47 were produced similarly. (C) A plot (four-color sequencing data) of raw fluorescence emission intensity obtained by using 3'-O—N$_3$-dNTPs-N$_3$-fluorophore and 3'-O—N$_3$-dNTPs. The small groups of peaks between the identified bases are fluorescent background from the DNA chip.
Figure 26:
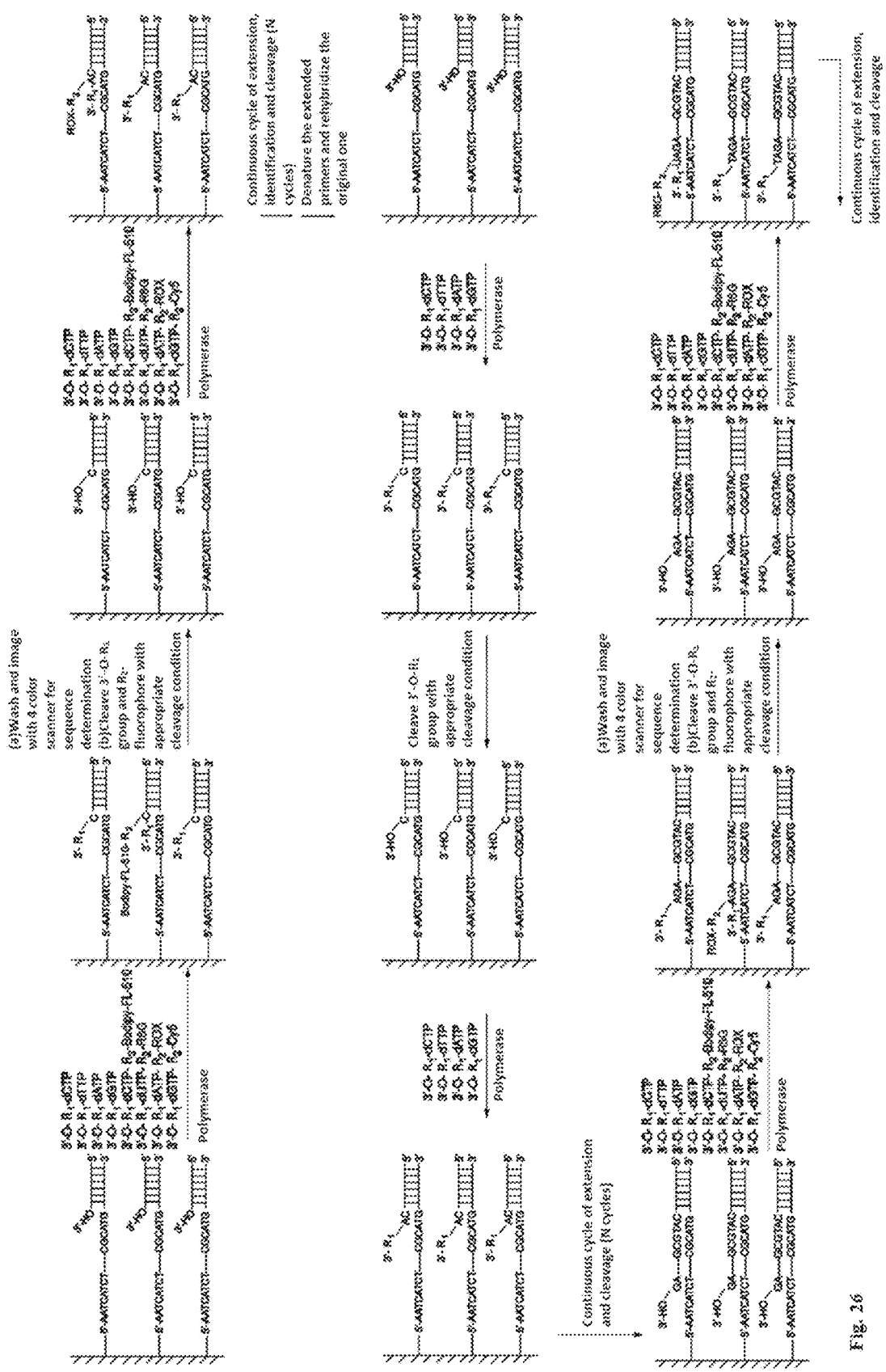
FIG. 26. Template "Walking" Method 1 for SBS with C—F-NRTs
Figure 27:
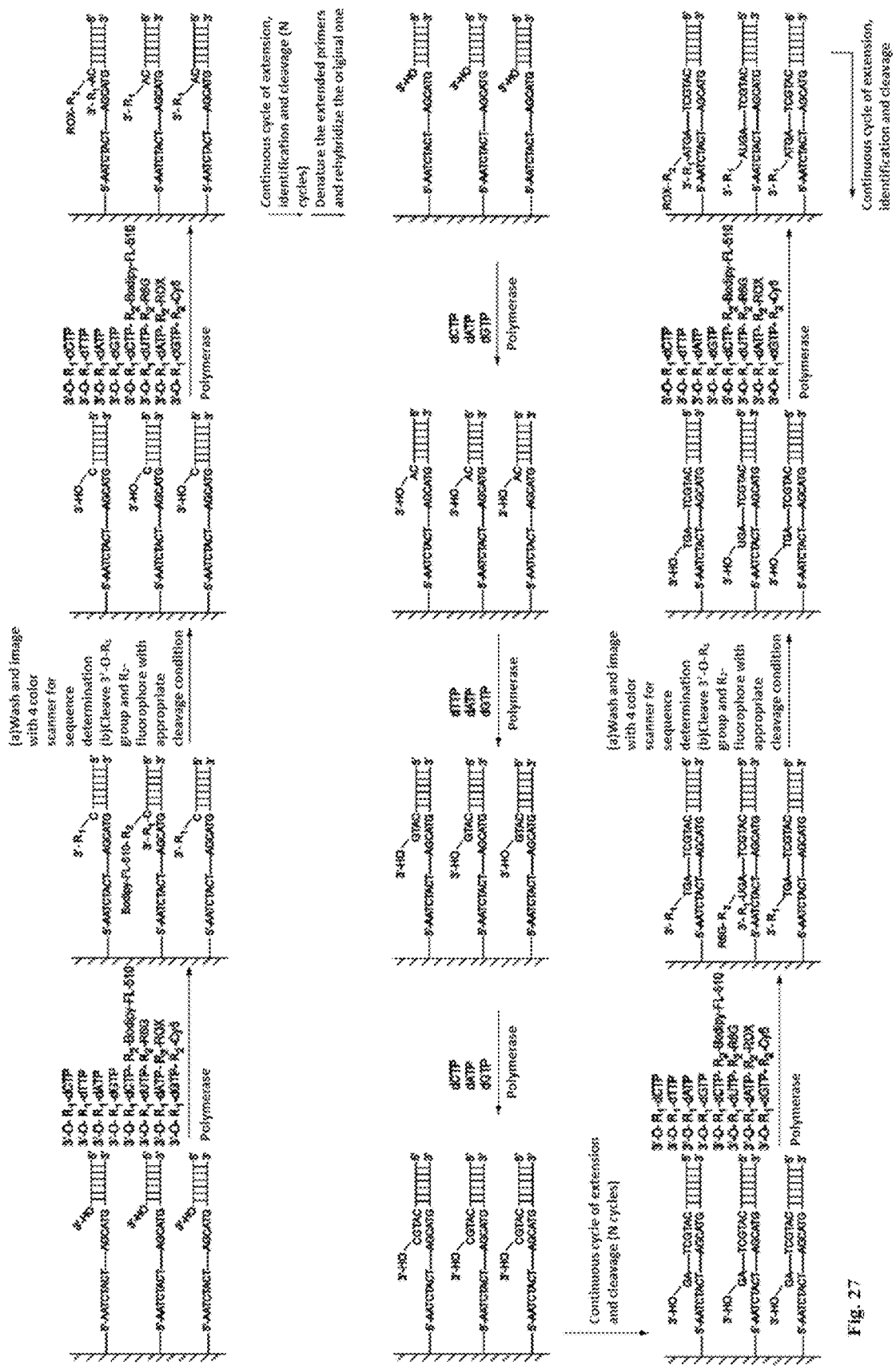
FIG. 27. Template "Walking" Method 2 for SBS with C—F-NRTs
Figure 28:
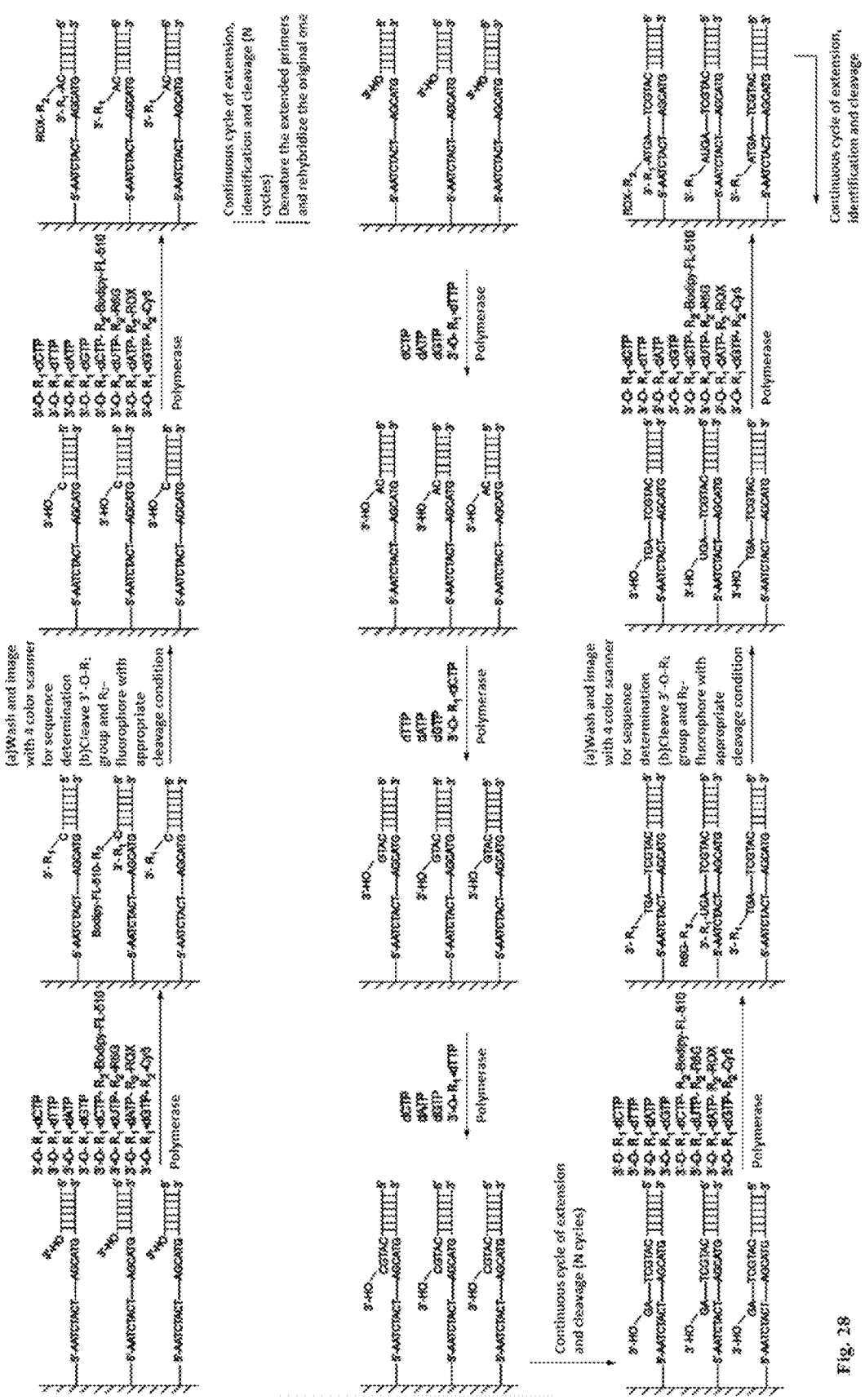
FIG. 28. Template "Walking" Method 3 for SBS with C—F-NRTs
Figure 29:
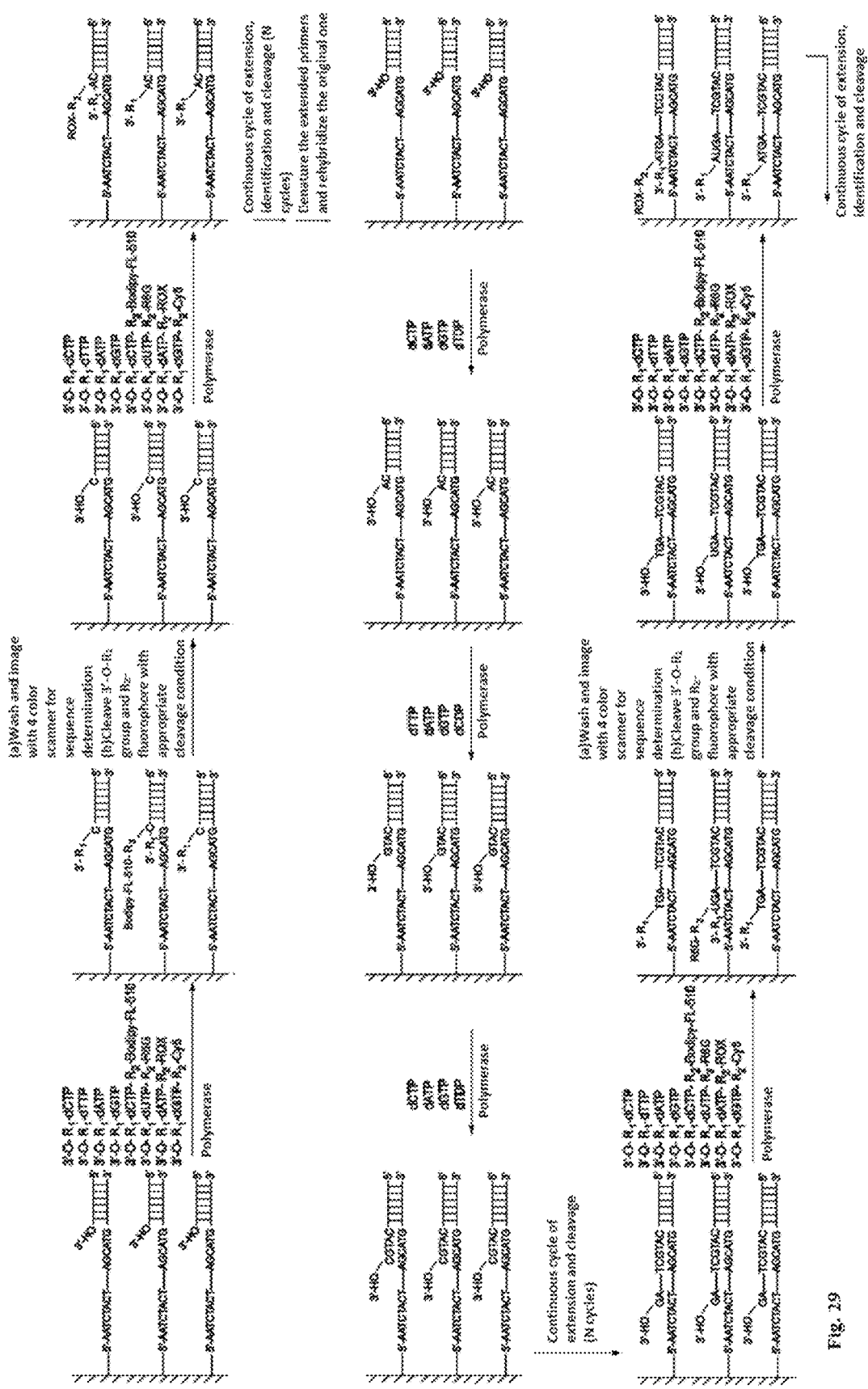
FIG. 29. Template "Walking" Method 4 for SBS with C—F-NRTs
Figure 30:
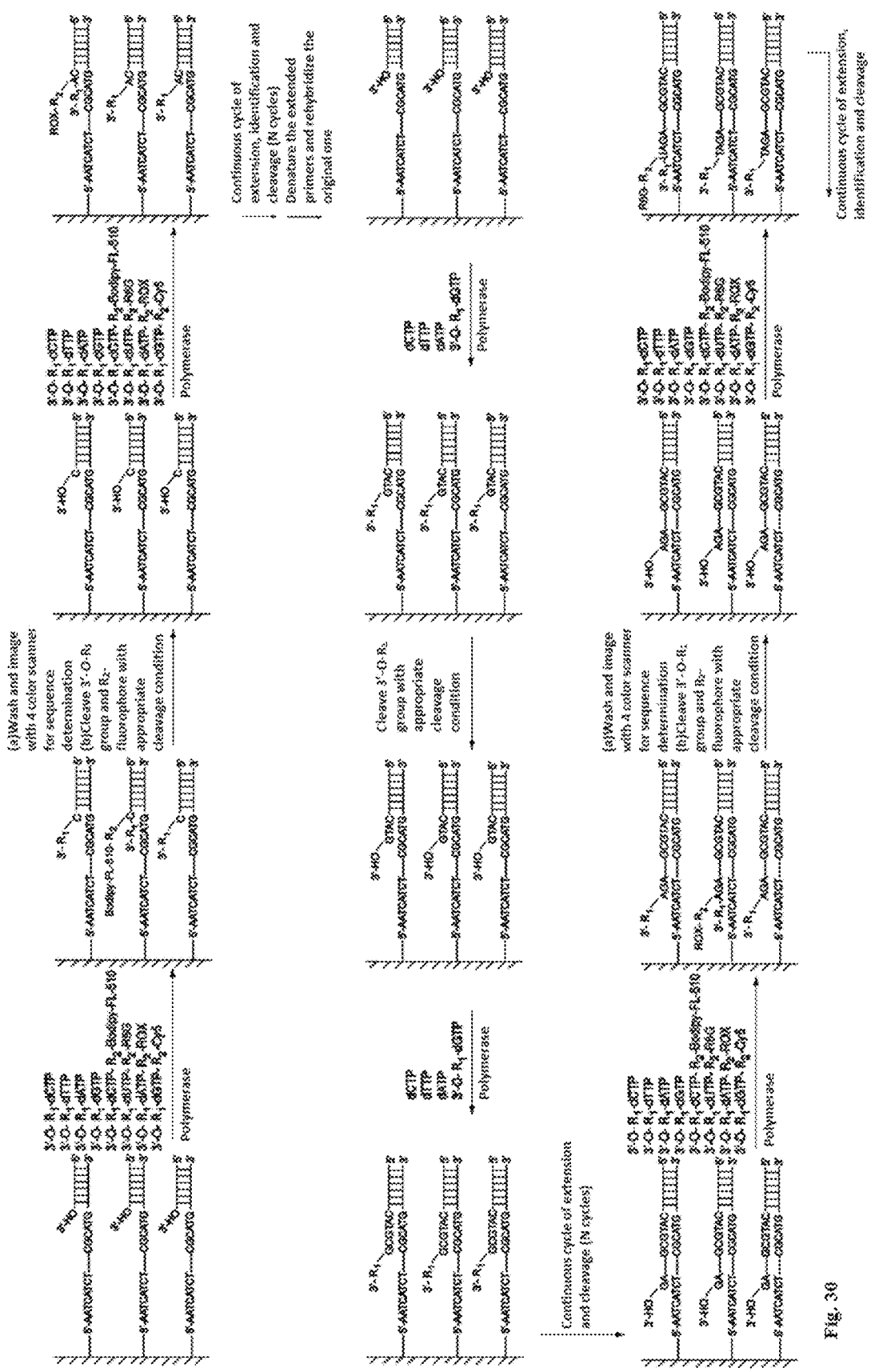
FIG. 30. Template "Walking" Method 5 for SBS with C—F-NRTs

Four 3'-O—N$_3$-dNTPs-N$_3$-fluorophore (FIG. 24) and four 3'-O—N$_3$-dNTPs (FIG. 18) were synthesized, using an azidomethyl group as a chemically reversible capping moiety in the 3'-O-modified C—F-NRTs and C-NRTs, and an azido-based cleavable linker to attach the fluorophores to the C—F-NRTs, After fluorescence detection for sequence determination, the azidomethyl capping moiety on the 3'-OH and the fluorophore attached to the DNA extension product via the azido-based cleavable linker are efficiently removed using tris(2-carboxyethyl)phosphine (TCEP) in aqueous solution compatible with DNA. Various DNA templates, including those with homopolymer regions were accurately sequenced with read length of over 20 bases using this SBS method on a chip and a four-color fluorescent scanner (FIG. 25).

Four C—F-NRTs (3'-O—N$_3$-dNTPs-N$_3$-fluorophore) were synthesize along with four C-NRTs (3'-O—N$_3$-dNTPs) for the implementation of our four-color de novo DNA sequencing by synthesis approach. During the incorporation stage of SBS, a mixture of the two sets of NRTs is used to extend the DNA strand. Only a small percentage of the 3'-O—N$_3$-dNTPs-N$_3$-fluorophore is used in the mixture so that the majority of the product is extended with the less bulky 3'-O—N$_3$-dNTPs. This approach leads to a more efficient DNA polymerase reaction since the smaller 3'-O—N$_3$-dNTPs are much easier to incorporate. Another advantage of having most of the DNA extended with 3'-O—N$_3$-dNTPs is the fact that after cleavage of the 3'-OH capping group on the product, nascent strand of DNA that have no traces of modification is restored. Such DNA does not have any adverse effect on the DNA polymerase during the subsequent incorporation of the complementary nucleotide. For DNA extended with the 3'-O—N$_3$-dNTPs-N$_3$-fluorophore, which serve as the signal producer, the 3'-OH is also restored after the cleavage step so that the next stage of SBS can be carried out. Therefore, it is possible to recover all the DNA templates after each round of sequencing, dramatically increasing the potential read-length of our SBS methodology. After the incorporation reaction, two separate capping steps, first with 3'-O—N$_3$-dNTPs and then with ddNTPs, are performed. The rationale behind the first capping reaction is to maximize the amount of extension products and to ensure the minimal loss of templates. In case there is any un-extended product after the first capping step, the second capping with ddNTPs is mostly likely to permanently terminate these DNA strands so that all templates are synchronized. Without these precautionary synchronization procedures, mixed fluorescent signals will prevent the identification of the correct nucleotide incorporated. Since both 3'-O—N$_3$-dNTPs-N$_3$-fluorophore and 3'-O—N$_3$- dNTPs are reversible terminators, which allow the sequencing of each base in a serial manner, they can accurately determine the homopolymeric regions of DNA. In addition, due to the fact that all of the steps of our SBS approach are performed on a DNA chip, there is no longer a need for electrophoretic DNA fragment separation as in the classical Sanger sequencing method.

Even though theoretically SBS with C—F-NRTs can be executed without losing templates, the utilization of ddNTPs capping does reduce the number of available templates during the actual sequencing reaction. In addition, the incorporation and cleavage of C—F-NRTs leave a tail on the modified nucleotides that can potentially reduce the incorporation efficiency the subsequent base. Hence template "walking" can be applied to increase read length for this SBS methodology.

2. Template "Walking"

Immediately after the first round of SBS, DNA templates are denatured by heat or mild alkali conditions to rid of the extended primer. The same original primer is re-hybridized to the template chain, and one of the five "walking" methods described in the previous section can be applied to reset the start point for the next round of SBS at the end of the first sequencing run (FIGS. 26, 27, 28, 29, and 30).

3. Re-Initiation of SBS with C—F-NRTs

Once the "walking" process is completed, the primer is extended to the end of the previous round of SBS. At this point, hybrid SBS is carried out to identify the subsequent bases. If the process can be repeated more times, it should be theoretically possible to achieve long and significant read length.

Strategy 2: Template "Walking" with Universal Bases

Figure 31:
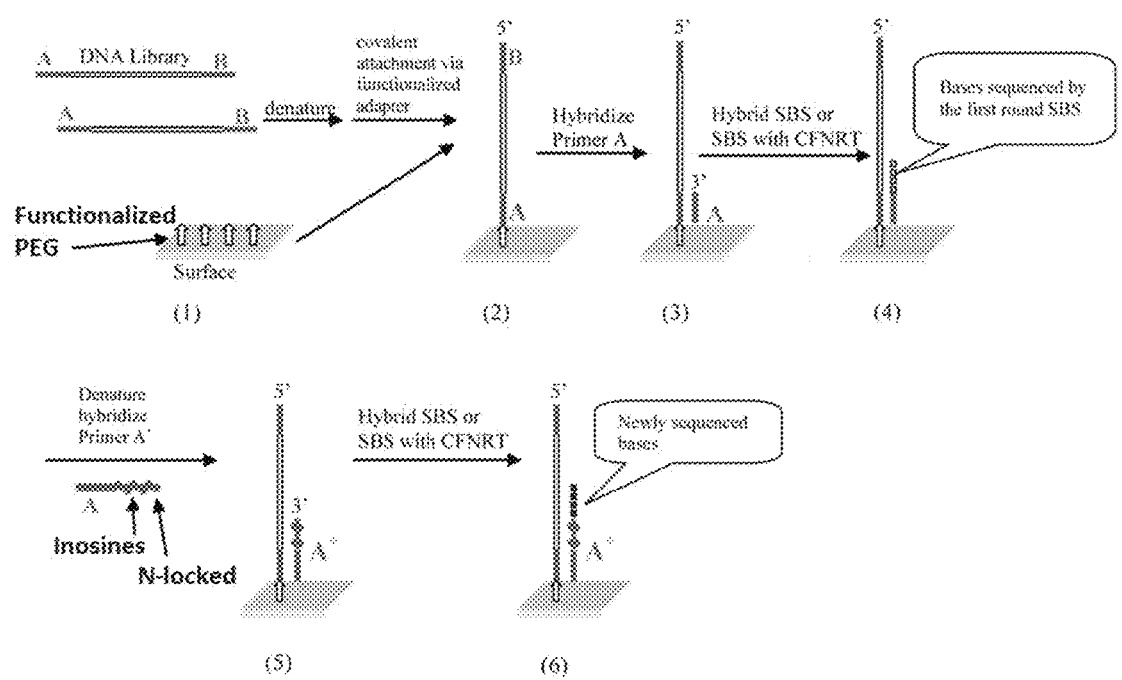
FIG. 31. "Walking" Strategy 2

In this variation on the Strategy 1, the reset is achieved not with nucleotide walking, but with the use of a longer primer partially consisting of universal nucleotides for the second round. Attachment of the template DNA to the surface and the first few steps of the procedure are identical to the first method. However, after stripping the first extended primer for the initial 20 base readout, a long primer with the following features will be hybridized to the template: (a) the first half is identical to the initial primer; (b) the second half is composed almost entirely of universal bases. One possible candidate for the universal base is inosine, which, in its deoxynucleoside form, can base pair with all four nucleotides, though its affinity for C and A is significantly higher than for G and T; a second possibility is 5-nitroindole; (c) the last one or two anchoring bases of the long primers are degenerate with each of the four possible bases being represented. Because the universal bases can form hydrogen bonds with any of the other four bases with some efficiency, they have the capacity to bind to the first 20 or so bases of the sequence. However, the melting temperature of the ensuing hybridization is reduced substantially by the run of inosines, a few of the bases in the first half and the two 3'-anchoring bases can be substituted with locked nucleotides. Locked nucleic acids have a chemical bond between the 2' and 4' carbons of the ribose. While slower to associate with their complementary base, once hybridized, they tend not to dissociate. Thus, they provide a nice solution to ensure that the long primer remains attached appropriately to the template. In addition, the percentage of locked nucleosides in the primer can be manipulated to achieve higher hybridization strength. After hybridization of the above long primer, a second round of either Hybrid SBS or SBS with C—F-NRTs can be performed (FIG. 31).

An alternative approach to Strategy 2 is the use of a detachable loop primer, possibly with a labile sugar and glycosylase treatment. After the first round of sequencing, the loop is removed by enzymatic cleavage and denaturation, and then a new identical loop is attached. In a modification that is a composite of "walking" Strategy 1 and 2, the new loop primer can be composed of an initial portion identical to the first loop primer, a "loop out" region that bypasses the first set of sequenced nucleotides, and a degenerate anchoring nucleotide to initiate the second round of sequencing.

Strategy 3: Multiple Primers "Walking"

In this third strategy, one or two additional primer annealing sites are introduced into the DNA to be sequenced at a distance just about equal to the number of bases that can be sequenced from the first primer.

Figure 32:
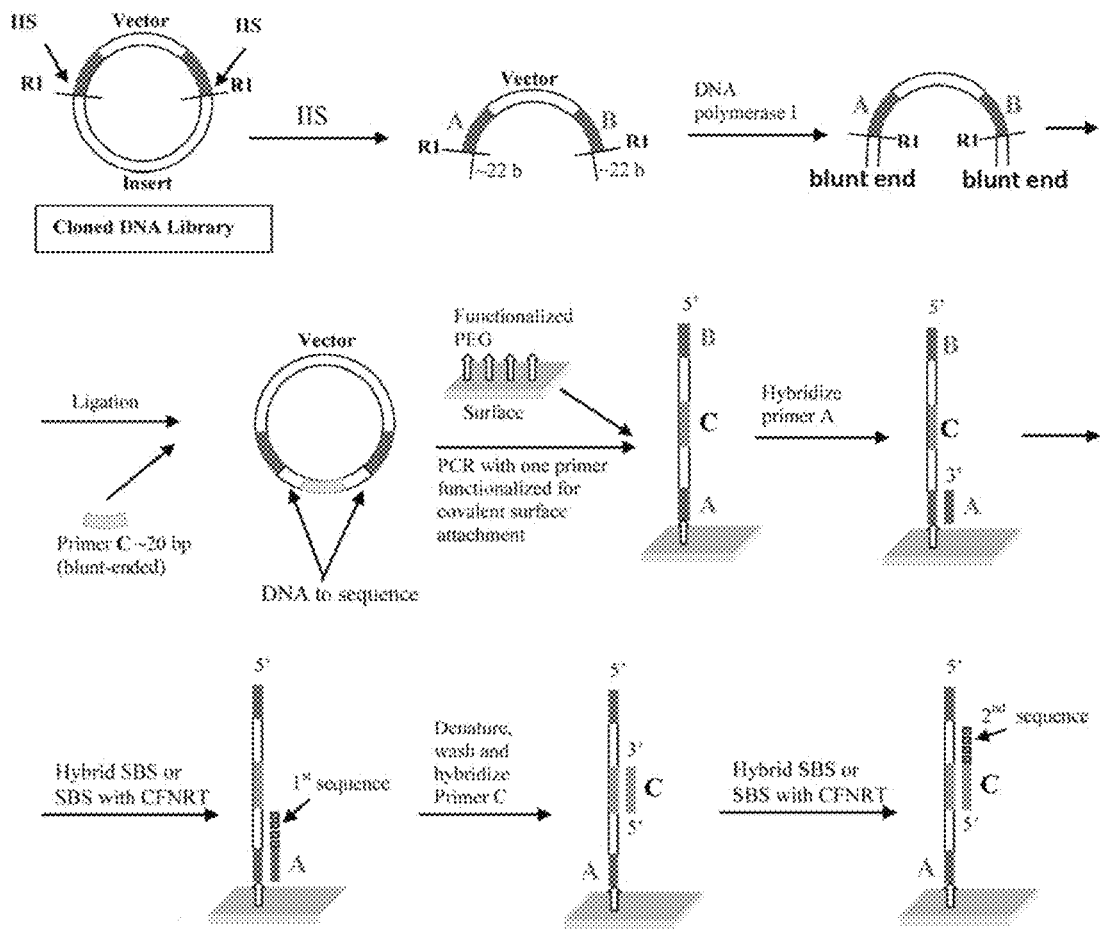
FIG. 32. "Walking" Strategy 3

As illustrated in FIG. 32, template preparation for SBS will utilize the cloning of genomic DNA into a specially designed vector containing type IIS or III restriction sites (MmeI and EcoP15 I) flanking the genomic DNA cloning site. In this procedure size fractionated DNA (minimal length 100 bp) will be ligated into the cloning vector using blunt-end ligation. Upon cloning, the resulting recombinant plasmids will be re-cut at one of the type IIS/III sites and the sticky ends will be filled in with Klenow enzyme. Next, specific sequencing primers will be introduced via ligation inside the genomic DNA inserts, 22 bases distant from the first primer in the case of MmeI or 27 bases away in the case of EcoP15 I. After insertion of the internal priming sites, the constructs will be re-cloned in E. coli, the recombinant plasmids isolated and the inserts re-amplified by PCR at vector-insert junctions and attached to the beads for sequencing. Alternatively, emulsion or polony PCR strategies can be used to accomplish attachment of single molecules to individual beads or slide locations and their subsequent amplification at a much lower cost than cloning. In any case, once the DNA is immobilized, the first round of Hybrid SBS or SBS with C—F-NRTs will be primed from the flanking primer, then after stripping these extended primers, the second set of sequencing reactions will be initiated at the internal primer. It should be noted that with this scheme, the two sequenced portions come from opposite ends of the initial DNA, and are in essence paired end reads.

Several novel modifications of this approach can address the desire of many investigators to sequence an entire 100-base stretch of DNA, the length of a typical exon including surrounding intronic bases adjacent to the splice site. For instance, one can prepare a construct with two internal primers. In this case, the initial vector will be designed with MmeI at one flank and EcoP15I on the other; using two consecutive restriction, cloning and circularization steps, the final construct will consist of four alternative priming sites (two on the insert flanks and two internal), which in the case of 100 bp segments of genomic DNA will guarantee their complete sequencing with 25-30 cycles of SBS and three primer resets. The extra cycles would enable some of the sequence reads to run into the next primer, which would help to confirm the direction (e.g., the last sequence might end with the MmeI or EcoP15I site. Other tricks would include modifying the ends of the primers to allow looping and reverse direction sequencing, incorporation of one or two decoding bases in the internal primers to confirm directions, and deconvoluting the results after all the data is generated. One would want to have a single set of primers for sequencing, regardless of which strand is attached. In order to achieve this, and to overcome the non-directional nature of their insertion, the internal primer or primers will be designed as palindromes so that sequencing can be initiated in either direction.

Materials and Methods
DNA Polymerase Reaction Using Four Photocleavable Fluorescent Dideoxynucleotides.

It was previously demonstrated that a library of nucleotide analogue, dNTPs-PC-fluorophore, can be efficiently incorporated by DNA polymerase in a DNA extension reaction and the fluorophore can be effectively cleaved off by laser irradiation at 355 nm (1-4). Here, four dideoxynucleotide analogues have been characterized, ddCTP-PC-Bodipy-FL-510, ddUTP-PC-R6G, ddATP-PC-ROX and ddGTP-PC-Bodipy-650 that were used for SBS on a chip by performing four separate DNA-extension reactions, each with a different template allowing the four ddNTP analogues to be incorporated. The self-priming template (a 26-mer hairpin DNA with a 4-base 5'-overhang) sequences were (5'-GACT-GCGCCGCGCCTTGGCGCGGCGC-3' (SEQ ID No:1)) for ddATP-PC-ROX incorporation, (5'-ATCGGCGC-CGCGCCTTGGCGCGGCGC-3' (SEQ ID No:2)) for ddCTP-Bodipy-FL-510 incorporation, (5'-GATCGCGC-CGCGCCTTGGCGCGGCGC-3' (SEQ ID No:3)) for ddGTP-PC-Bodipy-650 incorporation and (5'-GTCA-GCGCCGCGCCTTGGCGCGGCGC-3' (SEQ ID No:4)) for ddUTP-PC-R6G incorporation. Each of the extension reactions consisted of using a mixture of all four ddNTPs-PC-fluorophore (120 pmol of ddCTP-PC-Bodipy-FL-510, 120 pmol of ddUTP-PC-R6G, 120 pmol of ddATP-PC-ROX and 120 pmol of ddGTP-PC-Bodipy-650) along with 60 pmol of the self-priming template, 2 μL of 10× Thermopol reaction buffer (New England Biolabs), and 2 units of 9° N mutant DNA polymerase (exo-) A485L/Y409V in a total reaction volume of 20 μL. The reaction consisted of incubations at 94° C. for 5 min, 4° C. for 5 min, and 62° C. for 20 min. Subsequently, the extension product was purified by using a reverse-phase HPLC. An Xterra MS C18 (4.6×50-mm) column (Waters) was used for the HPLC analysis. Elution was performed over 120 minutes at a flow rate of 0.5 mL/min with the temperature set at 50° C. by using a linear gradient (12-34.5%) of methanol in a buffer consisting of 8.6 mM triethylamine and 100 mM hexafluoroisopropyl alcohol (pH 8.1). The fraction containing the desired product was collected and freeze-dried for mass spectrometry analysis using Voyager DETM MALDI-TOF mass spectrometer (Applied Biosystems) and photocleavage. For photocleavage, the purified DNA extension product bearing the deoxynucleotide analogue was resuspended in 200 μL of deionized water. The mixture was irradiated using a laser for 10 seconds at 355 nm and then analyzed by MALDI-TOF MS. After photocleavage, the DNA fragment with the fluorophore removed was used as a primer for a second extension reaction using dGTP-PC-Bodipy-FL-510 (reaction mixture described above). The second extended product was then purified by HPLC as described previously and photolyzed. The third extension using dATP-PC-ROX and the fourth extension using dCTP-PC-Bodipy-650 were carried out in a same manner using the previously extended and photocleaved product as their primer.

Continuous DNA Polymerase Reaction Using Four 3'-O-Modified Photocleavable Nucleotides as Reversible Terminators in Solution.

The four nucleotide analogues 3'-O-PC-dATP, 3'-O-PC-dCTP, 3'-O-PC-dGTP and 3'-O-PC-dTTP have been characterized, by performing four continuous DNA-extension reactions sequentially using a primer (5'-AGAGGATC-CAACCGAGAC-3' (SEQ ID No:5)) and a synthetic 60-mer DNA template (5'-GTGTACATCAACATCACCTACCAC-CATGTCA-GTCTCGGTTGGATCCTCTATTGTGTC-CGG-3' (SEQ ID No:6)) based on a portion of exon 7 of the human p53 gene. The four nucleotides in the template immediately adjacent to the annealing site of the primer are 3'-ACTG-5' (SEQ ID No:7). First, a polymerase extension reaction using a pool of all four nucleotide analogues along with the primer and the template was performed producing a single base extension product. The reaction mixture for this, and all subsequent extension reactions, consisted of 80 pmol of template, 60 pmol of primer, 120 pmol of 3'-O-PC-dNTPs, 1× Thermopol II reaction buffer, 40 nmol of Mn2+ and 2 units of 9° N mutant DNA polymerase (exo-) A485L/Y409V in a total reaction volume of 20 μL. The reaction consisted of 20 cycles at 94° C. for 20 sec, 48° C. for 40 sec, and 62° C. for 90 sec. Subsequently, the extension product was purified by using reverse-phase HPLC. The fraction containing the desired DNA product was collected and freeze-dried for analysis using MALDI-TOF mass spectrometry. For photocleavage, the purified DNA extension product bearing the 3'-O-modified nucleotide analogue was resuspended in 200 μL of deionized water. The mixture was then irradiated using a laser for 10 seconds at 355 nm and characterized by MALDI-TOF MS. The DNA product with the 3'-O-(2-nitrobenzyl) group removed to generate a free 3'-OH group was used as a primer for a second extension reaction using 3'-O-PC-dNTPs. The second extended DNA product was then purified by HPLC and photocleaved. The third and the fourth extensions were carried out in a similar manner using the previously extended and photocleaved product as the primer.

4-Color DNA Sequencing by Synthesis on a Chip Using Photocleavable Fluorescent Dideoxynucleotide/3'-Modified Photocleavable Nucleotide Combination Remnant of Sanger Sequencing.

Ten microliters of a solution consisting of ddCTP-PC-Bodipy-FL-510 (25 fmol), ddUTP-PC-R6G (50 fmol), ddATP-PC-ROX (100 fmol), ddGTP-PC-Bodipy-650 (100 fmol), 3'-O-PC-dATP (14 pmol), 3'-O-PC-dCTP (3.5 pmol), 3'-O-PC-dGTP (14 pmol), 3'-O-PC-dTTP (7 pmol) [a 3'-O-PC-dNTPs:ddNTPs-PC-fluorophore ratio of 140:1], 1 U of 9° N mutant DNA polymerase, and 1× reaction buffer was spotted on the surface of the chip, where the self-primed DNA moiety was immobilized. The base complementary to the DNA template was allowed to incorporate into the primer at 62° C. for 10 min. To synchronize any unincorporated templates, an extension solution consisting of 30 pmol each of 3'-O-PC-dCTP, 3'-O-PC-dTTP, 3'-O-PC-dATP and 3'-O-PC-dGTP, 1 U of 9° N mutant DNA polymerase, and 1× reaction buffer was spotted on the same spot and incubated at 62° C. for 10 min. After washing the chip with a SPSC buffer containing 0.1% Tween 20 for 1 min, the surface was rinsed with dH$_2$O, dried briefly and then scanned with a 4-color ScanArray Express scanner (Perkin-Elmer Life Sciences) to detect the fluorescence signal. The 4-color scanner is equipped with four lasers with excitation wavelengths of 488, 543, 594, and 633 nm and emission filters centered at 522, 570, 614, and 670 nm. To perform the photocleavage, the glass chip was placed inside a chamber filled with dH$_2$O/acetonitrile (1/1 v/v) solution and the spot where the self-primed DNA moiety is immobilized was irradiated for 1 min with a laser at 355 nm. After washing the surface with dH$_2$O, the chip was scanned again to compare the intensity of fluorescence after photocleavage with the original fluorescence intensity. This process was followed by the next polymerase extension reaction using the ddNTPs-PC-fluorophore/3'-O-PC-dNTPs combination mixture (ratio adjusted to 120:1, with concentration of ddNTPs-PC-fluorophore remaining the same), with the subsequent synchronization, washing, fluorescence detection, and photocleavage processes performed as described above. With each subsequent polymerase extension reaction, the ratio was adjusted, decreasing in increments of 20 (100:1 to 80:1 to 60:1 and so on), until the mixture consisted only of ddNTPs-PC-fluorophore. This SBS cycle was repeated multiple times using the combination mixture of ddNTPs-PC-fluorophore/3'-O-PC-dNTPs in each polymerase extension reaction to obtain de novo DNA sequencing data on a DNA template immobilized on a chip.

Discussion

Four photocleavable fluorescent dideoxynucleotide analogues have been synthesized and characterized along with four 3'-O-modified photocleavable reversible terminator nucleotides and used them to produce 4-color de novo DNA sequencing data on a chip by Sanger/SBS hybrid sequencing approach. In doing so, the combining of the advantageous aspects of Sanger and SBS sequencing approaches to sequence DNA unambiguously was achieved. First, a strategy to use a photocleavable reversible moiety to cap the 3'-OH group of the nucleotide has been successfully implemented so that the nucleotide temporarily terminates the polymerase reaction to allow the identification of the incorporated photocleavable fluorescent dideoxynucleotide. After photolysis, both the fluorophore from the dideoxynucleotide and the 2-nitrobenzyl group from the 3'-O-PC modified reversible terminator are removed. Removal of the fluorophore after the identification of the base is crucial so that it does not interfere with the fluorescence detection of the next incorporated base. Regeneration of the 3'-OH group is needed for the subsequent incorporation of the next complementary base. With these 3'-O-modified reversible terminators, after photocleavage, there are no traces of modification, thereby regenerating a natural nucleotide at the terminal 3'-end of growing DNA strand. Furthermore, photocleavage reaction is catalyzed by photons and introduces no additional chemical reagents to cleave the fluorophore and the 3'-O-(2-nitrobenzyl) group, which eliminates possible chemical residue contamination during the subsequent polymerase reaction. Therefore, there will be no adverse effect on the DNA polymerase for the incorporation of the next complementary base. Second, both these modified dideoxynucleotide and nucleotide analogues are terminators (permanent and reversible) which allow the interrogation of each base in a serial manner, a key procedure enabling accurate determination of homopolymeric regions of DNA template. Because the fluorescence-driven base identification is made as each complementary base is incorporated and subsequently cleaved off, it enables the elimination of DNA fragment separation procedure. It also allows for the addition of all 8 substrates simultaneously in performing Sanger/SBS hybrid sequencing. This ultimately reduces the number of cycles needed to complete the sequencing cycle, increases sequencing accuracy due to competition among the substrates in the polymerase reaction.

The key factors governing the sequencing readlength of our 4-color Sanger/SBS hybrid sequencing approach are: 1) the purity of 3'-O-modified photocleavable reversible terminators. Any impurities even in small amounts, such as nucleotides with a free 3'-OH, where the capping group has come off, will significantly affect the synchrony of the DNA extension; 2) the ratio of 3'-O-PC-dNTPs to ddNTPs-PC-fluorophore. Because the amount of self-priming DNA template is set before the first incorporation, during each polymerase reaction, most of the DNA self-priming DNA template should be extended with 3'-O-modified reversible terminators and only fractional amount extended with fluorescent dideoxynucleotides. Once the dideoxynucleotides incorporate into the growing DNA strand, that strand no longer will participate in further DNA synthesis. One way to achieve this is to have a large 3'-O-PC-dNTPs to ddNTPs-PC-fluorophore ratio so that it will lead to prolonged DNA extension.

Due to the high detection sensitivity of the scanner, small amount of fluorophore is sufficient to detect its fluorescence emission; 3) the yield of cleavage of the fluorophore and the 3'-OH capping group from the DNA extension products. The photocleavage has near quantitative yield in solution phase experiments. The yield on the surface is difficult to measure precisely due to the small non-specific absorption of fluorophores affecting the background fluorescence level. The strong fluorescence signal to background ratio (~20:1) seen in FIG. 5 indicates that the readlength should be able to be extended even further. A signal to background ratio of 3 or 4 to 1 should be sufficient to accurately determine the DNA sequence. In terms of readlength, Sanger sequencing holds the standard with readlength of over 700 bp, which is encouraging for this hybrid sequencing approach. With the massive parallel output capability, this hybrid approach may potentially achieve the necessary throughput and cost reduction that defines the next-generation sequencing platform. The basic principle and strategy outlined in the 4-color Sanger/SBS hybrid approach will be built on by improving in the areas of DNA extension methodology with engineering of high performance polymerases tailored for both the photocleavable fluorescent dideoxynucleotides and 3'-O-modified reversible terminators, as well as investigating into alternative cleavable linkers and 3'-OH reversible capping moieties.

REFERENCES

1. Lander, E. S., L. M. Linton, et al. (2001) Initial sequencing and analysis of the human genome. Nature 409, 860-921.
2. Sanger, F., S. Nicklen, et al. (1977) DNA sequencing with chain-terminating inhibitors. Proc Natl Acad Sci USA 74, 5463-5467.
3. Ju, J., Ruan, C., Fuller, C. W., Glazer, A. N. & Mathies, R. A. (1995) Proc Natl Acad Sci USA 92, 4347-4351.
4. Tabor, S. & Richarson, C. C. (1995) Proc. Natl. Acad. Sci. USA 92, 6339-6343.
5. Smith, L. M., Sanders, J. Z., Kaiser, R. J., Hughes, P., Dodd, C., Connell, C. R., Heiner, C., Kent, S. B. & Hood, L. E. (1986) Nature 321, 674-679.
6. Meldrum, D. (2000) Automation for genomics. Part I. Preparation for sequencing. Genome Res. 10, 1081-1092.
7. Marziali, A., Willis, T. D., Federspiel, N. A. & Davis, R. W. (1999) An automated sample preparation system for large-scale DNA sequencing. Genome Res. 9, 457-462.
8. Ewing, B. & Green, P. (1998) Base-calling of automated sequencer traces using phred II. Error probabilities. Genome Res. 8, 186-194.
9. Ewing, B., Hillier, L., Wendl, M. C. & Green, P. (1998) Base-calling of automated sequencer traces using phred I. Accuracy assessment. Genome Res. 8, 175-185.
10. Marra, M., L. A. Weinstock, et al. (1996) End sequence determination from large insert clones using energy transfer fluorescent primers. Genome Res 6, 1118-1122.
11. Lee, L. G., S. L. Spurgeon, et al. (1997) New energy transfer dyes for DNA sequencing. Nucleic Acids Res 25, 2816-2822.
12. Heiner, C. R., K. L. Hunkapiller, et al. (1998) Sequencing multimegabase-template DNA with BigDye terminator chemistry. Genome Res 8, 557-561.

13. Dovichi, N. J. (1997) DNA sequencing by capillary electrophoresis. Electrophoresis 18, 2393-2399.
14. Zhou, H., et al. (2000) DNA sequencing up to 1300 bases in 2 h by capillary electrophoresis with mixed replaceable linear polyacrylamide solutions. Anal. Chem. 72, 1045-1052.
15. Stellwagen, E., Lu, Y. & Stellwagen, N. C. (2003) Unified description of electrophoresis and diffusion for DNA and other polyions. Biochemistry 42, 11745-11750.
16. Collins, F. S., Green, E. D., Guttmacher, A. E. & Guyer, M. S. (2003) A vision for the future of genomics research. Nature 422, 835-847.
17. (grants.nih.gov/grants/guide/rfa-files/RFA-HG-04-002.html)
18. (grants.nih.gov/grants/guide/rfa-files/RFA-HG-04-003.html)
19. (genomics.xprize.org/)
20. Shaffer C. (2007) Next generation sequencing outpaces expectations. Nat. Biotechnology. 25, 149.
21. Consortium, I. H. G. S. (2004) Finishing the euchromatic sequence of the human genome. Nature 431, 931-945.
22. Smith, L. M., J. Z. Sanders, et al. (1986) Fluorescence detection in automated DNA sequence analysis. Nature 321, 674-679.
23. Prober, J. M., G. L. Trainor, et al. (1987) A system for rapid DNA sequencing with fluorescent chain-terminating dideoxynucleotides. Science 238, 336-341.
24. Ju, J., C. Ruan, et al. (1995) Fluorescence energy transfer dye-labeled primers for DNA sequencing and analysis. Proc Natl Acad Sci USA 92, 4347-4351.
25. Ronaghi, M., M. Uhlen, et al. (1998) A sequencing method based on real-time pyrophosphate. Science 281, 363, 365.
26. Margulies, M., M. Egholm, et al. (2005) Genome sequencing in microfabricated high-density picoliter reactors. Nature 437:376-380.
27. Fu, D. J., Tang, K., Braun, A., Reuter, D., Darnhofer-Demar, B., Little, D. P., O'Donnell, M. J., Cantor, C. R. & Koster, H. (1998) Nat Biotechnol 16, 381-384.
28. Roskey, M. T., Juhasz, P., Smirnov, I. P., Takach, E. J., Martin, S. A. & Haff, L. A. (1996) Proc Natl Acad Sci USA 93, 4724-4729.
29. Edwards, J. R., Itagaki, Y. & Ju, J. (2001) Nucleic Acids Res 29, E104-4.
30. Kasianowicz, J. J., Brandin, E., Branton, D. & Deamer, D. W. (1996) Proc Natl Acad Sci USA 93, 13770-13773.
31. Braslaysky, I., Hebert, B., Kartalov, E. & Quake, S. R. (2003) Proc Natl Acad Sci USA 100, 3960-3964.
32. Shendure, J., Porreca, G. J., Reppas, N. B., Lin, X., McCutcheon, J. P., Rosenbaum, A. M., Wang, M. D., Zhang, K., Mitra, R. D. & Church, G. M. (2005) Science 309, 1728-1732.
33. Ju J, Kim D H, Bi L, Meng Q, Bai X, Li Z, Li X, Marma M S, Shi S, Wu J, Edwards J R, Romu A, Turro N J. (2006) Proc. Natl. Acad. Sci. USA. 103, 19635-40.

What is claimed is:

1. A method for determining the identity of each of a series of consecutive nucleotide residues in a nucleic acid comprising:

a) contacting a plurality of the nucleic acids with (i) at least four different dideoxynucleotide analogues, each having the structure:

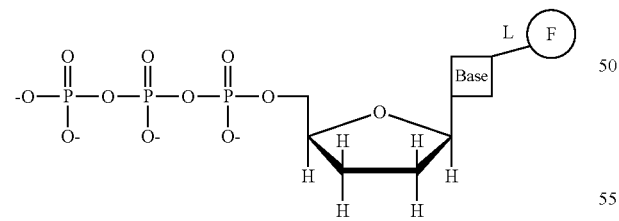

wherein F is a fluorophore, L is a cleavable linker, the base is adenine, guanine, cytosine, uracil or thymine, wherein the fluorophore attached through the cleavable linker to each type of base differs in its emission or excitation spectra from a fluorophore attached to each of the remaining types of bases, and each of the four dideoxynucleotide analogues differs from the remaining three dideoxynucleotide analogues by having a different base, (ii) at least four deoxynucleotide analogues having the structure:

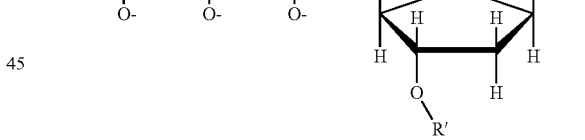

wherein B is a base and is adenine, guanine, cytosine, uracil, or thymine, and wherein R' is a cleavable chemical group, wherein each of the four deoxynucleotide analogues differs from the remaining three deoxynucleotide analogues by having a different base, (iii) a nucleic acid polymerase and (iv) a plurality of nucleic acid primers which can each hybridize with a nucleic acid of the plurality of nucleic acids, under conditions permitting (a) one of the four dideoxynucleotide analogues that is complementary to the consecutive nucleotide residue to be identified to form a phosphodiester bond with the 3' end of one of the nucleic acid primers and thereby extend the primer and (b) one of the four dNTP analogues that is complementary to a consecutive nucleotide residue to be identified to form a phosphodiester bond with the 3' end of another one of the nucleic acid primers and thereby extend that primer;

b) identifying the fluorophore of the dideoxynucleotide analogue which has formed the phosphodiester bond, thereby identifying the consecutive nucleotide;
c) cleaving the cleavable linker attaching the fluorophore of the dideoxynucleotide analogue which has formed the phosphodiester bond and cleaving the cleavable chemical group from the deoxynucleotide analogue which has formed the phosphodiester bond;
d) iteratively repeating steps a) through c) for each of the consecutive nucleotide residues to be identified until a final consecutive nucleotide residue is to be identified;
e) repeating steps a) and b) to identify the final consecutive nucleotide residue,
f) denaturing the extended primers so that they dehybridize from the plurality of nucleic acids;
g) 1) contacting the plurality of nucleic acids from steps a) through f) with (i) at least four different deoxynucleotide triphosphate (dNTP) analogues, each comprising a base chosen from adenine, thymine, cytosine, uracil, inosine, or 5-nitroindole each differing from a deoxynucleotide triphosphate by having a cleavable chemical group attached to the 3' O-atom of the dNTP analogue, (ii) a nucleic acid polymerase and (iii) a plurality of second nucleic acid primers which can each hybridize with a nucleic acid of the plurality of nucleic acids, under conditions permitting one of the four dNTP analogues that is complementary to the consecutive nucleotide residue to be identified to form a phosphodiester bond with the 3' end of one of the second nucleic acid primers and thereby extend that second primer, and
   cleaving the chemical group from the 3' O-atom of the dNTP analogue which has formed the phosphodiester bond so as to thereby permit incorporation of a further dNTP analogue into the extended second nucleic acid primer; or
2) (I) contacting the plurality of nucleic acids from steps a) through f) with (i) three different types of deoxynucleotide triphosphate, (ii) a nucleic acid polymerase and (iii) a plurality of second nucleic acid primers which can each hybridize with a nucleic acid of the plurality of nucleic acids, under conditions permitting one of the three deoxynucleotide triphosphates that is complementary to the consecutive nucleotide residue to be identified to form a phosphodiester bond with the 3' end of one of the second nucleic acid primers and thereby extend the second nucleic acid primer, and
   (II) contacting the plurality of nucleic acids with (i) three different types of deoxynucleotide triphosphate, wherein at least one of the types of deoxynucleotide triphosphate is not used in step (I), under conditions permitting one of the three deoxynucleotide triphosphates that is complementary to the consecutive nucleotide residue to be identified to form a phosphodiester bond with the 3' end of one of the extended second nucleic acid primers and thereby further extend the second nucleic acid primer; or
3) contacting the plurality of nucleic acids from steps a) through f) with (i) three different types of deoxynucleotide triphosphates, (ii) a deoxynucleotide triphosphate analogue, differing from a deoxynucleotide triphosphate by having a cleavable chemical group attached to the 3' O-atom of the deoxynucleotide triphosphate analogue and differing from the three different types of deoxynucleotide triphosphates by having a different base therefrom, (iii) a nucleic acid polymerase and (iv) a plurality of second nucleic acid primers which can each hybridize with a nucleic acid of the plurality of nucleic acids, under conditions permitting one of the three deoxynucleotide triphosphates or the deoxynucleotide triphosphate analogue that is complementary to the consecutive nucleotide residue to be identified to form a phosphodiester bond with the 3' end of one of the second nucleic acid primers and thereby extend that second nucleic acid primer, and
   cleaving the cleavable chemical group from the 3' O-atom group;
h) iteratively repeating step g) until the plurality of second nucleic acid primers are extended up to and including a residue corresponding to the final consecutive nucleotide residue identified in step e);
i) contacting the plurality of extended second primers with (i) at least four different dideoxynucleotide analogues, each having the structure:

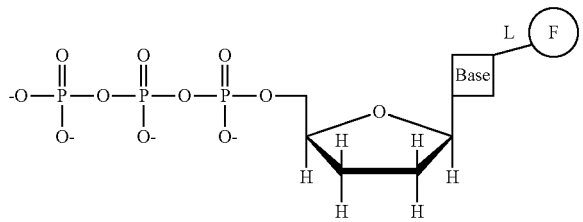

wherein F is a fluorophore, L is a cleavable linker, the base is adenine, guanine, cytosine, uracil or thymine, wherein the fluorophore attached through the cleavable linker to each type of base differs in its emission or excitation spectra from a fluorophore attached to each of the remaining types of bases, and each of the four dideoxynucleotide analogues differs from the remaining three dideoxynucleotide analogues by having a different base, (ii) at least four deoxynucleotide analogues having the structure:

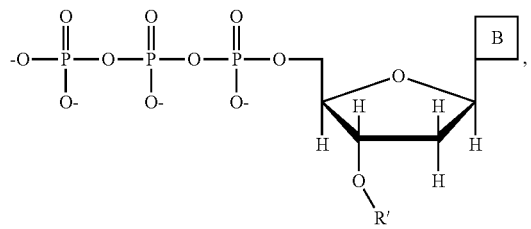

wherein B is a base and is adenine, guanine, cytosine, uracil, or thymine, and wherein R' is a cleavable chemical group, wherein each of the four deoxynucleotide analogues differs from the remaining three deoxynucleotide analogues by having a different base, and
   (iii) a nucleic acid polymerase,
under conditions permitting (a) one of the four dideoxynucleotide analogues that is complementary to the next consecutive nucleotide residue to be identified to form a phosphodiester bond with the 3' end of one of the extended second nucleic acid primers and thereby extend the second primer and (b) one of the four deoxynucleotide analogues that is complementary to a consecutive nucleotide residue to be identified to form a phosphodiester bond with the 3' end of another one of the extended second nucleic acid primers and thereby extend that second primer;
j) identifying the fluorophore of the dideoxynucleotide analogue which has formed the phosphodiester bond, thereby identifying the consecutive nucleotide;
k) cleaving the linker attaching the fluorophore of the dideoxynucleotide analogue which has formed the phosphodiester bond and cleaving the cleavable chemical group from the dNTP which has formed the phosphodiester bond;
l) iteratively repeating steps i) through k) for each of the consecutive nucleotide residues to be identified until the final consecutive nucleotide residue is to be identified;
m) repeating steps i) and j) to identify the final consecutive nucleotide residue,
so as to thereby determine the identity of each of the series of consecutive nucleotide residues in the nucleic acid.

2. The method of claim 1, wherein the cleavable linker in each of step a) and i) independently each comprise the structure:

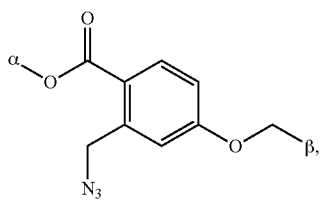

or the structure:

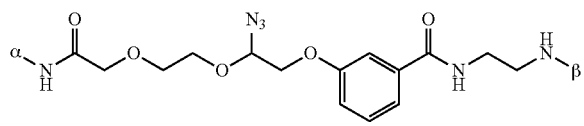

wherein α represents a point of attachment to the base and β represents a point of attachment to the fluorophore.

3. The method of claim 1, wherein a linker is cleaved by contacting the linker with tris(2-carboxyethyl)phosphine; or wherein one or more linkers are photocleavable or chemically cleavable.

4. The method of claim 1, wherein one or more chemical groups are photocleavable or chemically cleavable.

5. The method of claim 1, wherein R' in the structures set forth in steps a) and/or i) is independently chosen from

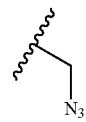

or an allyl group; or wherein the cleavable chemical group in step g) is independently chosen from

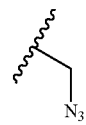

or an allyl group.

6. The method of claim 1, wherein in step g)2)(I) and g)2)(II) or step g)3) three types of deoxynucleotide are chosen, and the three types of dNTPs chosen are from the group dATP, dCTP, dGTP and dTTP.

7. The method of claim 1, wherein the plurality of nucleic acid primers in step a) and the plurality of second nucleic acid primers in step g) have the same sequence.

8. The method of claim 1, wherein one or more washing steps are performed in between one or more of the steps set forth.

* * * * *

```
                        SEQUENCE LISTING

<160> NUMBER OF SEQ ID NOS: 17

<210> SEQ ID NO 1
<211> LENGTH: 26
<212> TYPE: DNA
<213> ORGANISM: Artificial Sequence
<220> FEATURE:
<223> OTHER INFORMATION: self-priming DNA template for ddATP-PC-ROX
      incorporation

<400> SEQUENCE: 1
gactgcgccg cgccttggcg cggcgc                                          26

<210> SEQ ID NO 2
<211> LENGTH: 26
<212> TYPE: DNA
<213> ORGANISM: Artificial Sequence
<220> FEATURE:
<223> OTHER INFORMATION: self-priming DNA template for ddCTP-Bodipy-FL-
      510 incorporation

<400> SEQUENCE: 2
atcggcgccg cgccttggcg cggcgc                                          26

<210> SEQ ID NO 3
<211> LENGTH: 26
<212> TYPE: DNA
<213> ORGANISM: Artificial Sequence
<220> FEATURE:
<223> OTHER INFORMATION: self-priming DNA template for ddGTP-PC-Bodipy-
      650 incorporation

<400> SEQUENCE: 3
gatcgcgccg cgccttggcg cggcgc                                          26
```

```
<210> SEQ ID NO 4
<211> LENGTH: 26
<212> TYPE: DNA
<213> ORGANISM: Artificial Sequence
<220> FEATURE:
<223> OTHER INFORMATION: self-priming DNA template for ddUTP-PC-R6G
      incorporation

<400> SEQUENCE: 4
gtcagcgccg cgccttggcg cggcgc                                       26

<210> SEQ ID NO 5
<211> LENGTH: 18
<212> TYPE: DNA
<213> ORGANISM: Artificial Sequence
<220> FEATURE:
<223> OTHER INFORMATION: Primer directed to DNA sequence of SEQ ID NO: 6

<400> SEQUENCE: 5
agaggatcca accgagac                                                18

<210> SEQ ID NO 6
<211> LENGTH: 60
<212> TYPE: DNA
<213> ORGANISM: Homo sapiens

<400> SEQUENCE: 6
gtgtacatca acatcaccta ccaccatgtc agtctcggtt ggatcctcta ttgtgtccgg  60

<210> SEQ ID NO 7
<211> LENGTH: 4
<212> TYPE: DNA
<213> ORGANISM: Homo sapiens

<400> SEQUENCE: 7 actg                                                                4

<210> SEQ ID NO 8
<211> LENGTH: 14
<212> TYPE: DNA
<213> ORGANISM: Artificial Sequence
<220> FEATURE:
<223> OTHER INFORMATION: DNA template for template "walking"

<400> SEQUENCE: 8
aatcatctcg catg                                                    14

<210> SEQ ID NO 9
<211> LENGTH: 10
<212> TYPE: DNA
<213> ORGANISM: Artificial Sequence
<220> FEATURE:
<223> OTHER INFORMATION: Polymerase extension reaction product of SEQ ID
      No: 8
<220> FEATURE:
<221> NAME/KEY: modified_base
<222> LOCATION: (10)..(10)
<223> OTHER INFORMATION: R6G-R2

<400> SEQUENCE: 9
catgcgagau                                                         10

<210> SEQ ID NO 10
<211> LENGTH: 10
<212> TYPE: DNA
<213> ORGANISM: Artificial Sequence
```

```
<220> FEATURE:
<223> OTHER INFORMATION: Polymerase extension reaction product of SEQ ID
      No: 8
<220> FEATURE:
<221> NAME/KEY: modified_base
<222> LOCATION: (10)..(10)
<223> OTHER INFORMATION: 3'-R1

<400> SEQUENCE: 10
catgcgagat                                                              10

<210> SEQ ID NO 11
<211> LENGTH: 14
<212> TYPE: DNA
<213> ORGANISM: Artificial Sequence
<220> FEATURE:
<223> OTHER INFORMATION: DNA template for template "walking"

<400> SEQUENCE: 11
aatctactag catg                                                         14

<210> SEQ ID NO 12
<211> LENGTH: 10
<212> TYPE: DNA
<213> ORGANISM: Artificial Sequence
<220> FEATURE:
<223> OTHER INFORMATION: Polymerase extension reaction product of SEQ ID
      No: 11
<220> FEATURE:
<221> NAME/KEY: modified_base
<222> LOCATION: (10)..(10)
<223> OTHER INFORMATION: ROX-R2

<400> SEQUENCE: 12
catgctagta                                                              10

<210> SEQ ID NO 13
<211> LENGTH: 10
<212> TYPE: DNA
<213> ORGANISM: Artificial Sequence
<220> FEATURE:
<223> OTHER INFORMATION: Polymerase extension reaction product of SEQ ID
      No: 11
<220> FEATURE:
<221> NAME/KEY: modified_base
<222> LOCATION: (10)..(10)
<223> OTHER INFORMATION: 3'-R1

<400> SEQUENCE: 13
catgctagta                                                              10

<210> SEQ ID NO 14
<211> LENGTH: 21
<212> TYPE: DNA
<213> ORGANISM: Artificial Sequence
<220> FEATURE:
<223> OTHER INFORMATION: Chemically synthesized DNA template for
      sequence by synthesis

<400> SEQUENCE: 14
tgttaatcat gttgttgcat g                                                 21

<210> SEQ ID NO 15
<211> LENGTH: 10
<212> TYPE: DNA
<213> ORGANISM: Artificial Sequence
<220> FEATURE:
<223> OTHER INFORMATION: Polymerase extension reaction product of SEQ ID
      No: 8
```

```
<220> FEATURE:
<221> NAME/KEY: modified_base
<222> LOCATION: (10)..(10)
<223> OTHER INFORMATION: ROX-R2; 3'-R1

<400> SEQUENCE: 15
catgcgagau                                                          10

<210> SEQ ID NO 16
<211> LENGTH: 10
<212> TYPE: DNA
<213> ORGANISM: Artificial Sequence
<220> FEATURE:
<223> OTHER INFORMATION: Polymerase extension reaction product of SEQ ID
      No: 11
<220> FEATURE:
<221> NAME/KEY: modified_base
<222> LOCATION: (10)..(10)
<223> OTHER INFORMATION: ROX-R2; 3'-R1

<400> SEQUENCE: 16
catgctagta                                                          10

<210> SEQ ID NO 17
<211> LENGTH: 10
<212> TYPE: DNA
<213> ORGANISM: Artificial Sequence
<220> FEATURE:
<223> OTHER INFORMATION: Polymerase extension reaction product of SEQ ID
      No: 11
<220> FEATURE:
<221> NAME/KEY: modified_base
<222> LOCATION: (10)..(10)
<223> OTHER INFORMATION: 3'-R1

<400> SEQUENCE: 17
catgctagua                                                          10
```